(12) United States Patent
Adachi et al.

(10) Patent No.: US 9,153,788 B2
(45) Date of Patent: Oct. 6, 2015

(54) ORGANIC LIGHT-EMITTING DEVICE, AND DELAYED FLUORESCENT MATERIAL AND COMPOUND USED THEREFOR

(71) Applicant: KYUSHU UNIVERSITY NATIONAL UNIVERSITY CORPORATION, Fukuoka-shi, Fukuoka (JP)

(72) Inventors: Chihaya Adachi, Fukuoka (JP); Takuma Yasuda, Fukuoka (JP); Saeyoun Lee, Fukuoka (JP); Hiroko Nomura, Fukuoka (JP); Tetsuya Nakagawa, Fukuoka (JP)

(73) Assignee: KYUSHU UNIVERSITY NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 14/362,153

(22) PCT Filed: Nov. 30, 2012

(86) PCT No.: PCT/JP2012/081027
§ 371 (c)(1),
(2) Date: Jun. 2, 2014

(87) PCT Pub. No.: WO2013/081088
PCT Pub. Date: Jun. 6, 2013

(65) Prior Publication Data
US 2014/0336379 A1    Nov. 13, 2014

(30) Foreign Application Priority Data

Dec. 2, 2011    (JP) .................................. 2011-265215

(51) Int. Cl.
| | |
|---|---|
| C07D 403/14 | (2006.01) |
| C09K 11/06 | (2006.01) |
| H01L 51/50 | (2006.01) |
| H01L 51/54 | (2006.01) |
| H05B 33/14 | (2006.01) |
| H01L 51/00 | (2006.01) |

(52) U.S. Cl.
CPC .......... *H01L 51/0067* (2013.01); *C07D 403/14* (2013.01); *C09K 11/06* (2013.01); *H01L 51/0072* (2013.01); *C09K 2211/1007* (2013.01); *C09K 2211/1029* (2013.01); *C09K 2211/1044* (2013.01); *C09K 2211/1059* (2013.01); *H01L 51/5012* (2013.01)

(58) Field of Classification Search
CPC .. C07D 403/04; C09K 11/06; H01L 51/5032; H01L 51/5064; H01L 51/5296; H01L 51/0032; H05B 33/14
USPC ........... 544/194, 198, 209; 428/917
See application file for complete search history.

(56) References Cited

U.S. PATENT DOCUMENTS

2013/0248845 A1    9/2013    Ogawa et al.
2013/0306959 A1    11/2013   Ikeda et al.

FOREIGN PATENT DOCUMENTS

| JP | 2002198176 A | 7/2002 |
|---|---|---|
| JP | 2004171808 A | 6/2004 |
| JP | 2006278494 A | 10/2006 |
| JP | 2007077033 A | 3/2007 |
| JP | 2010121041 A | 6/2010 |
| JP | 2013-116975 A1 | 6/2013 |
| JP | 2013533604 A | 8/2013 |
| WO | 2011057706 A2 | 5/2011 |
| WO | 2011139055 A2 | 11/2011 |
| WO | 2011148909 A1 | 12/2011 |
| WO | 2011162162 A1 | 12/2011 |
| WO | 2012077520 A1 | 6/2012 |
| WO | 2012086170 A1 | 6/2012 |

OTHER PUBLICATIONS

Official Action, dated Nov. 11, 2014. In corresponding Japanese patent application No. 2013547225.
Office Action dated Jun. 11, 2014 in corresponding Japanese Patent Application No. 2013-547225.
Notice of Transmittal dated Jun. 12, 2014 International application No. PCT/JP2012081027.
International Search Report dated Mar. 5, 2013. International application No. PCT/JP2012081027.

*Primary Examiner* — Venkataraman Balasubramanian
(74) *Attorney, Agent, or Firm* — Browdy and Neimark, P.L.L.C.

(57) ABSTRACT

An organic light-emitting device containing a compound represented by the following general formula in a light light-emitting layer has a high light-emission efficiency. The ring containing $Y^1$, $Y^2$ and $Y^3$ represent a triazine ring or a pyrimidine ring; $Z^1$, $Z^2$ and $R^1$ to $R^8$ represent a hydrogen atom or a substituent; and at least one of $R^1$ to $R^8$ represents a diarylamino group or a carbazolyl group. The compound represented by the general formula (1) contains at least two carbazole structures in the molecule thereof.

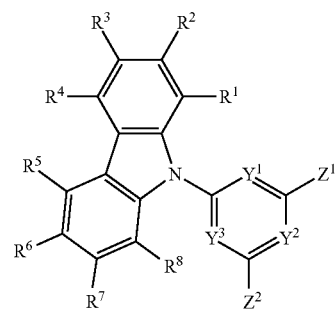

6 Claims, 4 Drawing Sheets

ORGANIC LIGHT-EMITTING DEVICE, AND DELAYED FLUORESCENT MATERIAL AND COMPOUND USED THEREFOR

TECHNICAL FIELD

The present invention relates to an organic light-emitting device having a high light emission efficiency. The invention also relates to a delayed fluorescent material and a compound used therefor.

BACKGROUND ART

Organic light-emitting devices, such as an organic electroluminescent device (organic EL device), have been actively studied for enhancing the light emission efficiency, where light emission efficiency is defined and hereafter used for mean photoluminescence quantum efficiency, electroluminescence quantum efficiency, or both as appropriate thereof. In particular, various studies for enhancing the light emitting efficiency have been made by newly developing and combining an electron transporting material, a hole transporting material, a light-emitting material and the like constituting an organic electroluminescent device. There are studies relating to an organic electroluminescent device utilizing a compound containing a carbazole structure, which are found among them, and some proposals have been made hitherto.

For example, PTL 1 describes the use of the following triazine compounds substituted by a 3,6-bis(dimethylamino)-9-carbazolyl group or a 3,6-bis(diphenylamino)-9-carbazolyl group as a host material of a light-emitting layer of an organic electroluminescent device.

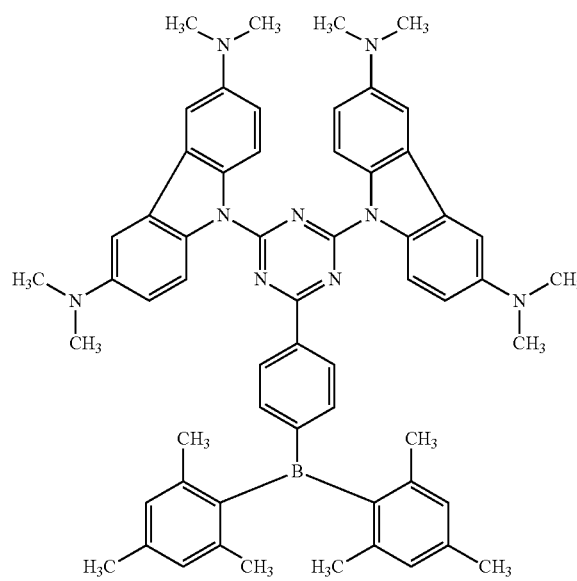

PTL 2 describes the use of the following triazine compound substituted by a 3,6-bis(9-carbazolyl)-9-carbazolyl group as a host material of a light-emitting layer of an organic electroluminescent device.

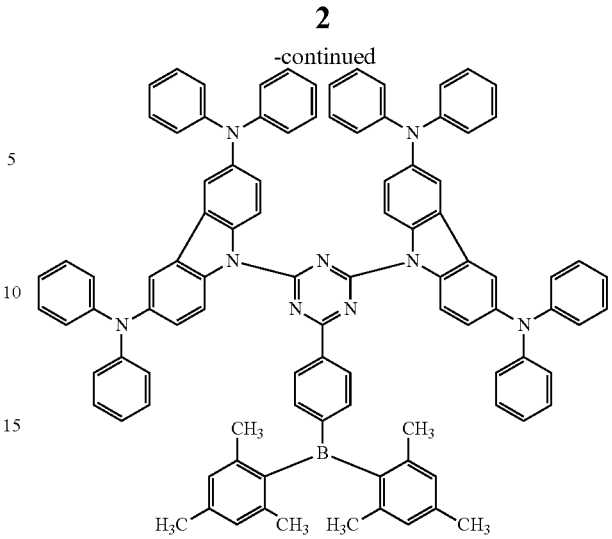

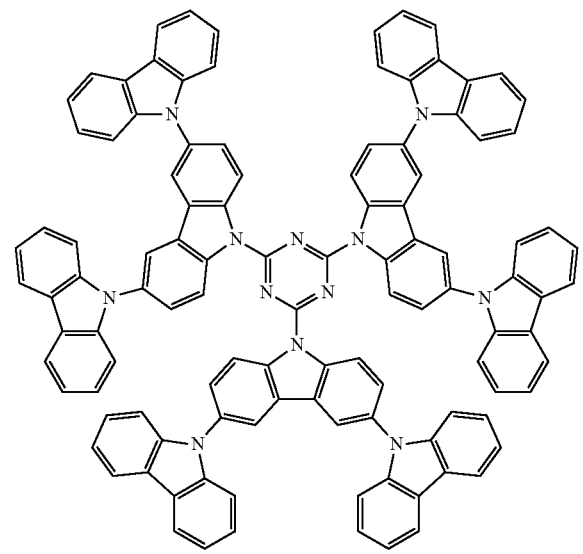

CITATION LIST

Patent Literatures

[PTL 1]
  JP-A-2007-77033
[PTL 2]
  JP-A-2004-171808

SUMMARY OF INVENTION

Technical Problem

As described above, compounds containing a carbazole structure have been variously studied, and some proposals relating to application thereof to an organic electroluminescent device have been made. In most of the organic electroluminescent devices having been proposed, however, the proposals therein are the use of a compound containing a carbazole structure as a host material of a light-emitting layer. Furthermore, the light emission efficiency thereof is not necessarily high. Moreover, it may not be said that all the compounds containing a carbazole structure have been comprehensively studied. In particular, with respect to the purpose as a light-emitting material of a triazine compound containing a carbazole structure and a pyrimidine compound containing a carbazole structure, only some compounds have been confirmed for the usefulness thereof. There is no clear relationship having been found between the chemical structure of the compound containing a carbazole structure and the usefulness of the compound as a light-emitting material, and it is the current situation that it is difficult to estimate the usefulness as a light-emitting material based on the chemical structure. The present inventors have considered these problems and have made investigations for evaluating the compounds containing a carbazole structure that have not been investigated, as a light-emitting material of an organic light-emitting device. The inventors also have made investigations for providing a general formula of compounds that are useful as a light-emitting material and generalizing the structure of an organic light-emitting device having a high light emission efficiency.

Solution to Problem

As a result of earnest investigations for achieving the objects, the inventors have clarified that particular triazine compounds and pyrimidine compounds having a carbazole structure are extremely useful as a light-emitting material of an organic electroluminescent device. In particular, the inventors have found compounds that are useful as a delayed fluorescent material in triazine compounds and pyrimidine compounds having a carbazole structure, and have clarified that an organic light-emitting device having a high light emission efficiency may be provided inexpensively. Based on the knowledge, the inventors have provided the following inventions as measures for solving the problems.

(1) An organic light-emitting device containing a substrate having thereon a light-emitting layer containing a compound represented by the following general formula (1) as a light-emitting material:

General Formula (1)

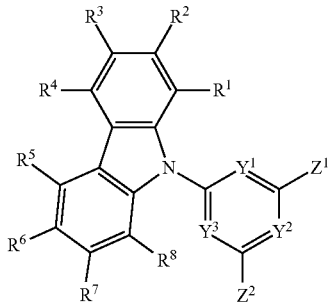

wherein in the general formula (1), any two of $Y^1$, $Y^2$ and $Y^3$ represent nitrogen atoms and the other one thereof represents a methine group, or $Y^1$, $Y^2$ and $Y^3$ all represent nitrogen atoms; $Z^1$ and $Z^2$ each independently represent a hydrogen atom or a substituent; and $R^1$ to $R^8$ each independently represent a hydrogen atom or a substituent, provided that at least one of $R^1$ to $R^8$ represents a substituted or unsubstituted diarylamino group or a substituted or unsubstituted carbazolyl group, and the compound represented by the general formula (1) contains at least two carbazole structures in the molecule thereof.

(2) The organic light-emitting device according to the item (1), which emits delayed fluorescent light.

(3) The organic light-emitting device according to the item (1) or (2), which is an organic electroluminescent device.

(4) The organic light-emitting device according to any one of the items (1) to (3), which contains a substrate having thereon a light-emitting layer containing a compound represented by the following general formula (2) as a light-emitting material:

General Formula (2)

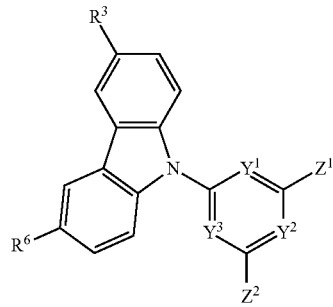

wherein in the general formula (2), any two of $Y^1$, $Y^2$ and $Y^3$ represent nitrogen atoms and the other one thereof represents a methine group, or $Y^1$, $Y^2$ and $Y^3$ all represent nitrogen atoms; $Z^1$ represents a substituted or unsubstituted aryl group, a substituted or unsubstituted heteroaryl group or a substituted or unsubstituted 9-carbazolyl group; $Z^2$ represents a hydrogen atom, a substituted or unsubstituted alkyl group, a substituted or unsubstituted aryl group or a substituted or unsubstituted heteroaryl group; $R^3$ represents a substituted or unsubstituted diarylamino group or a carbazolyl group; and $R^6$ represents a hydrogen atom or a substituent, and the compound represented by the general formula (2) contains at least two carbazole structures in the molecule thereof.

(5) The organic light-emitting device according to any one of the items (1) to (3), which contains a substrate having thereon a light-emitting layer containing a compound represented by the following general formula (3) as a light-emitting material:

General Formula (3)

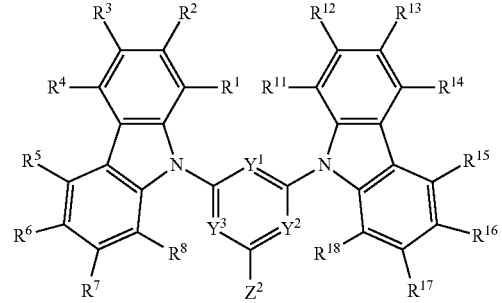

wherein in the general formula (3), any two of $Y^1$, $Y^2$ and $Y^3$ represent nitrogen atoms and the other one thereof represents a methine group, or $Y^1$, $Y^2$ and $Y^3$ all represent nitrogen atoms; $Z^2$ represents a hydrogen atom or a substituent; and $R^1$ to $R^8$ and $R^{11}$ to $R^{18}$ each independently represent a hydrogen atom or a substituent, provided that at least one of $R^1$ to $R^8$ represents a substituted or unsubstituted diarylamino group or a substituted or unsubstituted carbazolyl group.

(6) The organic light-emitting device according to any one of the items (1) to (3), which contains a substrate having thereon a light-emitting layer containing a compound represented by the following general formula (4) as a light-emitting material:

General Formula (4)

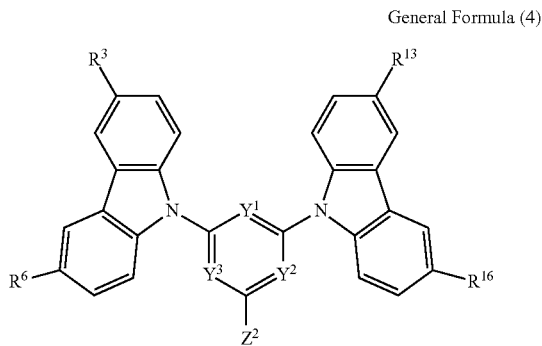

wherein in the general formula (4), any two of $Y^1$, $Y^2$ and $Y^3$ represent nitrogen atoms and the other one thereof represents a methine group, or $Y^1$, $Y^2$ and $Y^3$ all represent nitrogen atoms; $Z^2$ represents a hydrogen atom or a substituent; and $R^3$, $R^6$, $R^{13}$ and $R^{16}$ each independently represent a hydrogen atom or a substituent, provided that at least one of $R^3$ and $R^6$ represents a substituted or unsubstituted diarylamino group or a substituted or unsubstituted carbazolyl group.

(7) The organic light-emitting device according to any one of the items (1) to (3), which contains a substrate having thereon a light-emitting layer containing a compound represented by the following general formula (5) as a light-emitting material:

General Formula (5)

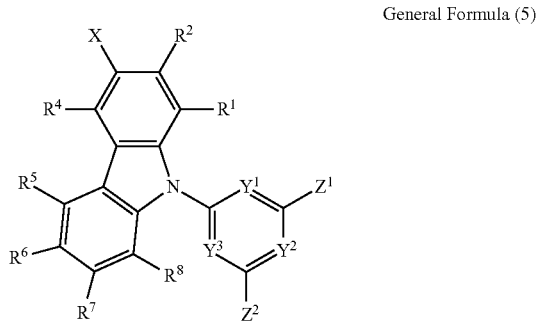

wherein in the general formula (5), any two of $Y^1$, $Y^2$ and $Y^3$ represent nitrogen atoms and the other one thereof represents a methine group, or $Y^1$, $Y^2$ and $Y^3$ all represent nitrogen atoms; $Z^1$ and $Z^2$ each independently represent a hydrogen atom or a substituent; $R^1$, $R^2$ and $R^4$ to $R^8$ each independently represent a hydrogen atom or a substituent; and X represents a substituted or unsubstituted diarylamino group or a substituted or unsubstituted carbazolyl group.

(8) The organic light-emitting device according to any one of the items (1) to (3), which contains a substrate having thereon a light-emitting layer containing a compound represented by the following general formula (6) as a light-emitting material:

General Formula (6)

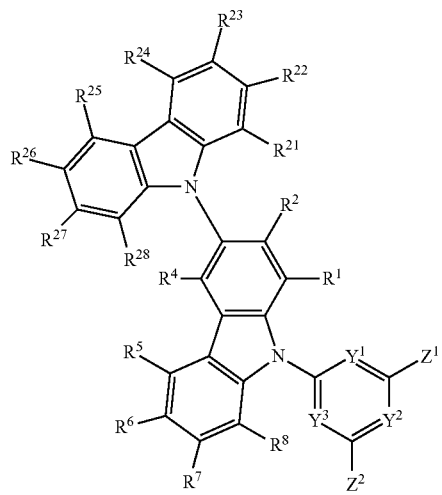

wherein in the general formula (6), any two of $Y^1$, $Y^2$ and $Y^3$ represent nitrogen atoms and the other one thereof represents a methine group, or $Y^1$, $Y^2$ and $Y^3$ all represent nitrogen atoms; $Z^1$ and $Z^2$ each independently represent a hydrogen atom or a substituent; and $R^1$, $R^2$, $R^4$ to $R^8$, and $R^{21}$ to $R^{28}$ each independently represent a hydrogen atom or a substituent.

(9) A delayed fluorescent material containing a compound represented by the general formula (1).

(10) The delayed fluorescent material according to the item (9), which is for an organic electroluminescent device.

(11) The delayed fluorescent material according to the item (9) or (10), which contains a compound represented by the general formula (2).

(12) The delayed fluorescent material according to the item (9) or (10), which contains a compound represented by the general formula (3).

(13) The delayed fluorescent material according to the item (9) or (10), which contains a compound represented by the general formula (4).

(14) The delayed fluorescent material according to the item (9) or (10), which contains a compound represented by the general formula (5).

(15) The delayed fluorescent material according to the item (9) or (10), which contains a compound represented by the general formula (6).

(16) A compound represented by the following general formula (11):

General Formula (11)

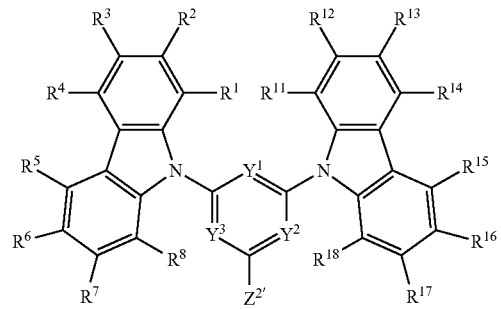

wherein in the general formula (11), any two of $Y^1$, $Y^2$ and $Y^3$ represent nitrogen atoms and the other one thereof represents a methine group, or $Y^1$, $Y^2$ and $Y^3$ all represent nitrogen atoms; $Z^{2'}$ represents a hydrogen atom or a substituent that is bonded via a carbon atom (provided that the substituent does not contain a boron atom); and $R^1$ to $R^8$ and $R^{11}$ to $R^{18}$ each independently represent a hydrogen atom or a substituent, provided that at least one thereof represents a substituted or unsubstituted diarylamino group or a substituted or unsubstituted carbazolyl group.

(17) The compound according to the item (16), which is represented by the following general formula (12):

General Formula (12)

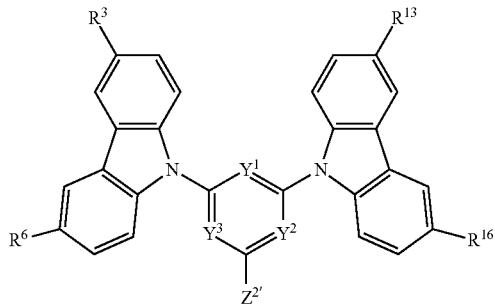

wherein in the general formula (12), any two of $Y^1$, $Y^2$ and $Y^3$ represent nitrogen atoms and the other one thereof represents a methine group, or $Y^1$, $Y^2$ and $Y^3$ all represent nitrogen atoms; $Z^{2'}$ represents a hydrogen atom, a substituted or unsubstituted alkyl group, a substituted or unsubstituted alkoxy group, a substituted or unsubstituted aryl group, a substituted or unsubstituted heteroaryl group (which is limited to a group that is bonded via a carbon atom), a substituted or unsubstituted alkenyl group, a substituted or unsubstituted alkynyl group, a substituted or unsubstituted haloalkyl group, a substituted or unsubstituted trialkylsilylalkyl group, a substituted or unsubstituted trialkylsilylalkenyl group, a substituted or unsubstituted trialkylsilylalkynyl group or a cyano group; and $R^3$, $R^6$, $R^{13}$ and $R^{16}$ each independently represent a hydrogen atom or a substituent, provided that at least one thereof represents a substituted or unsubstituted diarylamino group or a substituted or unsubstituted carbazolyl group.

Advantageous Effects of Invention

The organic light-emitting device of the invention has such a feature that the device has a high light emission efficiency. The delayed fluorescent material of the invention has such a feature that when the material is used in a light-emitting layer of an organic light-emitting device, the organic light-emitting device emits delayed fluorescent light with a light emission efficiency that is drastically enhanced. The compound of the invention is extremely useful as a light-emitting material for the organic light-emitting device.

DESCRIPTION OF EMBODIMENTS

Figure 1:
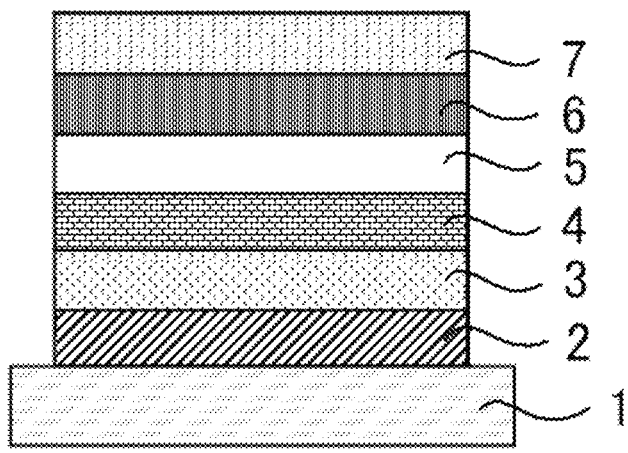
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the present specification, a numerical range expressed by "from X to Y" means a range including the numerals X and Y as the lower limit and the upper limit, respectively.

Compound Represented by General Formula (1)

The organic light-emitting device of the invention contains the compound represented by the following general formula (1) as a light-emitting material of a light-emitting layer. The compound represented by the general formula (1) will be described.

General Formula (1)

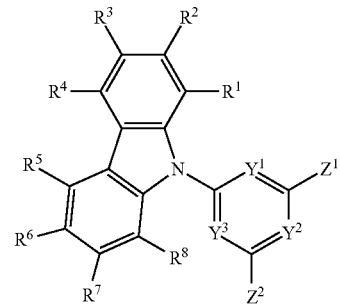

In the general formula (1), any two of $Y^1$, $Y^2$ and $Y^3$ represent nitrogen atoms and the other one thereof represents a methine group, or $Y^1$, $Y^2$ and $Y^3$ all represent nitrogen atoms. In the case where any two of $Y^1$, $Y^2$ and $Y^3$ represent nitrogen atoms and the other one thereof represents a methine group, the ring containing $Y^1$, $Y^2$ and $Y^3$ is a pyrimidine ring. In this case, the methine group may be any one of $Y^1$, $Y^2$ and $Y^3$, and is preferably $Y^1$ or $Y^3$. In the case where $Y^1$, $Y^2$ and $Y^3$ all represent nitrogen atoms, the ring containing $Y^1$, $Y^2$ and $Y^3$ is a triazine ring.

In the general formula (1), $Z^1$ and $Z^2$ each independently represent a hydrogen atom or a substituent. Examples of the preferred substituent that is capable of being represented by $Z^1$ and $Z^2$ include an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, a diarylamino group having from 12 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, a cyano group, a nitro group and a hydroxyl group, which may be further substituted by a substituent. $Z^1$ and $Z^2$ each more preferably independently represent a hydrogen atom, a substituted or unsubstituted alkyl group having from 1 to 20 carbon atoms, a substituted or unsubstituted aryl group having from 6 to 40 carbon atoms, a substituted or unsubstituted heteroaryl group having from 3 to 40 carbon atoms, a substituted or unsubstituted diarylamino group having from 12 to 40 carbon atoms or a substituted or unsubstituted carbazolyl group having from 12 to 40 carbon atoms. $Z^1$ and $Z^2$ each further preferably independently represent a hydrogen atom, a substituted or unsubstituted alkyl group having from 1 to 10 carbon atoms, a substituted or unsubstituted aryl group having from 6 to 15 carbon atoms, a substituted or unsubstituted heteroaryl group having from 3 to 12 carbon atoms or a substituted or unsubstituted 9-carbazolyl group having from 12 to 24 carbon atoms. $Z^1$ still further preferably represents a substituted or unsubstituted aryl group having from 6 to 15 carbon atoms, a substituted or unsubstituted heteroaryl group having from 3 to 12 carbon atoms or a substituted or unsubstituted 9-carbazolyl group having from 12 to 24 carbon atoms. $Z^2$ still further preferably represents a hydrogen atom, a substituted or unsubstituted alkyl group having from 1 to 10 carbon atoms, a substituted or unsubstituted aryl group having from 6 to 15 carbon atoms or a substituted or unsubstituted heteroaryl group having from 3 to 12 carbon atoms.

The alkyl group may be linear, branched or cyclic, and more preferably has from 1 to 6 carbon atoms, and specific examples thereof include a methyl group, an ethyl group, a propyl group, a butyl group, a tert-butyl group, a pentyl group, a hexyl group and an isopropyl group. The aryl group may be a monocyclic ring or a fused ring, and specific examples thereof include a phenyl group and a naphthyl group. The heteroaryl group may also be a monocyclic ring or a fused ring, and specific examples thereof include a pyridyl group, a pyridazyl group, a pyrimidyl group, a triazyl group, a troa-zolyl group and a benzotriazolyl group. These heteroaryl groups may be a group that is bonded via a hetero atom, and is preferably a group that is bonded via a carbon atom constituting the heteroaryl ring. In the case where the 9-carbazolyl group is substituted, it is preferably substituted with the alkyl group, the aryl group or the heteroaryl group mentioned above, or with a cyano group, a diarylamino group or a carbazolyl group.

In the general formula (1), $R^1$ to $R^8$ each independently represent a hydrogen atom or a substituent. Examples of the preferred substituent that is capable of being represented by $R^1$ to $R^8$ include an alkyl group having from 1 to 20 carbon atoms, an aralkyl group having from 7 to 20 carbon atoms, an alkenyl group having from 2 to 20 carbon atoms, an alkynyl group having from 2 to 20 carbon atoms, an aryl group having from 6 to 30 carbon atoms, a heteroaryl group having from 3 to 30 carbon atoms, a cyano group, a dialkylamino group having from 2 to 20 carbon atoms, a diarylamino group having from 12 to 30 carbon atoms, a carbazolyl group having from 12 to 30 carbon atoms, a diaralkylamino group having from 12 to 30 carbon atoms, an amino group, a nitro group, an acyl group having from 2 to 20 carbon atoms, an alkoxycarbonyl group having from 2 to 20 carbon atoms, an alkoxy group having from 1 to 20 carbon atoms, an alkylsulfonyl group having from 1 to 20 carbon atoms, a hydroxyl group, an amide group, a haloalkyl group having from 1 to 10 carbon atoms, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms and a trialkylsilylalkynyl group having from 5 to 20 carbon atoms, which may be further substituted by a substituent. $R^1$ to $R^8$ each more preferably independently represent a hydrogen atom, a substituted or unsubstituted alkyl group having from 1 to 20 carbon atoms, a substituted or unsubstituted aryl group having from 6 to 30 carbon atoms, a substituted or unsubstituted heteroaryl group having from 3 to 30 carbon atoms, a substituted or unsubstituted diarylamino group having from 12 to 30 carbon atoms or a carbazolyl group having from 12 to 30 carbon atoms. $R^1$ to $R^8$ each further preferably independently represent a hydrogen atom, a substituted or unsubstituted alkyl group having from 1 to 10 carbon atoms, a substituted or unsubstituted aryl group having from 6 to 15 carbon atoms, a substituted or unsubstituted heteroaryl group having from 3 to 12 carbon atoms, a substituted or unsubstituted diphenylamino group having from 12 to 24 carbon atoms or a carbazolyl group having from 12 to 24 carbon atoms.

In the general formula (1), at least one of $R^1$ to $R^8$ represents a substituted or unsubstituted diarylamino group or a substituted or unsubstituted carbazolyl group. Specific examples of the carbazolyl group include a 9-carbazolyl group, a 1-carbazolyl group, a 2-carbazolyl group, a 3-carbazolyl group and a 4-carbazolyl group, and preferred examples thereof include a 9-carbazolyl group and a 3-carbazolyl group, and the carbazolyl group is more preferably a 9-carbazolyl group. In the case where the diarylamino group and the carbazolyl group have a substituent, the substituent is not restricted in species thereof, and preferred examples thereof include the preferred substituents that are capable of being represented by $R^1$ to $R^8$ mentioned above. In the general formula (1), any of $R^1$ to $R^8$ may be a substituted or unsubstituted diarylamino group or a substituted or unsubstituted carbazolyl group, and at least one of $R^3$ and $R^6$ is preferably a substituted or unsubstituted diarylamino group or a substituted or unsubstituted carbazolyl group.

The compound represented by the general formula (1) contains at least two carbazole structures in the molecule thereof. One carbazol structure has been in the general formula (1), and thus at least one of $R^1$ to $R^8$, $Z^1$ and $Z^2$ is necessarily a group that contains a carbazole structure. It is preferred that at least one of $R^1$ to $R^4$, $R^5$ to $R^8$ and $Z^1$ is a group that contains a carbazole structure. It is more preferred that at least one of $R^3$, $R^6$ and $Z^1$ is a group that contains a carbazole structure. It is preferred that any two of $R^3$, $R^6$ and $Z^1$ each are a group that contains a carbazole structure, and it is preferred that all of them each are a group that contains a carbazole structure.

The compound represented by the general formula (1) is more preferably a compound containing at least three carbazole structures in the molecule thereof, and further preferably a compound containing at least four carbazole structures in the molecule thereof. The upper limit of the number of carbazole structures in the molecule is not particularly limited, and the number of carbazole structure may be, for example, 8 or less, and also may be 6 or less.

The compound represented by the general formula (1) is preferably a compound having a structure represented by the following general formula (2).

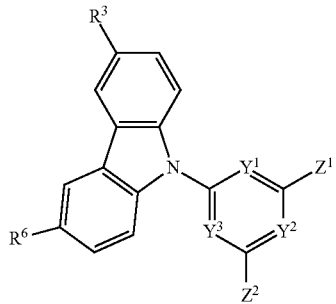

General Formula (2)

In the general formula (2), any two of $Y^1$, $Y^2$ and $Y^3$ represent nitrogen atoms and the other one thereof represents a methine group, or $Y^1$, $Y^2$ and $Y^3$ all represent nitrogen atoms; $Z^1$ represents a substituted or unsubstituted aryl group, a substituted or unsubstituted heteroaryl group, or a substituted or unsubstituted 9-carbazolyl group; $Z^2$ represents a hydrogen atom, a substituted or unsubstituted alkyl group, a substituted or unsubstituted aryl group, or a substituted or unsubstituted heteroaryl group; $R^3$ represents a substituted or unsubstituted diarylamino group or a carbazolyl group; and $R^6$ represents a hydrogen atom or a substituent. The compound represented by the general formula (2) contains at least two carbazole structures in the molecule thereof.

In the general formula (2), $Z^1$ more preferably represents a substituted or unsubstituted aryl group having from 6 to 40 carbon atoms, a substituted or unsubstituted heteroaryl group having from 3 to 40 carbon atoms or a substituted or unsubstituted 9-carbazolyl group having from 12 to 40 carbon atoms, further preferably a substituted or unsubstituted aryl group having from 6 to 40 carbon atoms or a substituted or unsubstituted 9-carbazolyl group having from 12 to 40 carbon atoms, and still further preferably a substituted or unsubstituted aryl group having from 6 to 15 carbon atoms or a substituted or unsubstituted 9-carbazolyl group having from 12 to 24 carbon atoms. In the case where both $R^3$ and $R^6$ are not a carbazolyl group, $Z^1$ is preferably a substituted or unsubstituted 9-carbazolyl group.

In the general formula (2), $Z^2$ more preferably represents a hydrogen atom, a substituted or unsubstituted alkyl group having from 1 to 20 carbon atoms, a substituted or unsubstituted aryl group having from 6 to 40 carbon atoms or a substituted or unsubstituted heteroaryl group having from 3 to 40 carbon atoms, and further preferably a hydrogen atom, a substituted or unsubstituted alkyl group having from 1 to 10 carbon atoms, a substituted or unsubstituted aryl group having from 6 to 15 carbon atoms or a substituted or unsubstituted heteroaryl group having from 3 to 12 carbon atoms.

In the general formula (2), $R^3$ more preferably represents a substituted or unsubstituted diarylamino group having from to 30 carbon atoms, a substituted or unsubstituted 9-carbazolyl group having from 12 to 30 carbon atoms, a substituted or unsubstituted 1-carbazolyl group having from 12 to 30 carbon atoms, a substituted or unsubstituted 2-carbazolyl group having from 12 to 30 carbon atoms, a substituted or unsubstituted 3-carbazolyl group having from 12 to 30 carbon atoms or a substituted or unsubstituted 4-carbazolyl group having from 12 to 30 carbon atoms, and further preferably a substituted or unsubstituted diarylamino group having from 12 to 30 carbon atoms, a substituted or unsubstituted 9-carbazolyl group having from 12 to 30 carbon atoms or a substituted or unsubstituted 3-carbazolyl group having from 12 to 30 carbon atoms.

In the general formula (2), $R^6$ more preferably represents a hydrogen atom, a substituted or unsubstituted alkyl group having from 1 to 20 carbon atoms, a substituted or unsubstituted aryl group having from 6 to 30 carbon atoms, a substituted or unsubstituted heteroaryl group having from 3 to 30 carbon atoms, a substituted or unsubstituted diarylamino group having from 12 to 30 carbon atoms or a substituted or unsubstituted carbazolyl group having from 12 to 30 carbon atoms, and further preferably a hydrogen atom, a substituted or unsubstituted alkyl group having from 1 to 10 carbon atoms, a substituted or unsubstituted aryl group having from 6 to 15 carbon atoms, a substituted or unsubstituted heteroaryl group having from 3 to 12 carbon atoms, a substituted or unsubstituted diphenylamino group having from 12 to 24 carbon atoms or a substituted or unsubstituted carbazolyl group having from 12 to 24 carbon atoms.

For the descriptions and the preferred ranges of $Y^1$, $Y^2$ and $Y^3$, and the preferred ranges of the substituents in the general formula (2), reference may be made to the corresponding descriptions for the general formula (1).

The compound represented by the general formula (1) is preferably a compound having a structure represented by the following general formula (3).

General Formula (3)

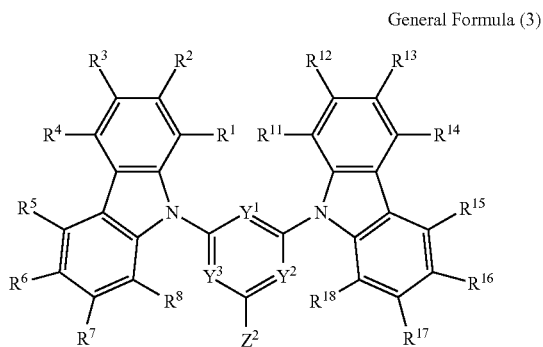

In the general formula (3), any two of $Y^1, Y^2$ and $Y^3$ represent nitrogen atoms and the other one thereof represents a methine group, or $Y^1, Y^2$ and $Y^3$ all represent nitrogen atoms; $Z^2$ represents a hydrogen atom or a substituent; and $R^1$ to $R^8$ and $R^{11}$ to $R^{18}$ each independently represent a hydrogen atom or a substituent, provided that at least one of $R^1$ to $R^8$ represents a substituted or unsubstituted diarylamino group or a substituted or unsubstituted carbazolyl group.

For the descriptions and the preferred ranges of $Y^1, Y^2, Y^3$, $Z^2$ and $R^1$ to $R^8$ in the general formula (3), reference may be made to the corresponding descriptions for the general formula (1). In the case where any two of $Y^1, Y^2$ and $Y^3$ represent nitrogen atoms and the other one thereof represents a methine group, it is most preferred that $Y^1$ is a methine group. For the preferred ranges of $Z^2$, reference may also be made to the corresponding descriptions for the general formula (2). For the descriptions and the preferred ranges of $R^{11}$ to $R^{18}$, reference may be made to the descriptions and the preferred ranges of $R^1$ to $R^8$ in the general formula (1), but it is not necessary that at least one of $R^{11}$ to $R^{18}$ is a substituted or unsubstituted diarylamino group or a substituted or unsubstituted carbazolyl group.

The compound represented by the general formula (3) is more preferably a compound having a structure represented by the following general formula (4).

General Formula (4)

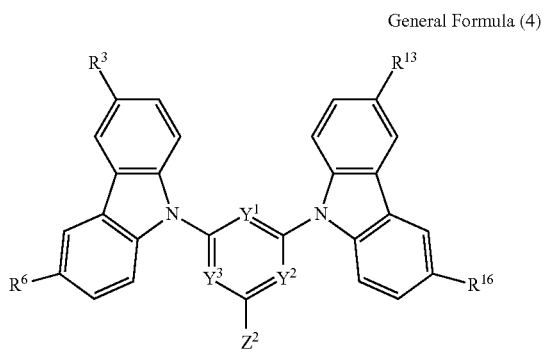

In the general formula (4), any two of $Y^1, Y^2$ and $Y^3$ represent nitrogen atoms and the other one thereof represents a methine group, or $Y^1, Y^2$ and $Y^3$ all represent nitrogen atoms; $Z^2$ represents a hydrogen atom or a substituent; and $R^3, R^6$, $R^{13}$ and $R^{16}$ each independently represent a hydrogen atom or a substituent, provided that at least one of $R^3$ and $R^6$ represents a substituted or unsubstituted diarylamino group or a substituted or unsubstituted carbazolyl group.

For the descriptions and the preferred ranges of $Y^1, Y^2, Y^3$, $Z^2$, $R^3$ and $R^6$ in the general formula (4), reference may be made to the corresponding descriptions for the general formula (1). In the case where any two of $Y^1, Y^2$ and $Y^3$ represent nitrogen atoms and the other one thereof represents a methine group, it is most preferred that $Y^1$ is a methine group. For the preferred ranges of $Z^2$, reference may also be made to the corresponding descriptions for the general formula (2). For the preferred ranges of $R^3$ and $R^6$, reference may also be made to the corresponding descriptions for the general formula (3). For the descriptions and the preferred ranges of $R^{13}$ and $R^{16}$, reference may be made to the descriptions and the preferred ranges of $R^3$ to $R^6$ in the general formula (1), but it is not necessary that at least one of $R^{13}$ and $R^{16}$ is a substituted or unsubstituted diarylamino group or a substituted or unsubstituted carbazolyl group.

The compound represented by the general formula (1) is preferably a compound having a structure represented by the following general formula (5).

General Formula (5)

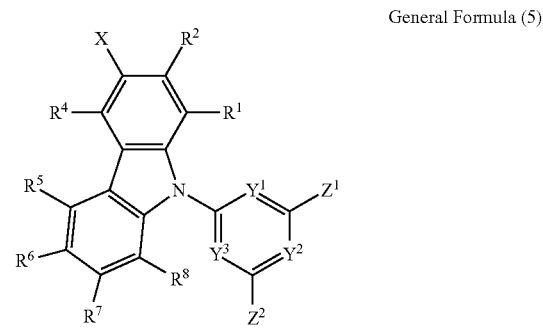

In the general formula (5), any two of $Y^1, Y^2$ and $Y^3$ represent nitrogen atoms and the other one thereof represents a methine group, or $Y^1, Y^2$ and $Y^3$ all represent nitrogen atoms; $Z^1$ and $Z^2$ each independently represent a hydrogen atom or a substituent; $R^1, R^2$ and $R^4$ to $R^8$ each independently represent a hydrogen atom or a substituent; and X represents a substituted or unsubstituted diarylamino group or a substituted or unsubstituted carbazolyl group.

For the descriptions and the preferred ranges of $Y^1, Y^2, Y^3$, $Z^1, Z^2, R^1, R^2$ and $R^4$ to $R^8$, reference may be made to the corresponding descriptions for the general formula (1).

In the general formula (5), X more preferably represents a diarylamino group having from 12 to 30 carbon atoms or a substituted or unsubstituted carbazolyl group having from 12 to 30 carbon atoms. In the case where X represents a substituted or unsubstituted carbazolyl group, the substituted or unsubstituted carbazolyl group includes a substituted or unsubstituted 9-carbazolyl group, a substituted or unsubstituted 1-carbazolyl group, a substituted or unsubstituted 2-carbazolyl group, a substituted or unsubstituted 3-carbazolyl group and a substituted or unsubstituted 4-carbazolyl group. Among these, examples of the group of substituted or unsubstituted carbazolyl groups that is capable of being represented by X include a group consisting of a substituted or unsubstituted 9-carbazolyl group, a substituted or unsubstituted 1-carbazolyl group, a substituted or unsubstituted 2-carbazolyl group and a substituted or unsubstituted 4-carbazolyl group.

The general formula (5) includes a compound having a structure represented by the following general formula (6).

General Formula (6)

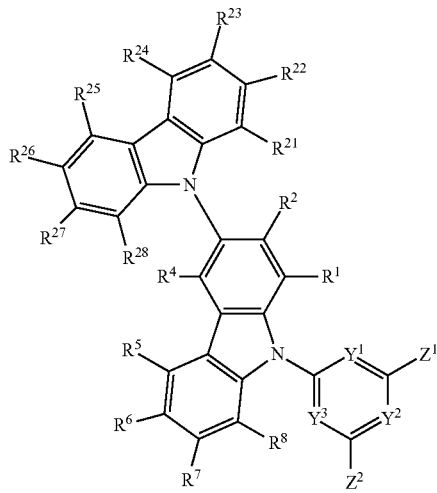

In the general formula (6), any two of $Y^1$, $Y^2$ and $Y^3$ represent nitrogen atoms and the other one thereof represents a methine group, or $Y^1$, $Y^2$ and $Y^3$ all represent nitrogen atoms; $Z^1$ and $Z^2$ each independently represent a hydrogen atom or a substituent; and $R^1$, $R^2$, $R^4$ to $R^8$, and $R^{21}$ to $R^{28}$ each independently represent a hydrogen atom or a substituent.

For the descriptions and the preferred ranges of $Y^1$, $Y^2$, $Y^3$, $Z^1$, $Z^2$, $R^1$, $R^2$ and $R^4$ to $R^8$ in the general formula (6), reference may be made to the corresponding descriptions for the general formula (1). For the descriptions and the preferred ranges of $R^{21}$ to $R^{28}$, reference may be made to the descriptions and the preferred ranges of $R^1$ to $R^8$ in the general formula (1), but it is not necessary that at least one of $R^{21}$ to $R^{28}$ is a substituted or unsubstituted diarylamino group or a substituted or unsubstituted carbazolyl group.

Specific examples of the compound represented by the general formula (1) are shown below. However, the compound represented by the general formula (1) capable of being used in the invention is not construed as being limited to the specific examples.

1

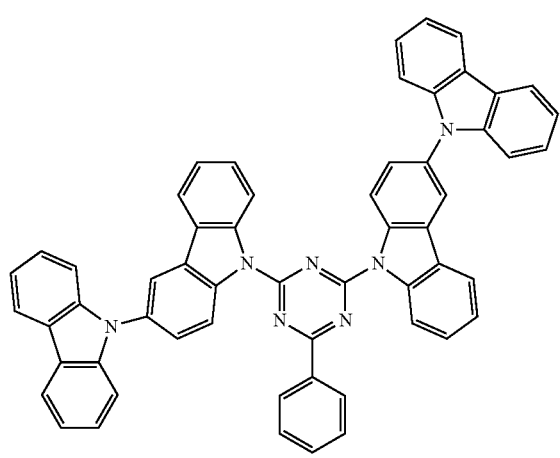

2

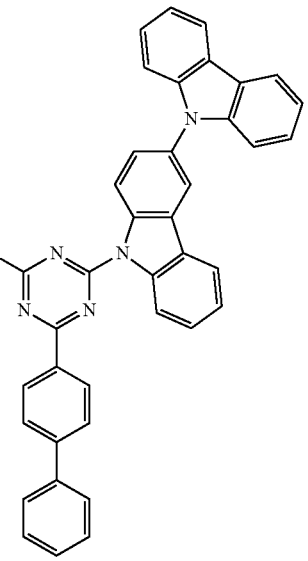

3

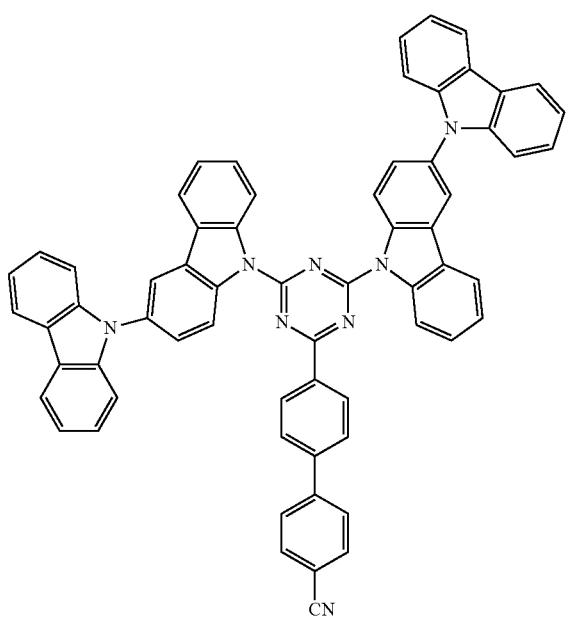

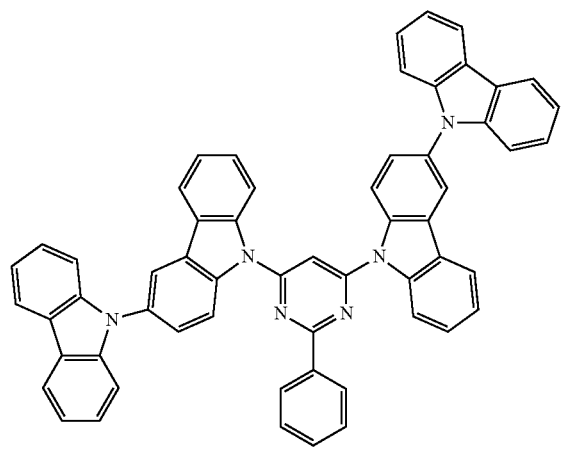
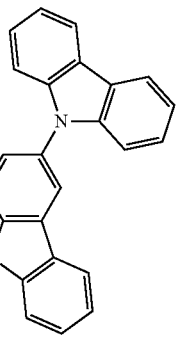
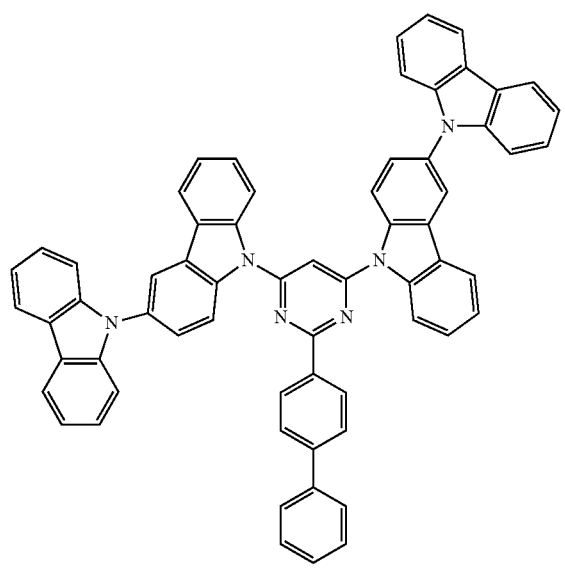
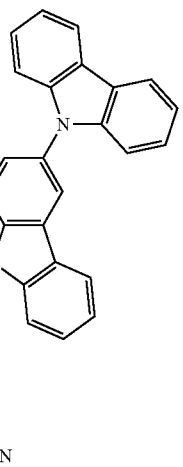
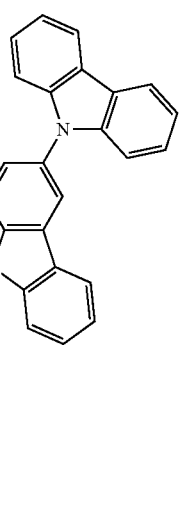

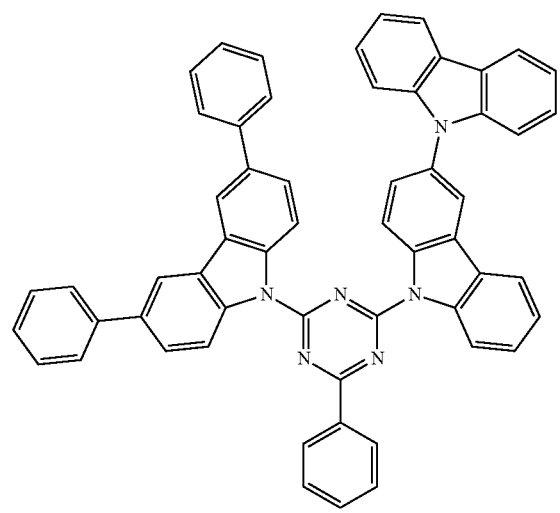
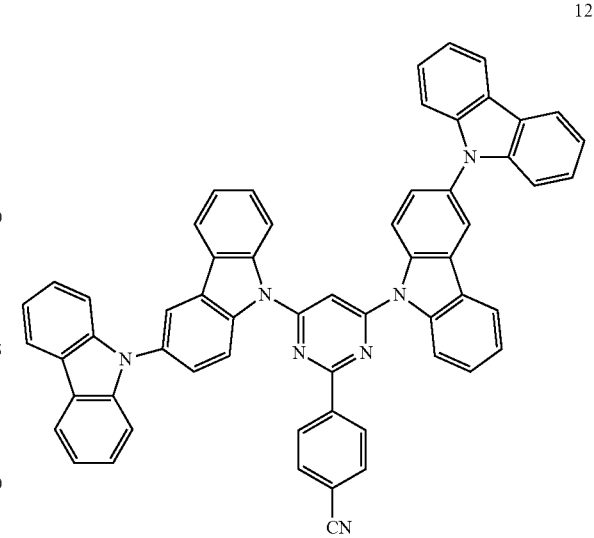
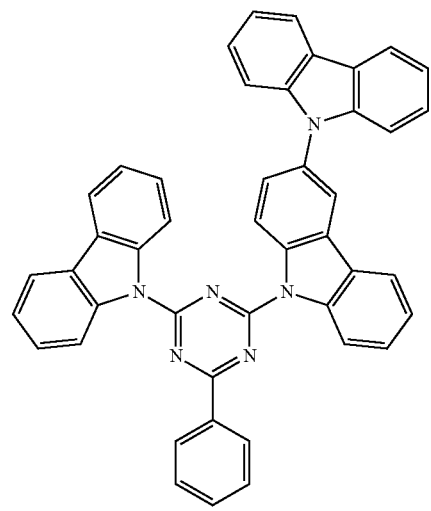
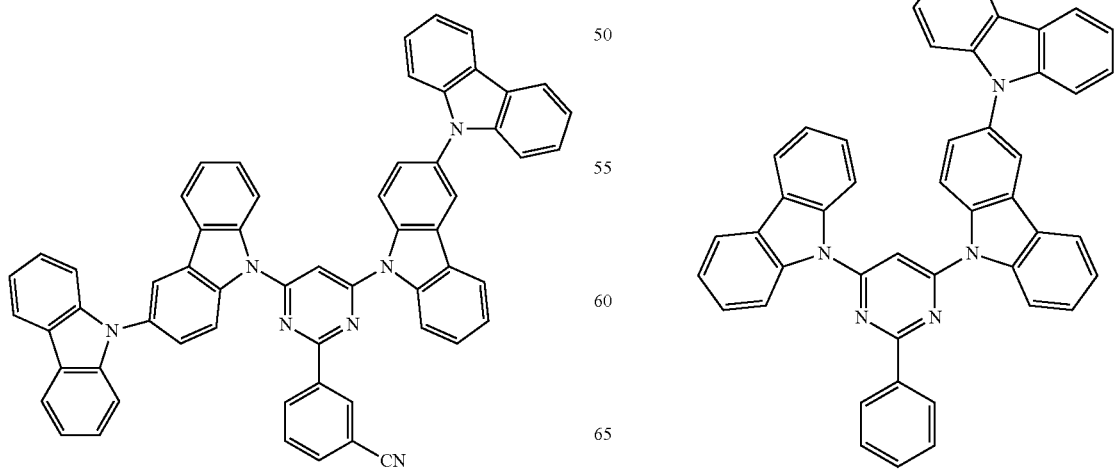

15
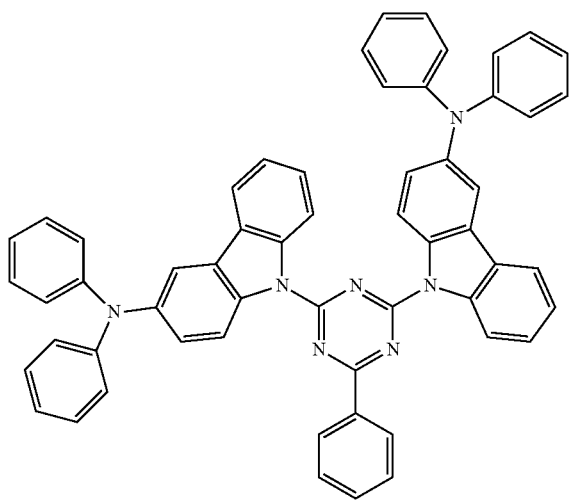
16
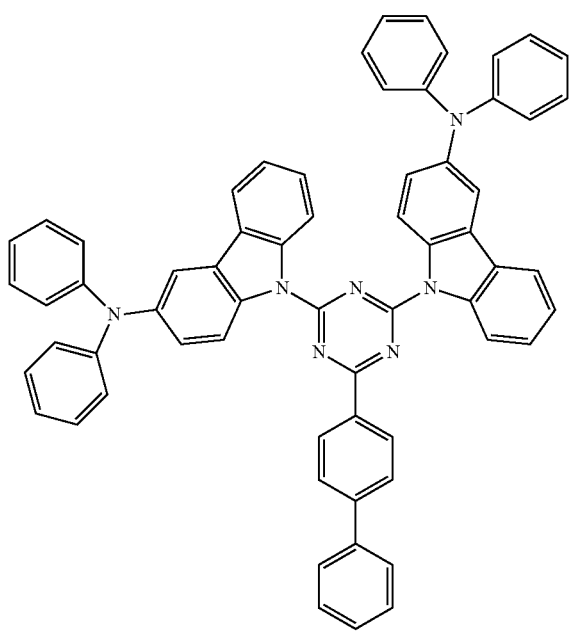
17
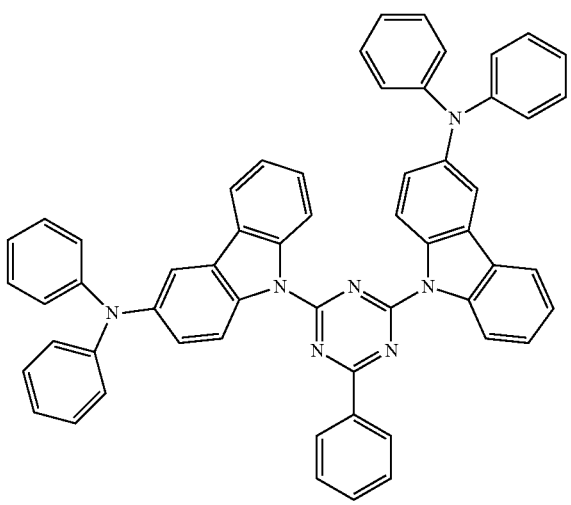
18
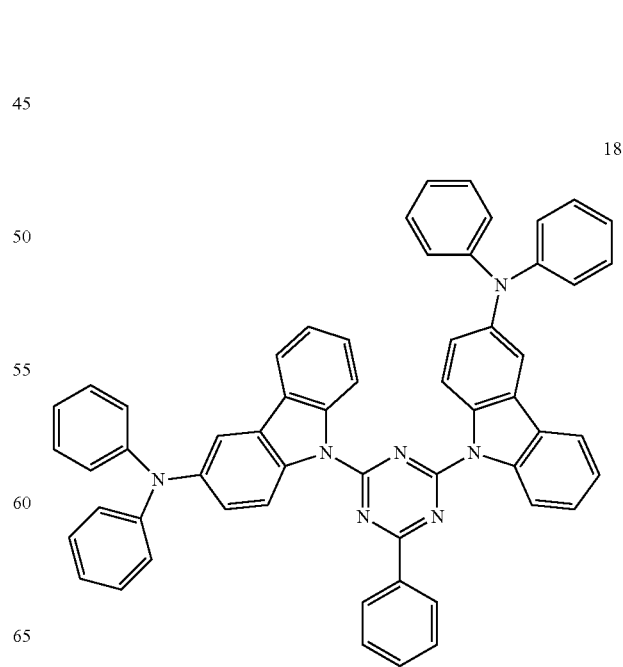

-continued
19
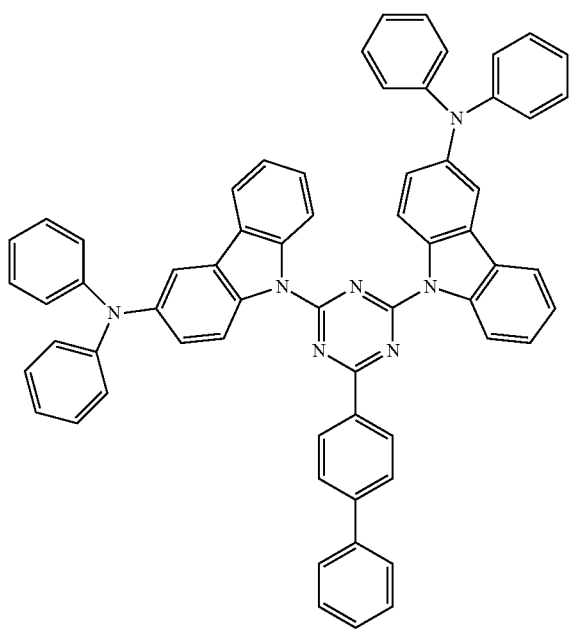
20
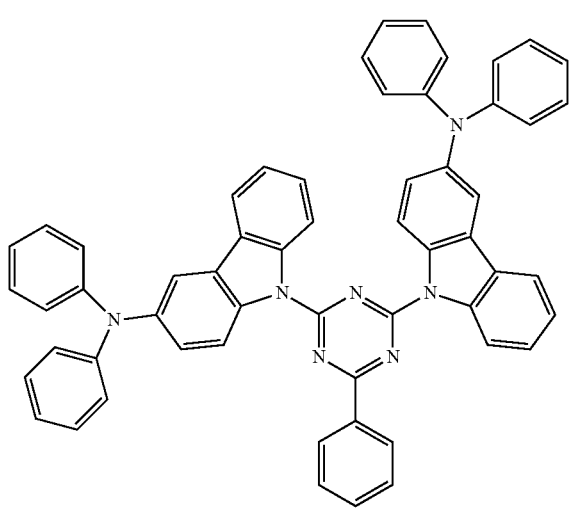
21
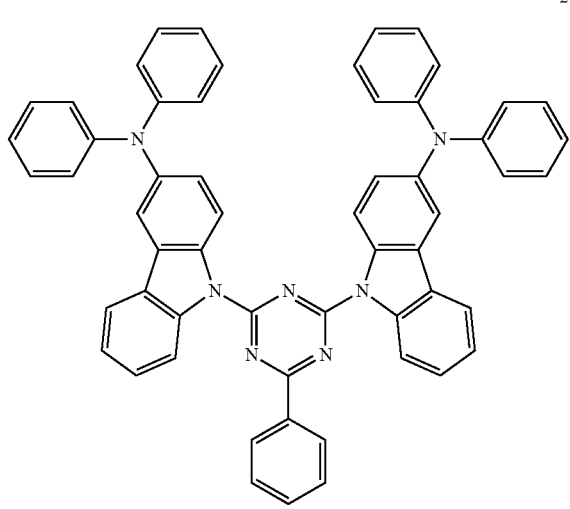
-continued
22
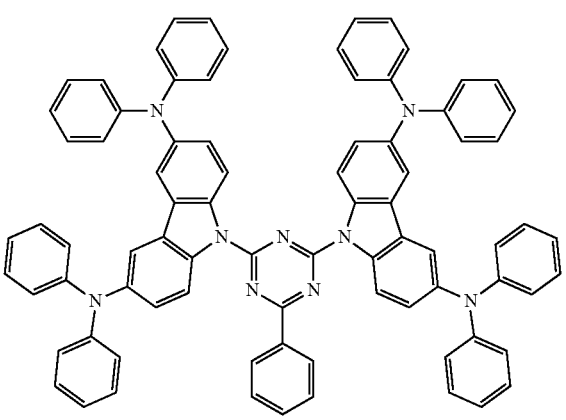
23
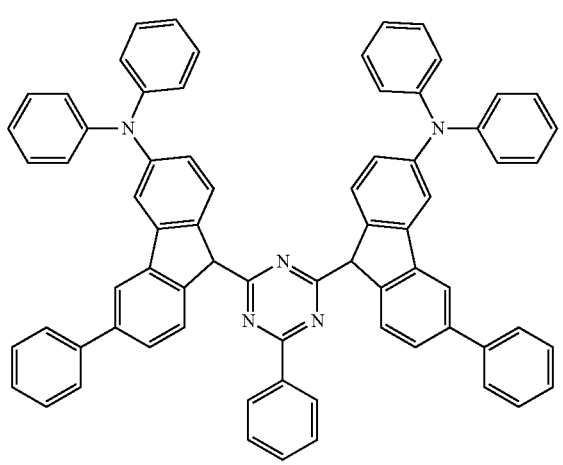
24
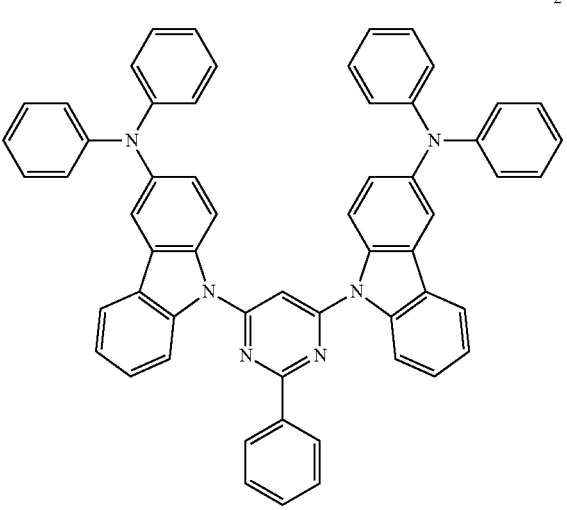

25
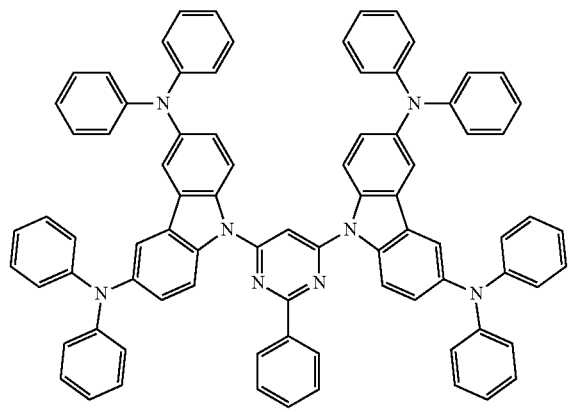
26
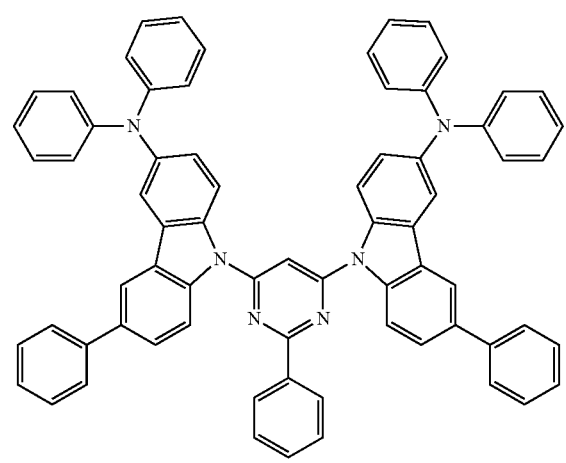
27
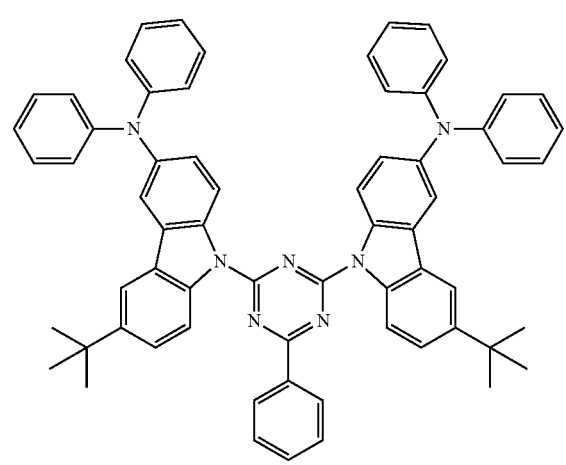
28
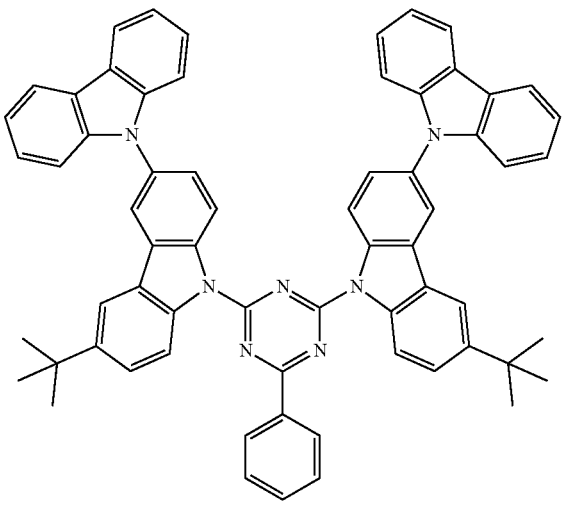
29
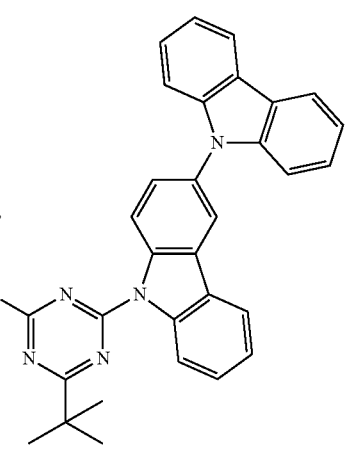
30
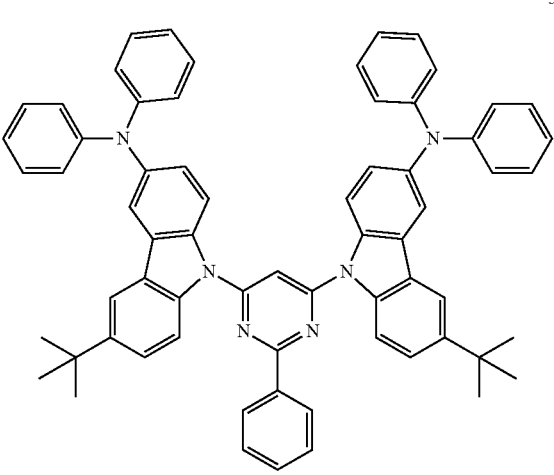

31
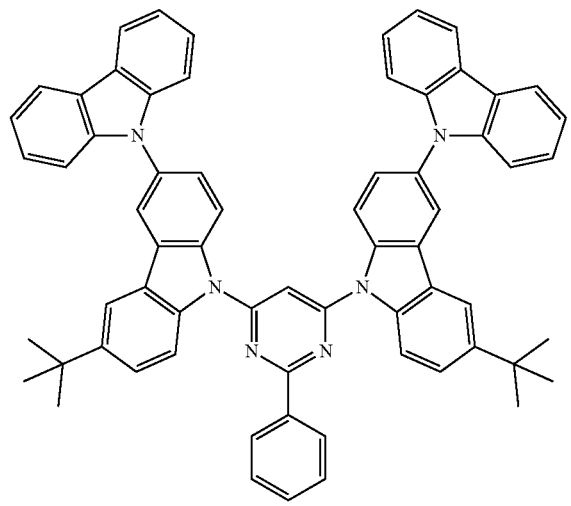
32
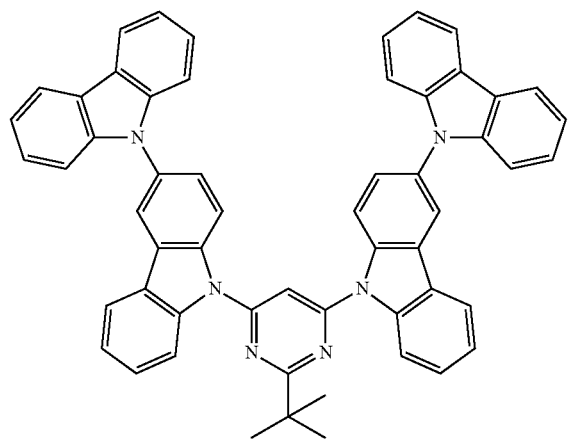
33
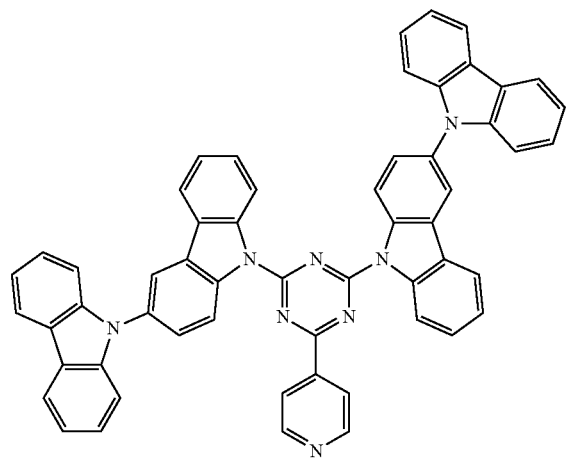
34
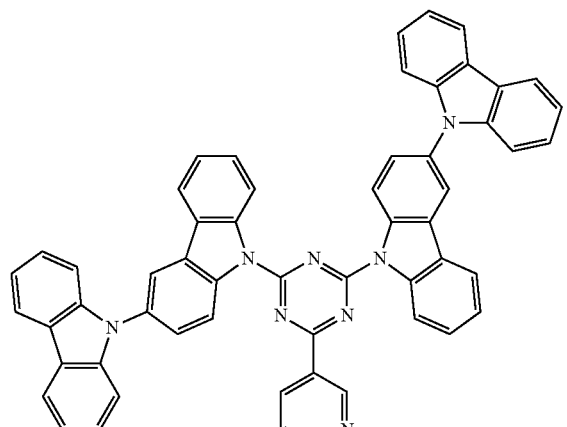
35
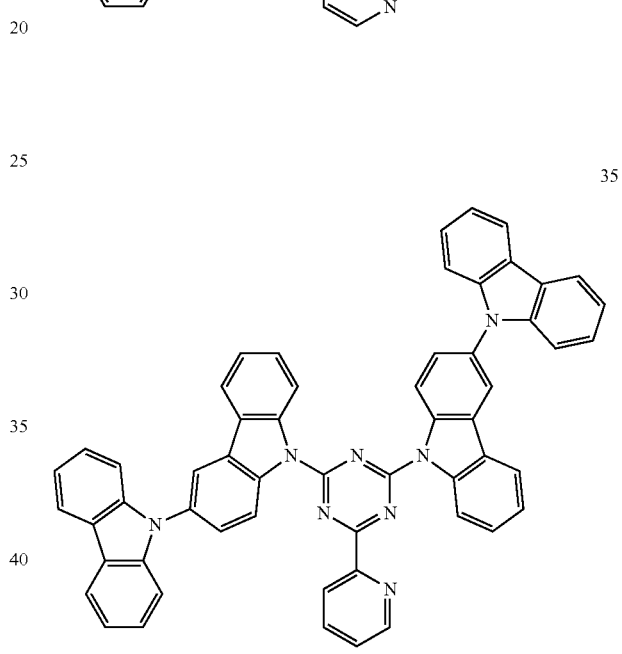
36
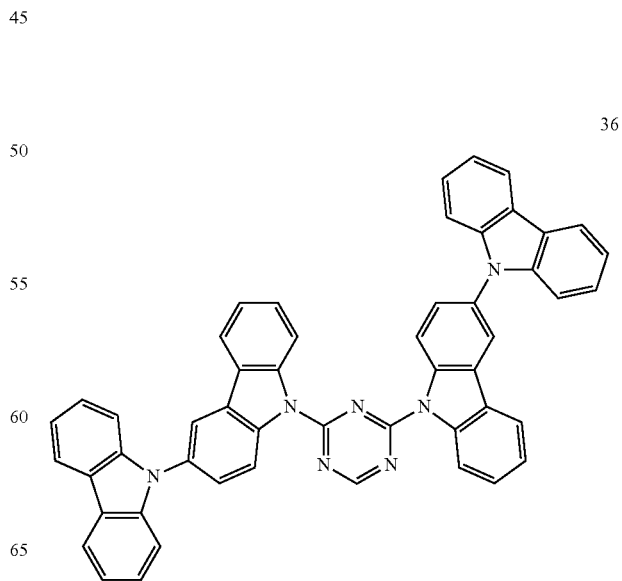

37
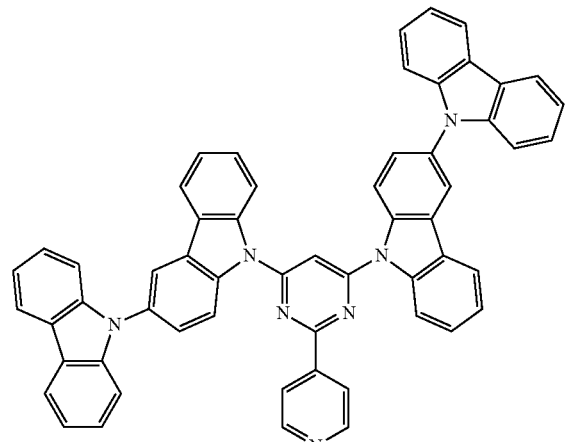
38
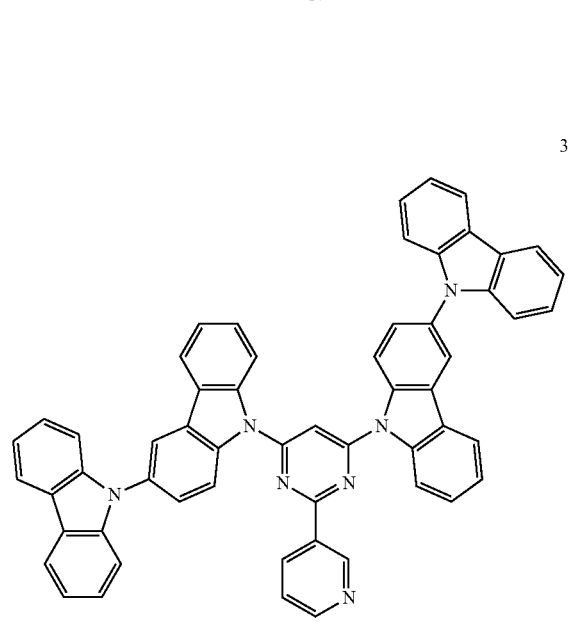
39
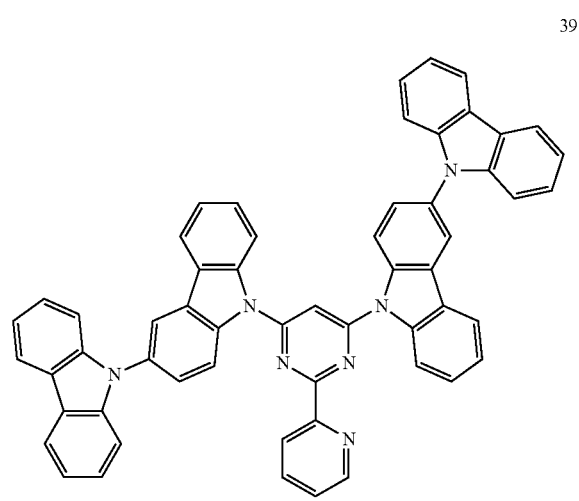
40
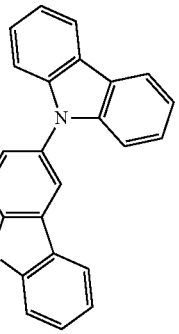
41
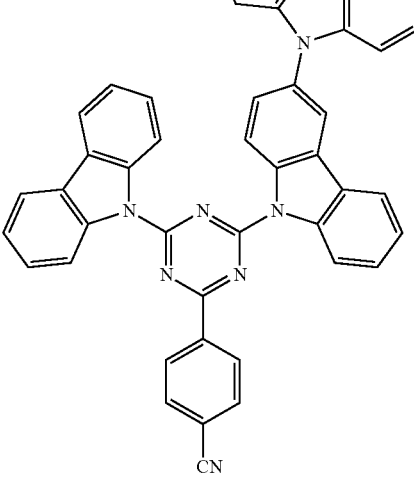
42
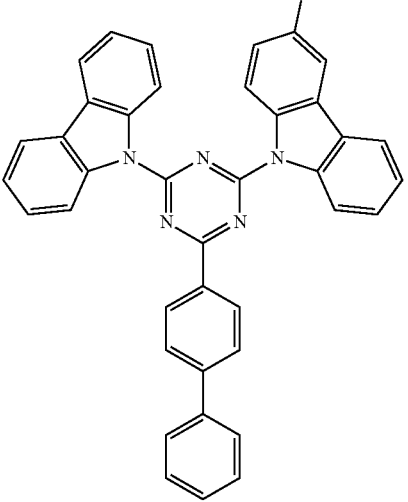

43
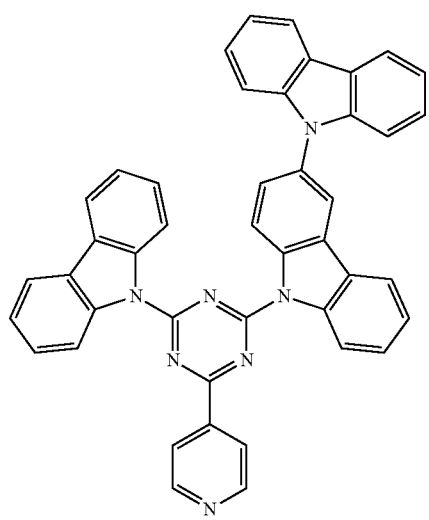
44
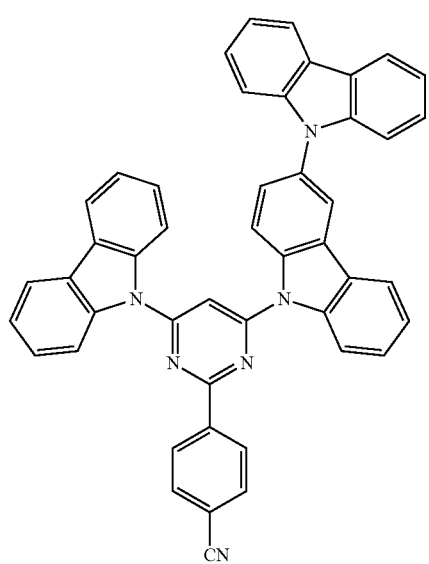
45
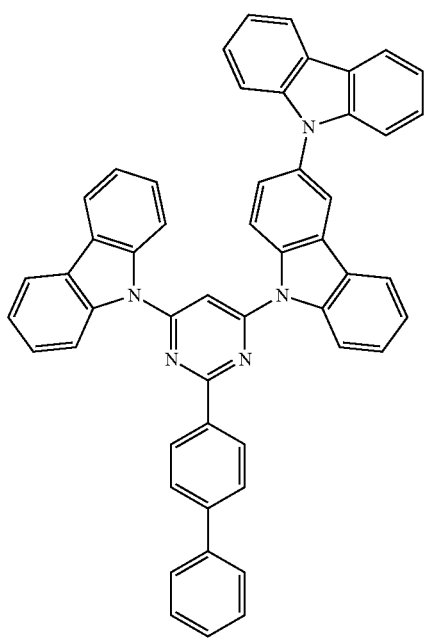
46
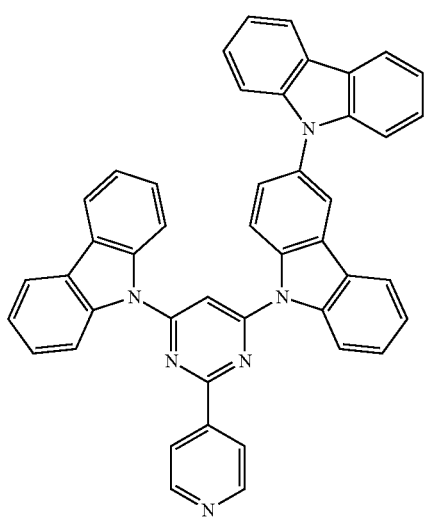

47
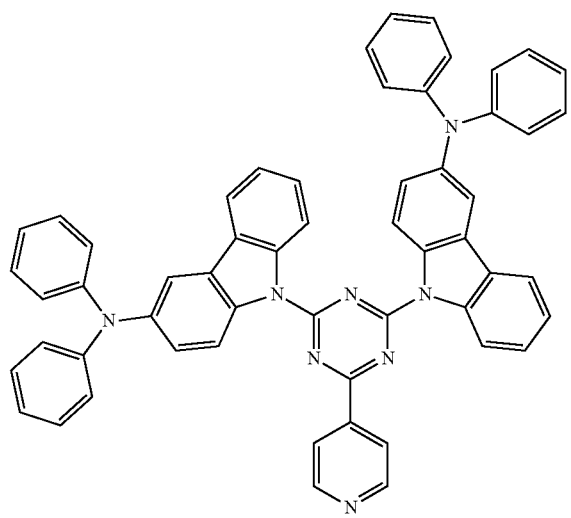
48
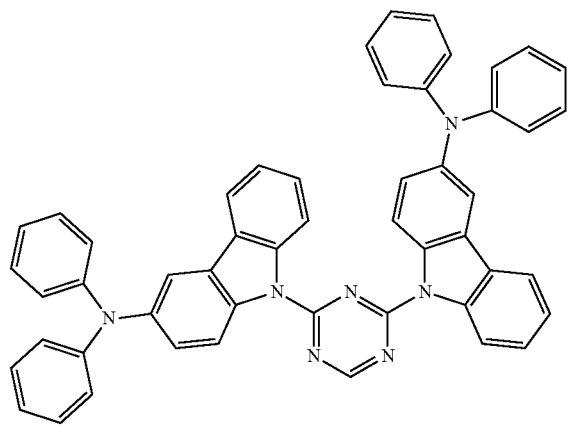
49
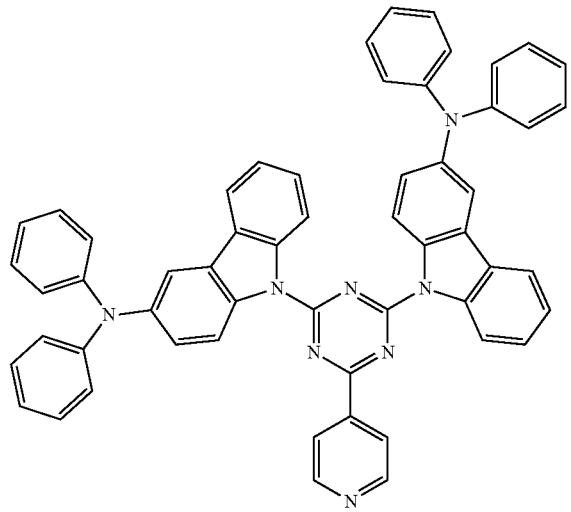
50
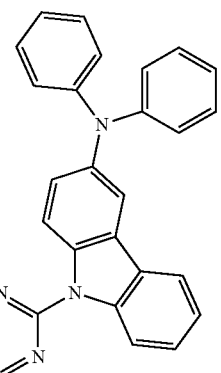
51
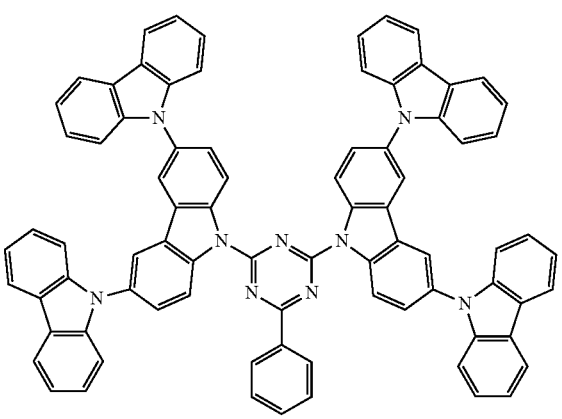
52
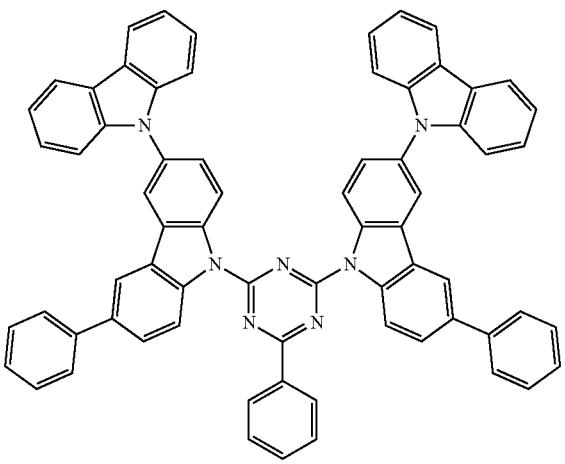

53
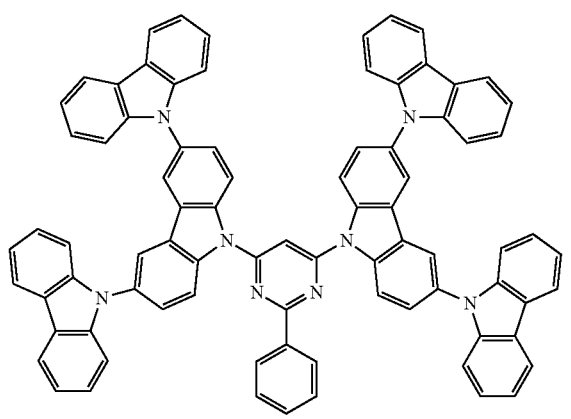
54
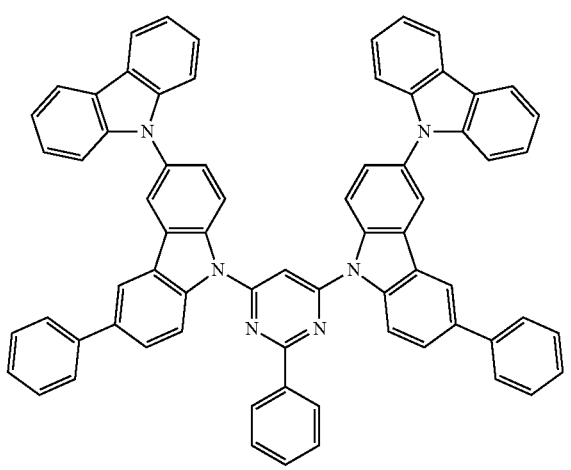
55
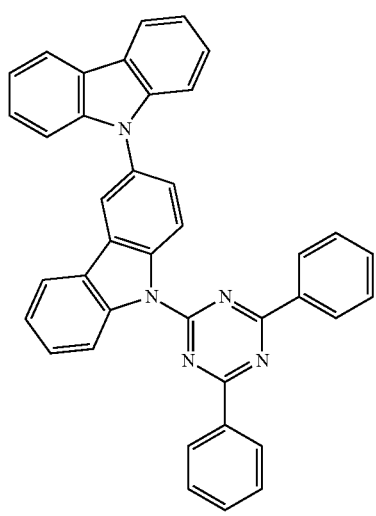
56
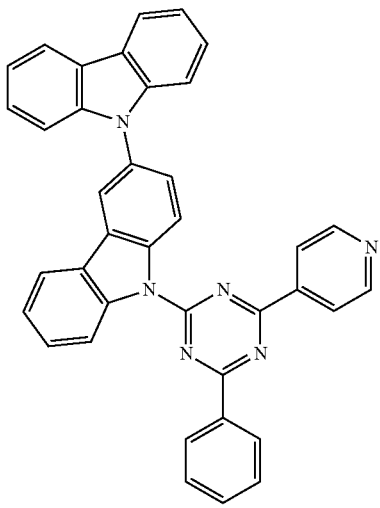
57
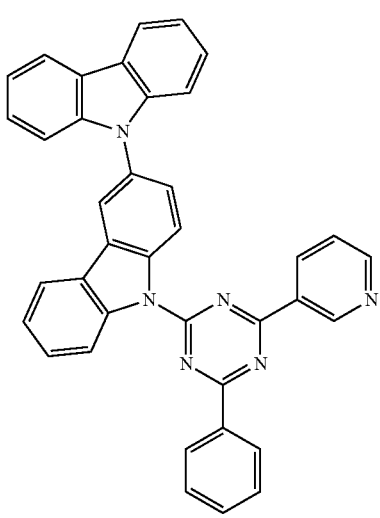
58
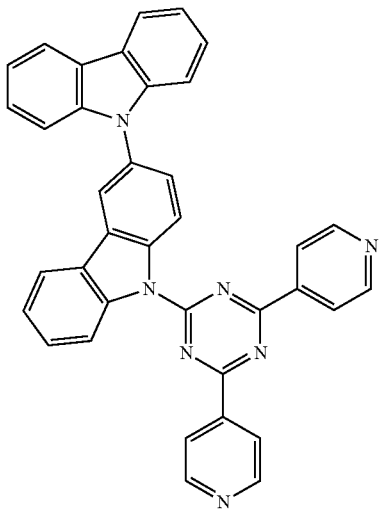

59
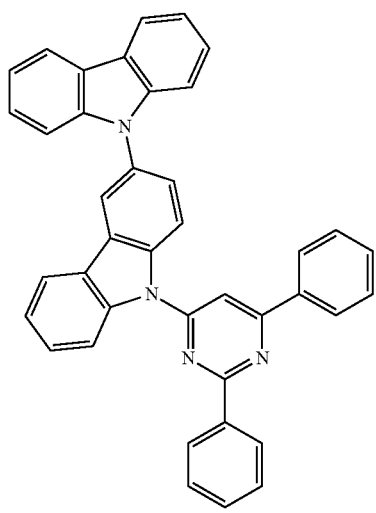
60
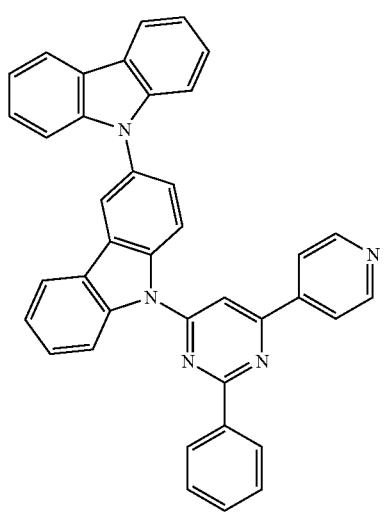
61
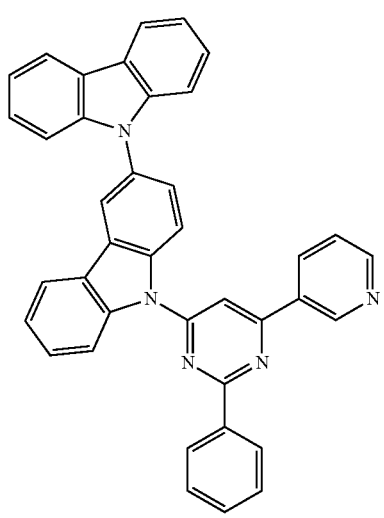
62
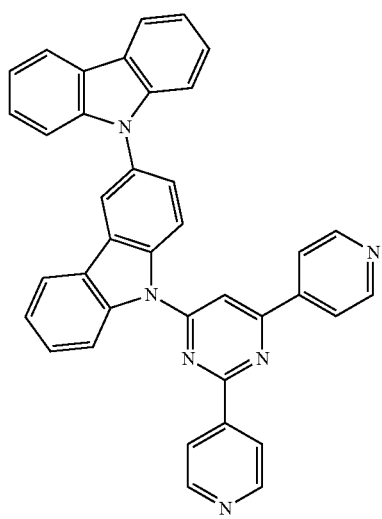
63
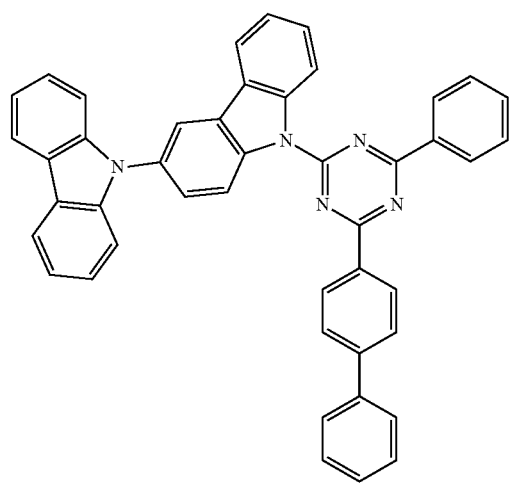
64
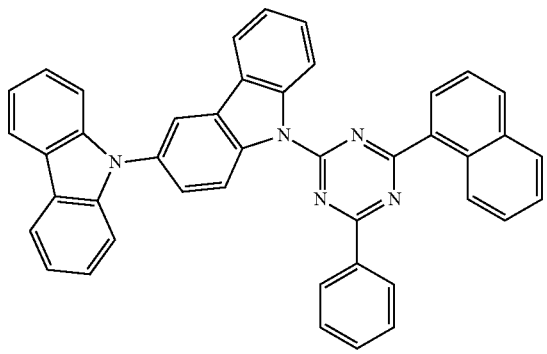

65
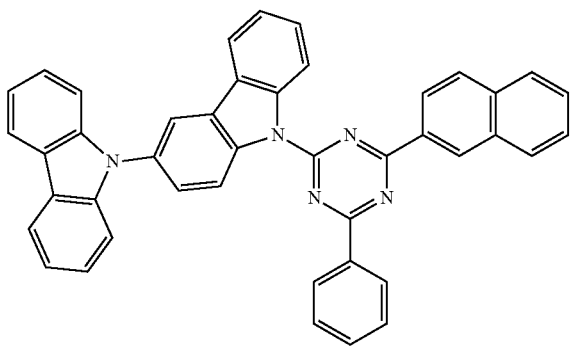
66
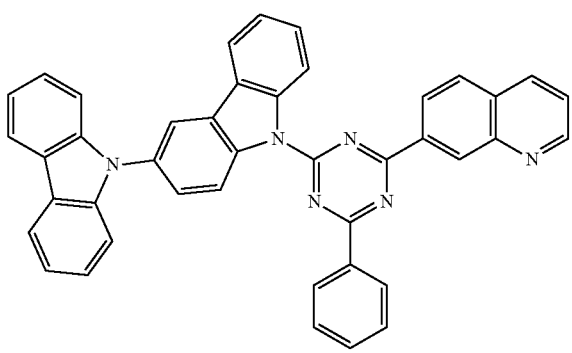
67
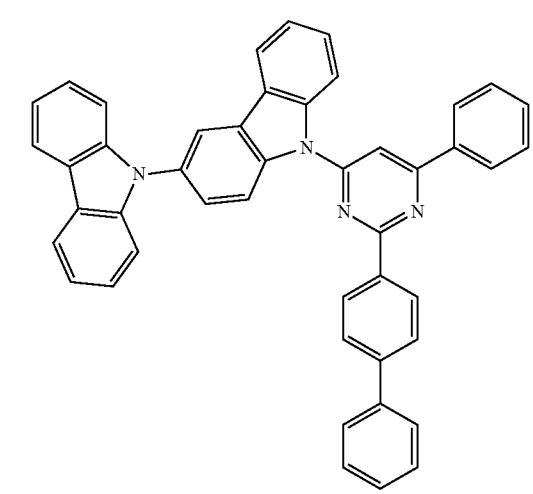
68
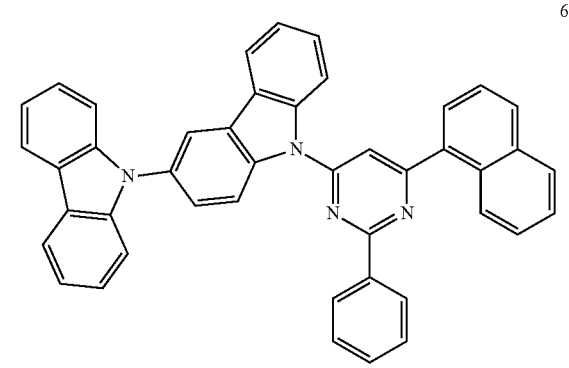
69
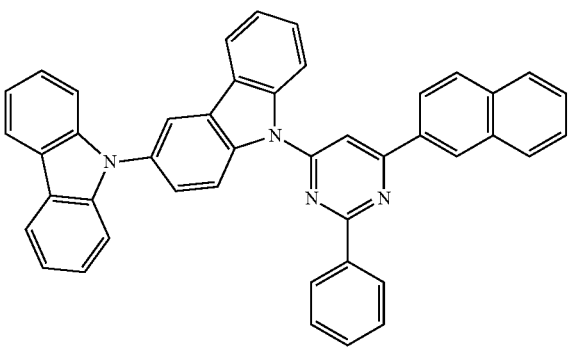
70
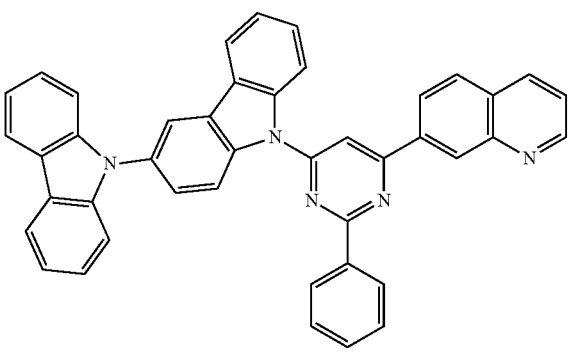
71
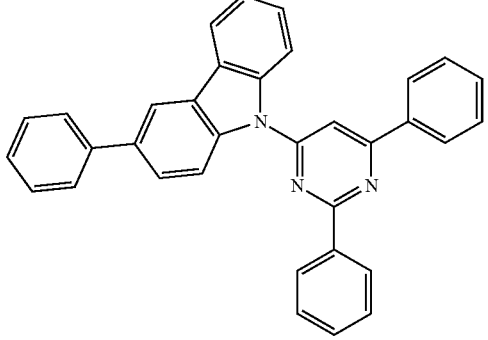

72
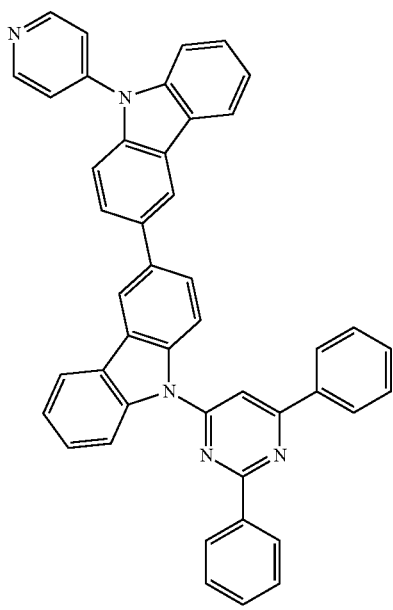
74
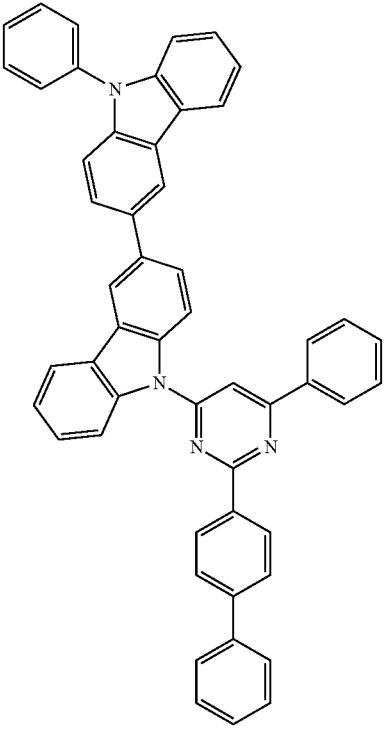
73
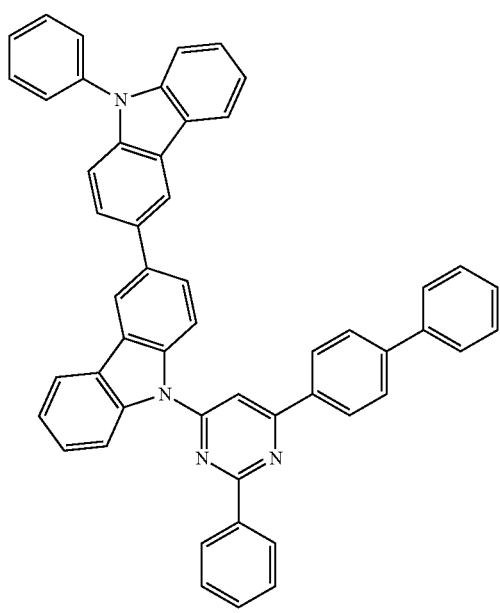
75
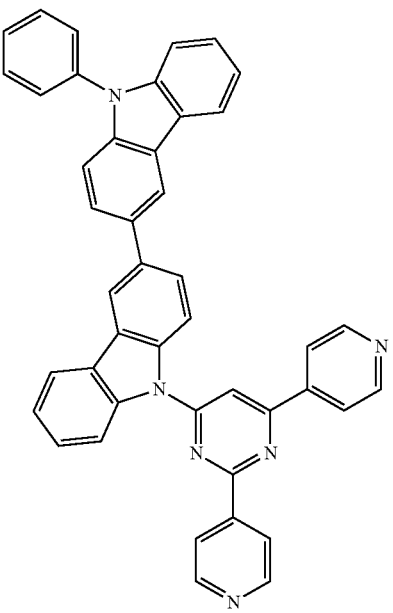

76
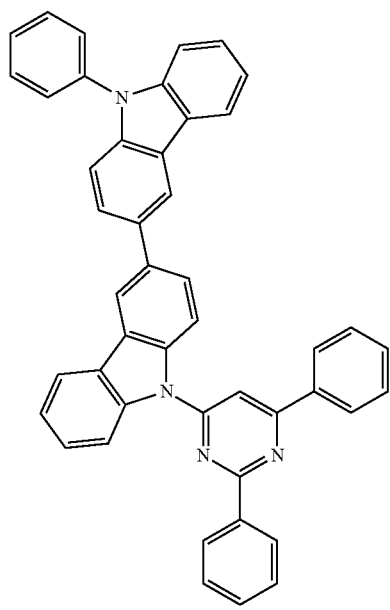
77
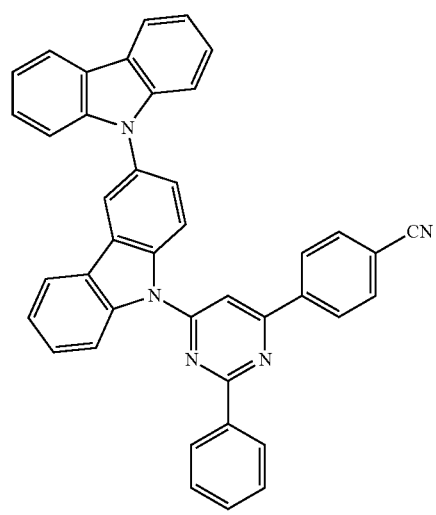
78
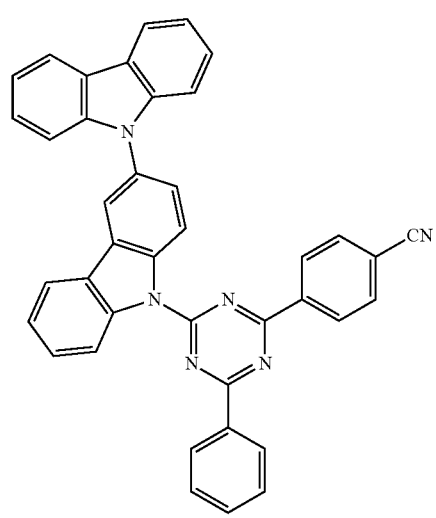
79
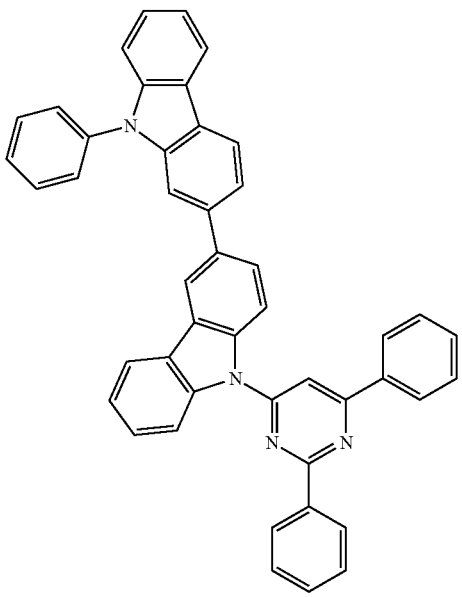
80
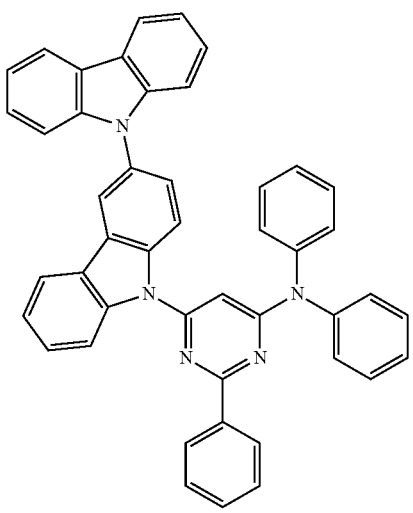
81
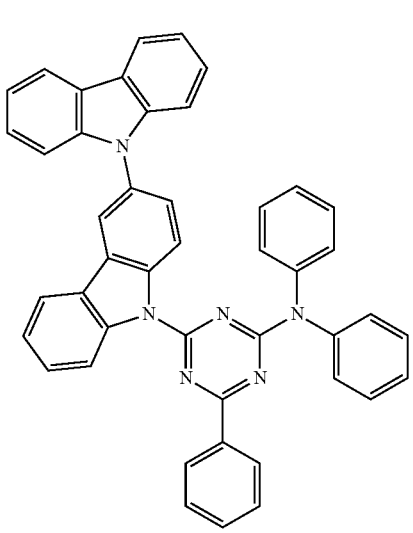

82
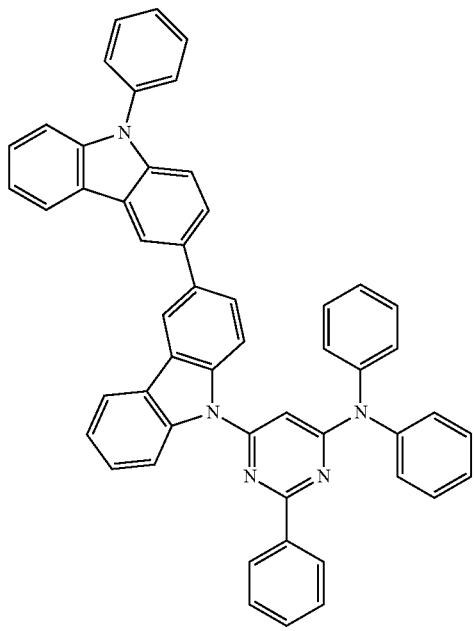
83
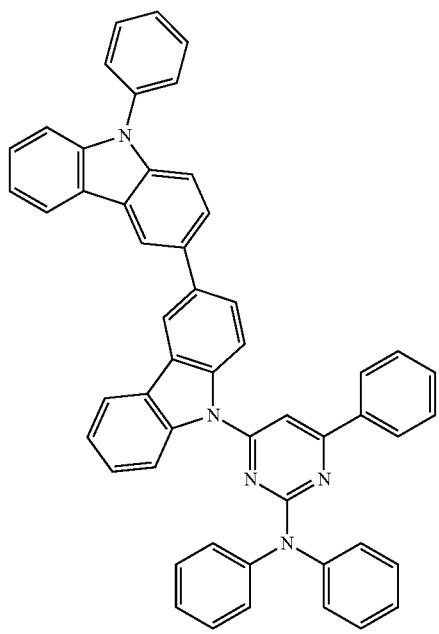
84
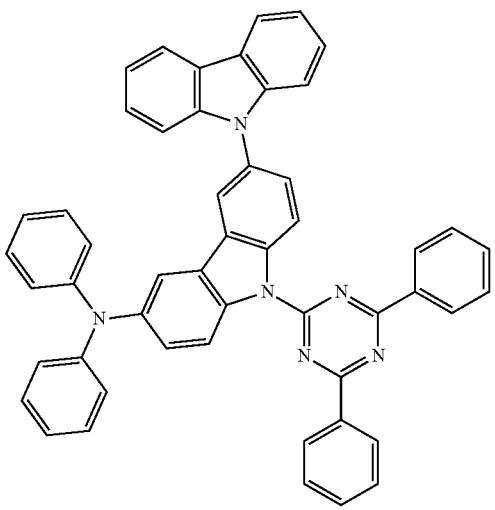
85
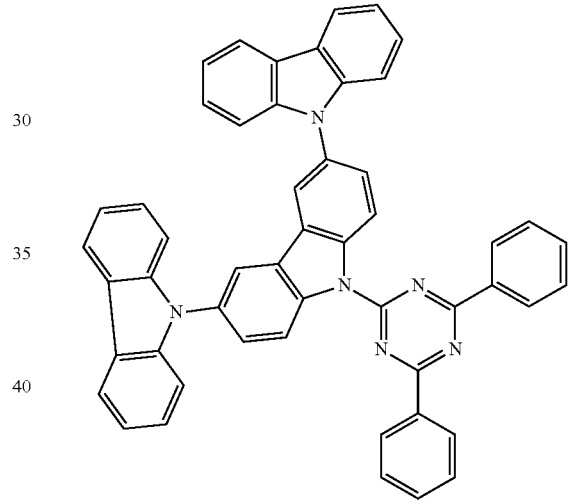
86
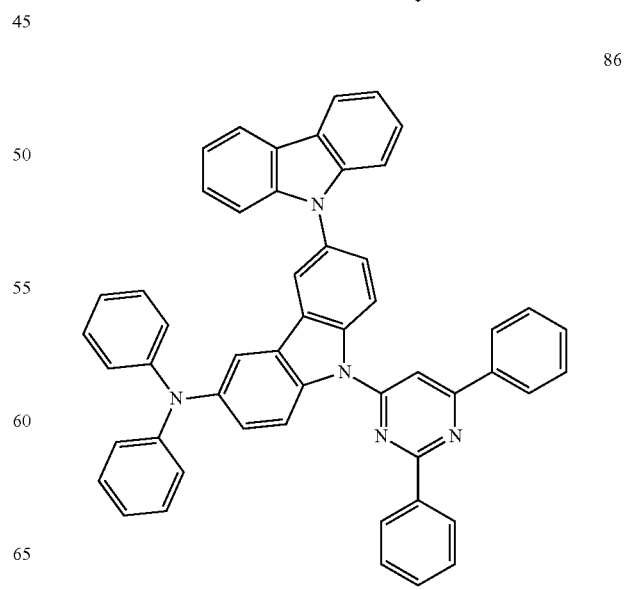

47

-continued

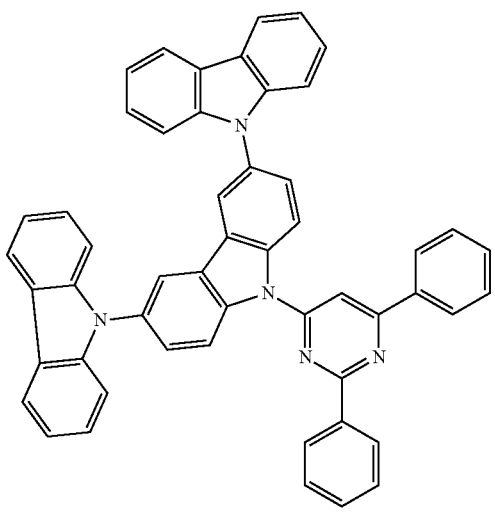
87

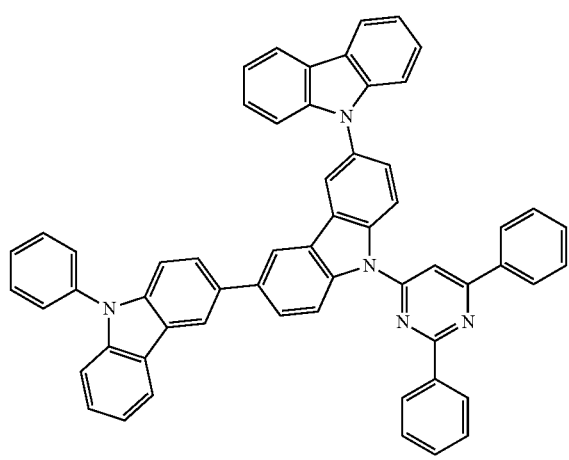
88

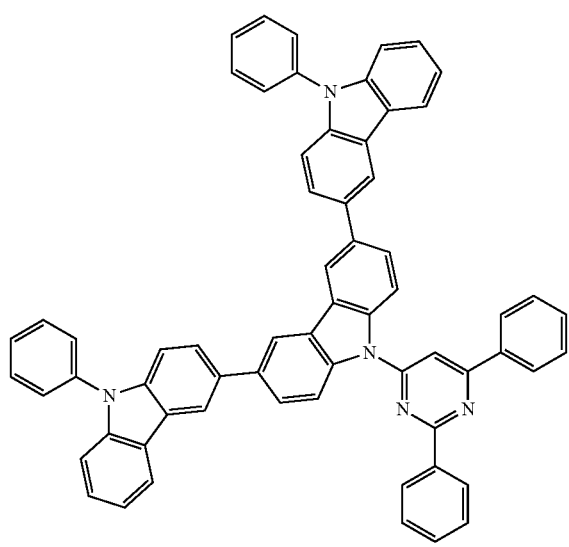
89

Compound having plural structures each represented by the general formula (1) in the molecule thereof is considered to be used in a light-emitting layer of an organic light-emitting device as an application of the invention.

48

For example, it is considered that a polymer formed by polymerizing a polymerizable monomer having a structure represented by the general formula (1) is used in a light-emitting layer of an organic light-emitting device. Specifically, it is considered that a monomer having a polymerizable functional group in any of $R^1$ to $R^8$, $Z^1$ and $Z^2$ is polymerized to provide a polymer having a repeating unit, and the polymer is used in a light-emitting layer of an organic light-emitting device. In alternative, it is considered that compounds each having a structure represented by the general formula (1) are coupled to provide a dimer or a trimer, and they are used in a light-emitting layer of an organic light-emitting device. These applications and modifications may be appropriately made by a skilled person in the art.

Compound Represented by General Formula (11)

Among the compounds represented by the general formula (1), in particular, a compound represented by the following general formula (11) is a novel compound.

General Formula (11)

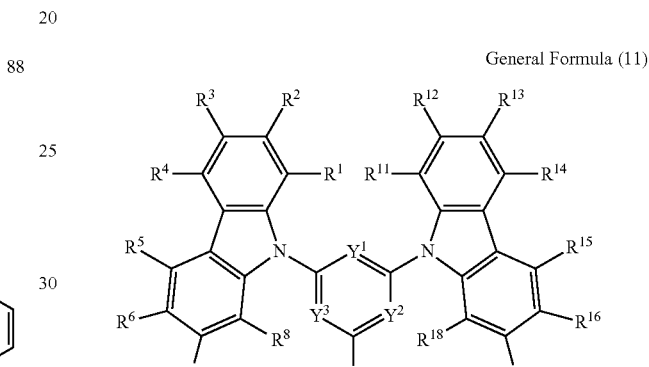

In the general formula (11), any two of $Y^1$, $Y^2$ and $Y^3$ represent nitrogen atoms and the other one thereof represents a methine group, or $Y^1$, $Y^2$ and $Y^3$ all represent nitrogen atoms; $Z^{2'}$ represents a hydrogen atom or a substituent that is bonded via a carbon atom (provided that the substituent does not contain a boron atom); and $R^1$ to $R^8$ and $R^{11}$ to $R^{18}$ each independently represent a hydrogen atom or a substituent, provided that at least one thereof represents a substituted or unsubstituted diarylamino group or a substituted or unsubstituted carbazolyl group.

For the descriptions and the preferred ranges of $Y^1$, $Y^2$, $Y^3$ and $R^1$ to $R^8$ in the general formula (11), reference may be made to the corresponding descriptions for the general formula (1). In the case where any two of $Y^1$, $Y^2$ and $Y^3$ represent nitrogen atoms and the other one thereof represents a methine group, it is most preferred that $Y^1$ is a methine group. For the descriptions and the preferred ranges of $R^{11}$ to $R^{18}$ in the general formula (11), reference may be made to the descriptions and the preferred ranges of $R^1$ to $R^8$ in the general formula (1). However, it is not necessary that at least one of $R^1$ to $R^8$ is a substituted or unsubstituted diarylamino group or a substituted or unsubstituted carbazolyl group, and it is not necessary that at least one of $R^{11}$ to $R^{18}$ is a substituted or unsubstituted diarylamino group or a substituted or unsubstituted carbazolyl group. The substituent that is bonded via a carbon atom that is capable of being represented by $Z^{2'}$ means a substituent that is bonded to the triazine ring or the pyrimidine ring of the general formula (11) via a carbon atom. Examples thereof include a substituted or unsubstituted alkyl group, a substituted or unsubstituted alkoxy group, a substituted or unsubstituted aryl group, a substituted or unsubstituted heteroaryl group (which is limited to a group that is bonded via a carbon atom), a substituted or unsubstituted alkenyl group, a substituted or unsubstituted alkynyl group, a substituted or unsubstituted haloalkyl group, a substituted or unsubstituted trialkylsilylalkyl group, a substituted or unsubstituted trialkylsilylalkenyl group, a substituted or unsubstituted trialkylsilylalkynyl group and a cyano group. More preferred examples thereof include a substituted or unsubstituted alkyl group having from 1 to 20 carbon atoms, a substituted or unsubstituted alkoxy group having from 1 to 20 carbon atoms, a substituted or unsubstituted aryl group having from 6 to 40 carbon atoms, a substituted or unsubstituted heteroaryl group having from 3 to 40 carbon atoms (which is limited to a group that is bonded via a carbon atom), a substituted or unsubstituted alkenyl group having from 2 to 10 carbon atoms, a substituted or unsubstituted alkynyl group having from 2 to 10 carbon atoms, a substituted or unsubstituted haloalkyl group having from 1 to 10 carbon atoms, a substituted or unsubstituted trialkylsilylalkyl group having from 4 to 20 carbon atoms, a substituted or unsubstituted trialkylsilylalkenyl group having from 5 to 20 carbon atoms, a substituted or unsubstituted trialkylsilylalkynyl group having from 5 to 20 carbon atoms and a cyano group. Further preferred examples thereof include a substituted or unsubstituted alkyl group having from 1 to 20 carbon atoms, a substituted or unsubstituted aryl group having from 6 to 40 carbon atoms and a substituted or unsubstituted heteroaryl group having from 3 to 40 carbon atoms (which is limited to a group that is bonded via a carbon atom).

The compound represented by the general formula (11) is preferably a compound having a structure represented by the following general formula (12).

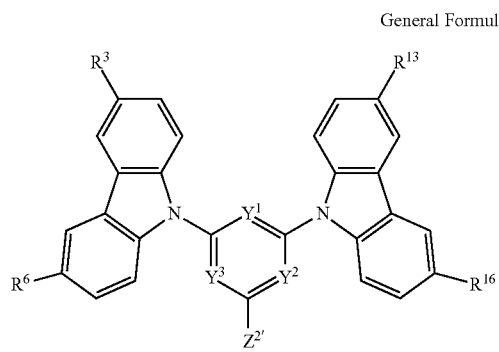

General Formula (12)

In the general formula (12), any two of $Y^1$, $Y^2$ and $Y^3$ represent nitrogen atoms and the other one thereof represents a methine group, or $Y^1$, $Y^2$ and $Y^3$ all represent nitrogen atoms; $Z^{2'}$ represents a hydrogen atom, a substituted or unsubstituted alkyl group, a substituted or unsubstituted alkoxy group, a substituted or unsubstituted aryl group, a substituted or unsubstituted heteroaryl group (which is limited to a group that is bonded via a carbon atom), a substituted or unsubstituted alkenyl group, a substituted or unsubstituted alkynyl group, a substituted or unsubstituted haloalkyl group, a substituted or unsubstituted trialkylsilylalkyl group, a substituted or unsubstituted trialkylsilylalkenyl group, a substituted or unsubstituted trialkylsilylalkynyl group or a cyano group; and $R^3$, $R^6$, $R^{13}$ and $R^{16}$ each independently represent a hydrogen atom or a substituent, provided that at least one thereof represents a substituted or unsubstituted diarylamino group or a substituted or unsubstituted carbazolyl group. For the preferred ranges of $Z^v$, $R^3$, $R^6$, $R^{13}$ and $R^{16}$, reference may be made to the corresponding descriptions for the general formula (11).

Synthesis Method of Compound Represented by General Formula (11)

The synthesis method of the compound represented by the general formula (11) is not particularly limited. The compound represented by the general formula (11) may be synthesized by appropriately combining known synthesis methods and conditions.

For example, examples of a preferred synthesis method include a method in which a compound represented by the following general formula (21) is reacted with a compound represented by the following general formula (22) and a compound represented by the following general formula (23) to synthesize a compound represented by the following general formula (24), which is further reacted with a compound represented by the following general formula (25).

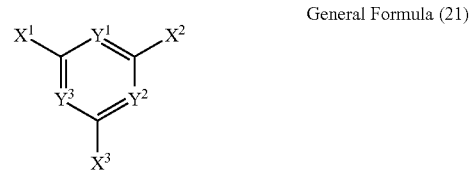

General Formula (21)

In the general formula (21), any two of $Y^1$, $Y^2$ and $Y^3$ represent nitrogen atoms and the other one thereof represents a methine group, or $Y^1$, $Y^2$ and $Y^3$ all represent nitrogen atoms; and $X^1$, $X^2$ and $X^3$ each independently represent a halogen atom. Examples of the halogen atom include a fluorine atom, a chlorine atom, a bromine atom and an iodine atom. $X^1$, $X^2$ and $X^3$ may be the same as or different from each other, and may be appropriately determined in consideration of the reactivity with the compounds represented by the general formulae (22), (23) and (25), and the like.

In the general formulae (22) to (25), the definitions of $Y^1$, $Y^2$, $Y^3$, $Z^{2'}$, $R^1$ to $R^8$ and $R^{11}$ to $R^{18}$ are the same as the corresponding definitions in the general formula (11), and the definitions of $X^1$, $X^2$ and $X^3$ in the general formulae (22) to (25) are the same as the corresponding definitions in the general formula (21).

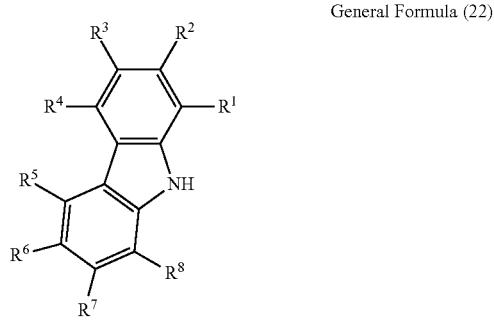

General Formula (22)

General Formula (23)

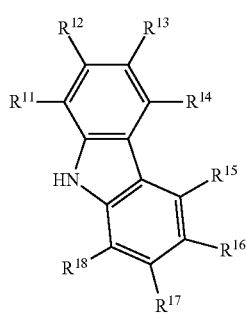

General Formula (25)

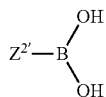

The reaction between the compound represented by the general formula (21) and the compound represented by the general formula (22) may be performed under ordinary coupling reaction conditions. For example, n-butyllithium may be added to a tetrahydrofuran solution of the compound represented by the general formula (22) and reacted therewith, and then the solution may be added dropwise to a tetrahydrofuran solution of the compound of the general formula (21) to perform a coupling reaction. The coupling reaction between the compound thus formed and the compound represented by the general formula (23) may be performed similarly. In the reaction, such a method may be performed that a mixed tetrahydrofuran solution of the compound represented by the general formula (22) and the compound represented by the general formula (23) is prepared firstly, n-butyllithium is added to the mixed solution and reacted therewith, and then the mixed solution is added dropwise to a tetrahydrofuran solution of the compound of the general formula (21) to perform a coupling reaction. A compound represented by the following general formula (24) may be obtained by a known purification method from the mixture obtained after the coupling reaction.

General Formula (24)

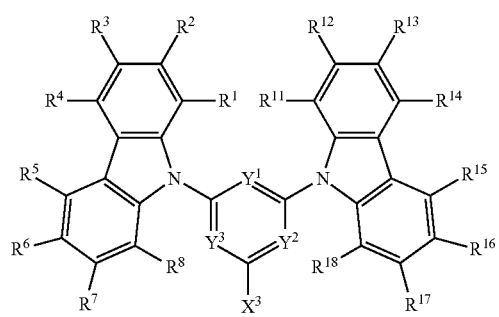

The compound represented by the general formula (24) may be further reacted with a compound represented by the following general formula (25), thereby synthesizing the compound represented by the general formula (11). The reaction is a known reaction, and known reaction conditions may be appropriately selected and used.

For the details of the reaction mentioned above, reference may be made to Synthesis Examples described later. The compound represented by the general formula (11) may also be synthesized by combining other known synthesis reactions.

Organic Light-Emitting Device

The compound represented by the general formula (1) of the invention is useful as a light-emitting material of an organic light-emitting device. The compound represented by the general formula (1) of the invention is capable of exhibiting usefulness thereof as a delayed fluorescent material emitting delayed fluorescent light. Accordingly, an organic light-emitting device that uses the compound represented by the general formula (1) as a light-emitting material thus has features that the device emits delayed fluorescent light and has a high light emission efficiency. The principle of the features may be described as follows for an organic electroluminescent device as an example.

In an organic electroluminescent device, carriers injected from an anode and a cathode form an excited state for the light-emitting material, from which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that excitons excited in the triplet state, which can be formed directly in that state or indirectly processes such as intersystem crossing from a singlet state, transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light after reverse intersystem crossing to the excited singlet state by absorbing the heat generated by the device. At this time, the light emitted after reverse intersystem crossing from the excited triplet state to the excited singlet state has the same wavelength as fluorescent light since it is light emission from the excited single state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited single state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layers in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of, as an electrode material, a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 µm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of, as an electrode material, a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 µm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where a host material is used, the amount of the compound of the invention contained in the light-emitting layer as the light-emitting material is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from diffusing outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has lowest excited singlet energy and lowest excited triplet energy, at least one of which is higher than the lowest excited singlet energy and the lowest excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light-emitting layer but also in layers other than the light-emitting layer. In this case, the compound represented by the general formula (1) used in the light-emitting layer and the compound represented by the general formula (1) used in the layers other than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R, R' and $R_1$ to $R_{10}$ each independently represent a hydrogen atom or a substituent; X represents a carbon atom or a heteroatom that forms a cyclic structure; n represents an integer of from 3 to 5; Y represents a substituent; and m represents an integer of 0 or more.

Preferred examples of a compound that may also be used as the host material of the light-emitting layer are shown below.

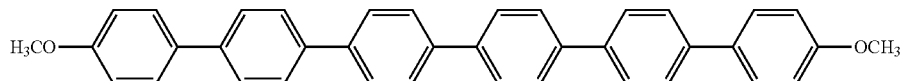
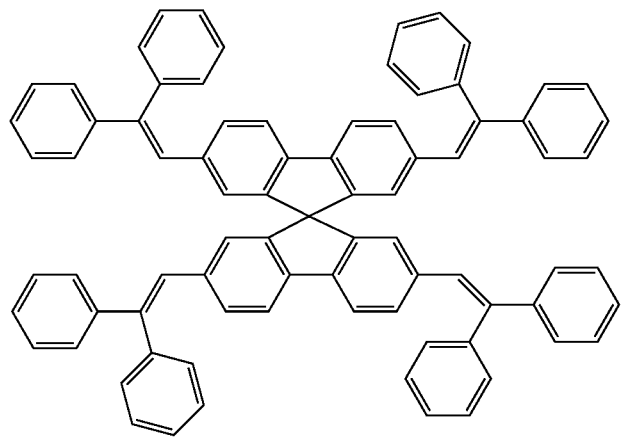
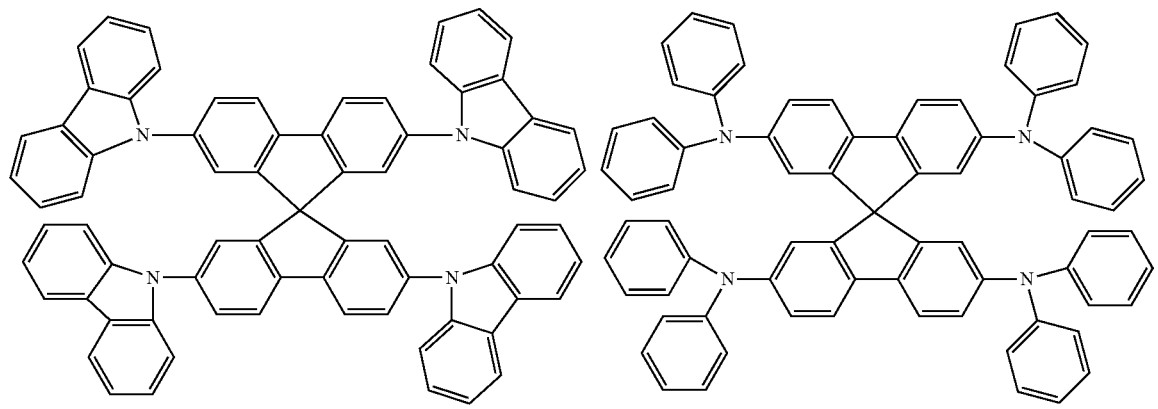

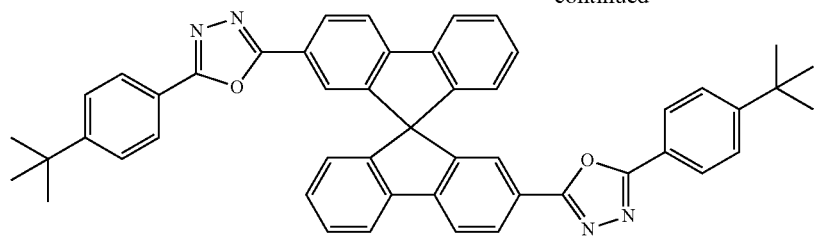
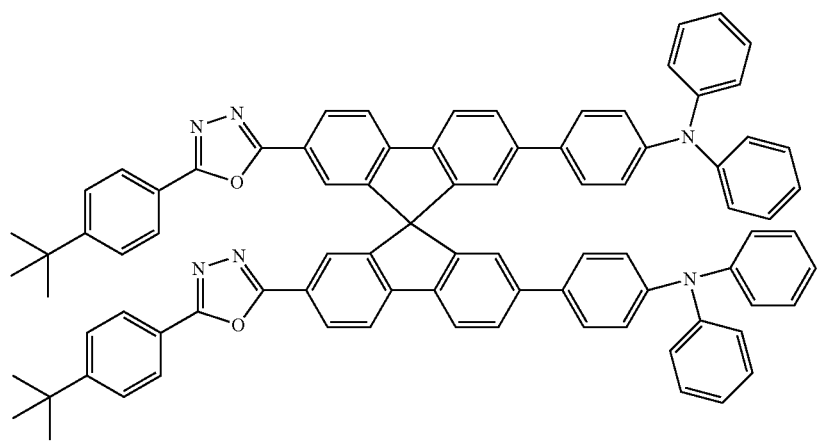
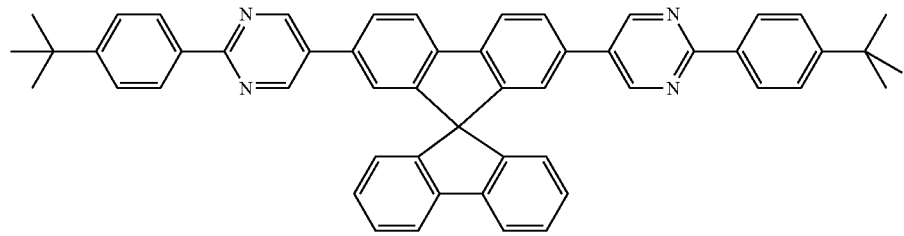
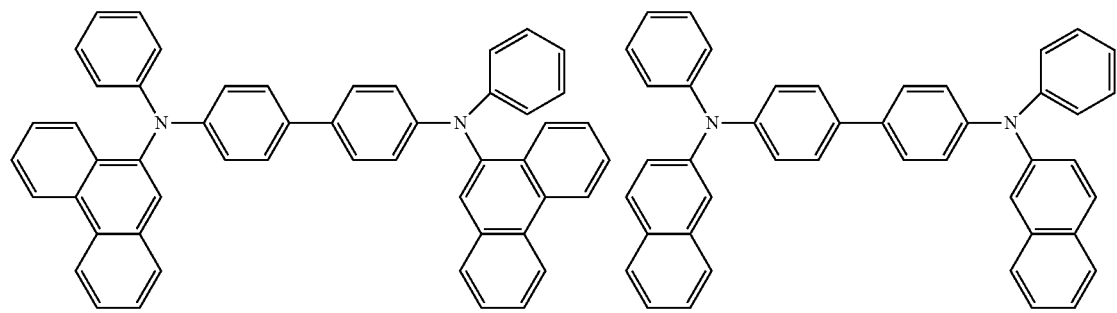
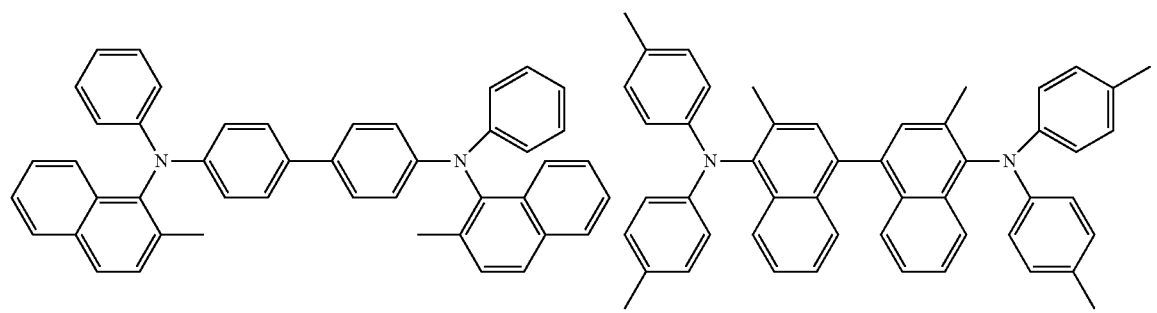

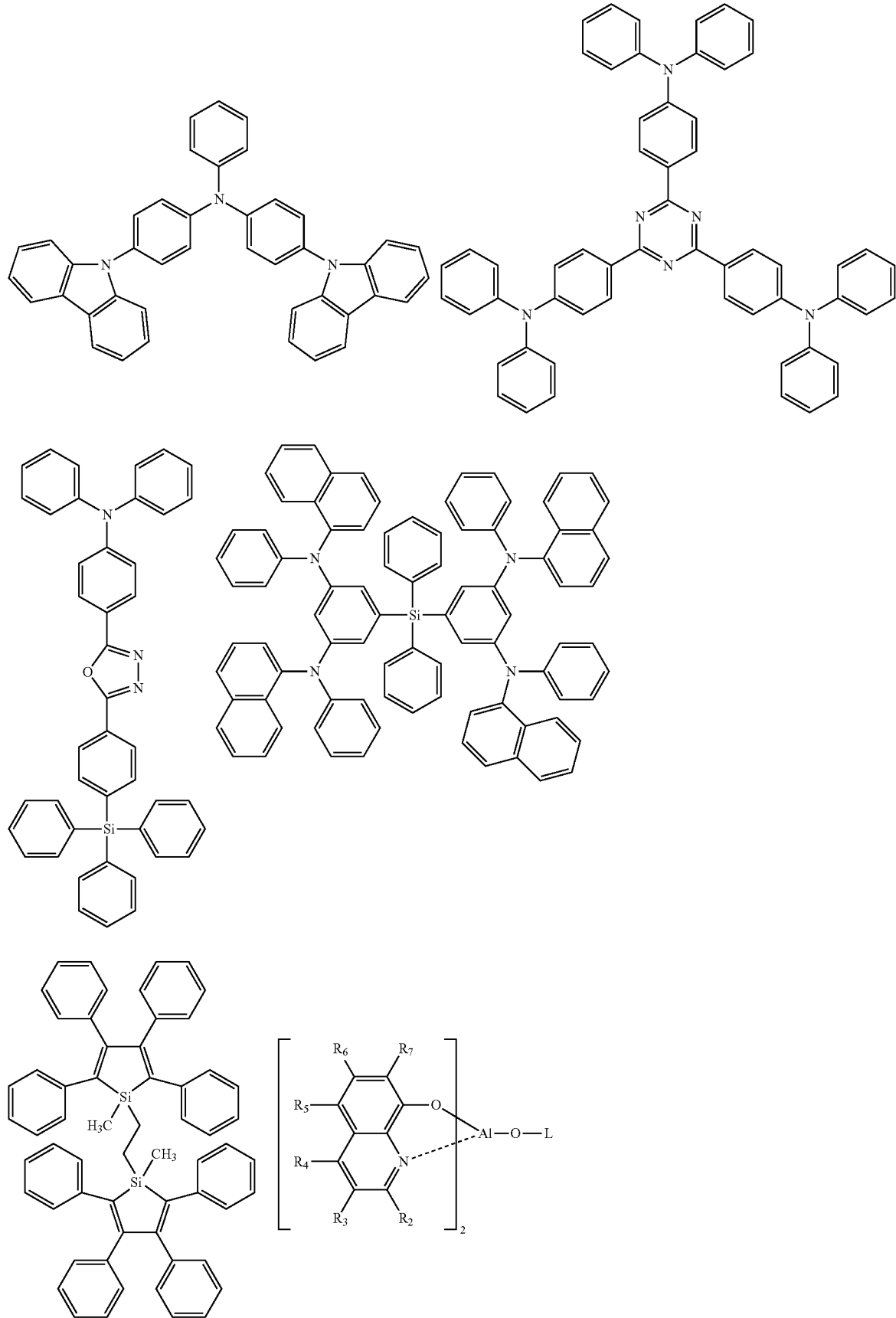

-continued
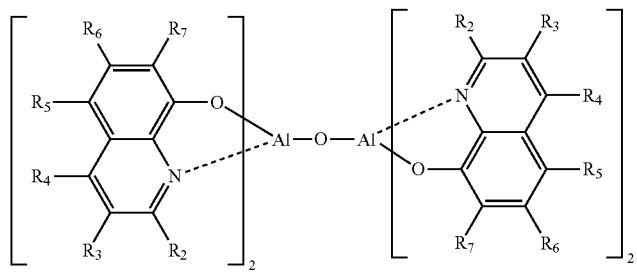
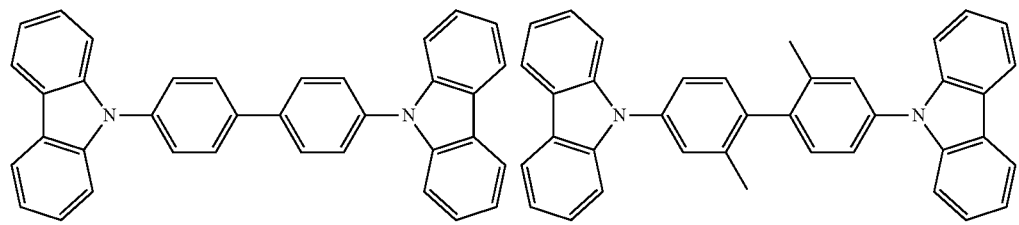
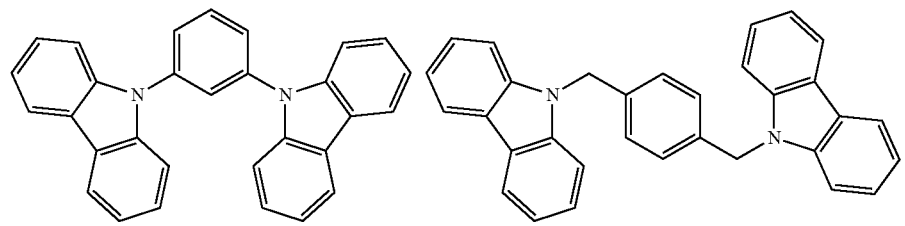
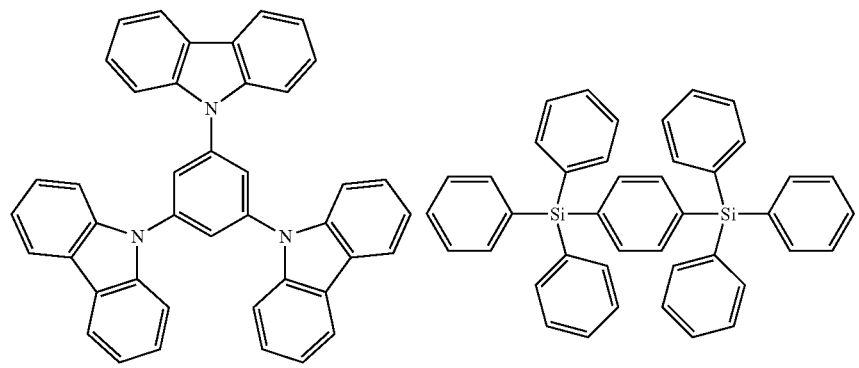
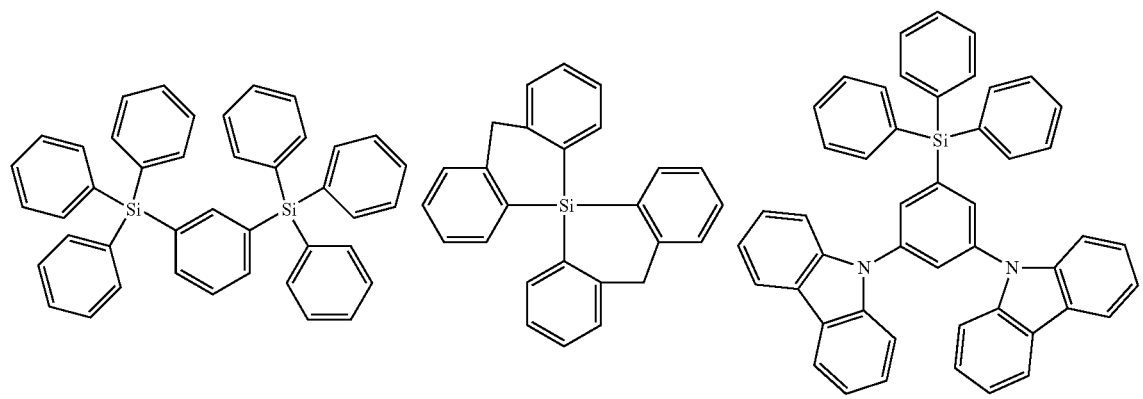

-continued
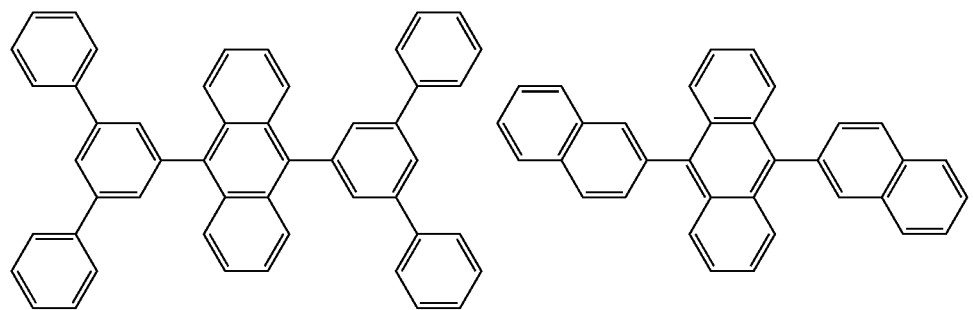

-continued
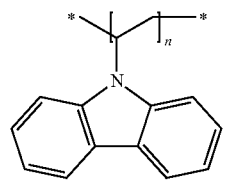
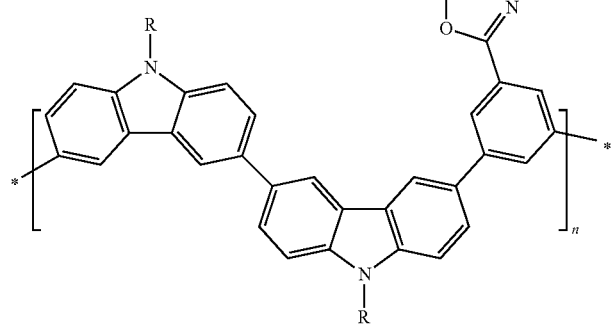
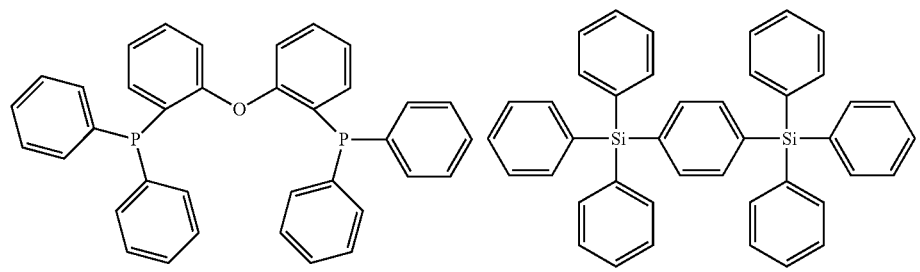
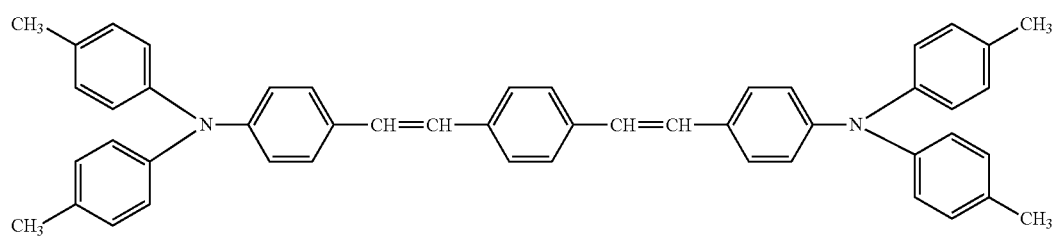
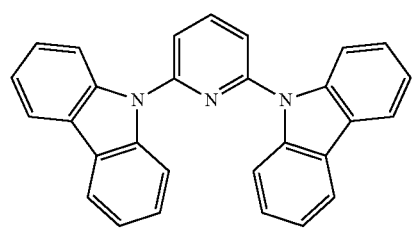

Preferred examples of a compound that may be used as the hole injection material are shown below.
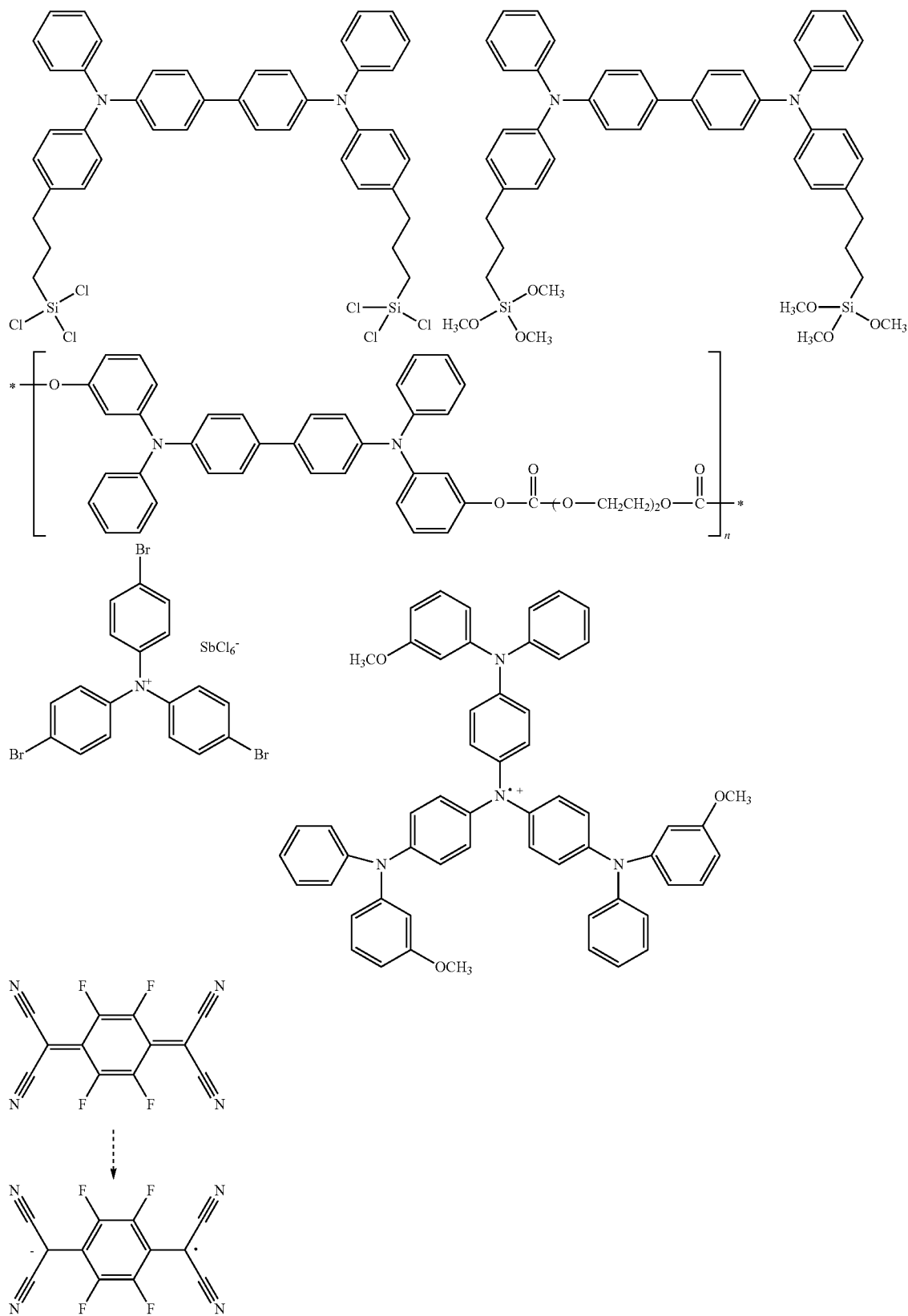

Preferred examples of a compound that may be used as the hole transporting material are shown below.
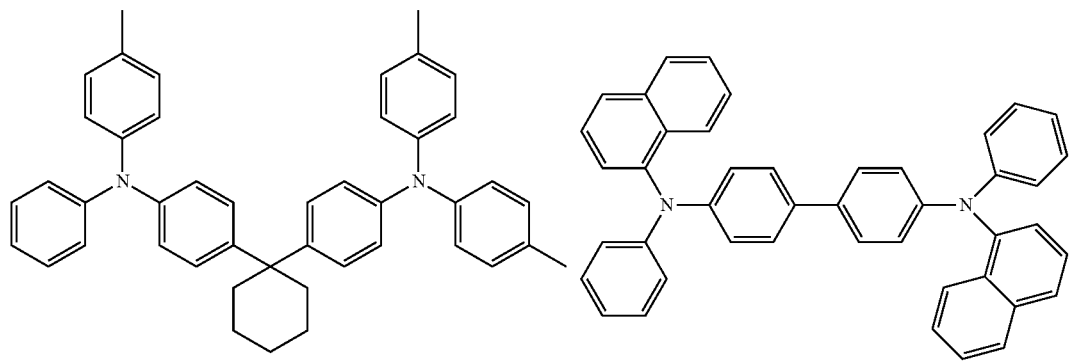
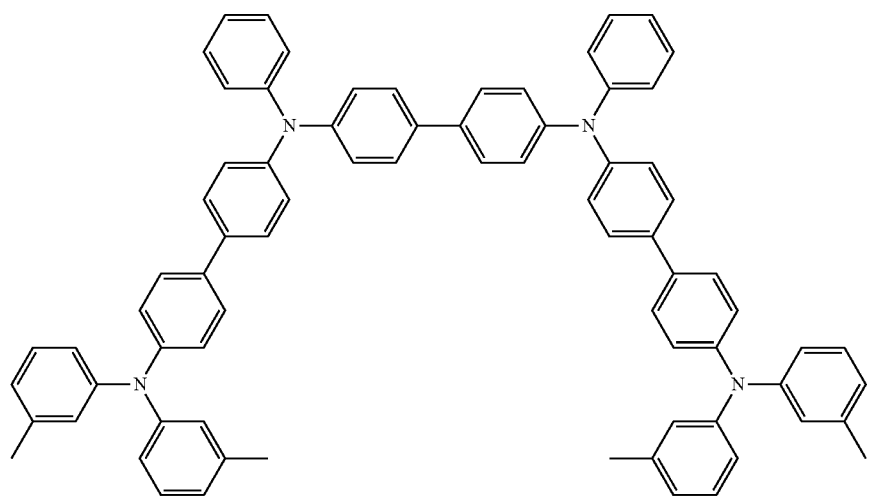
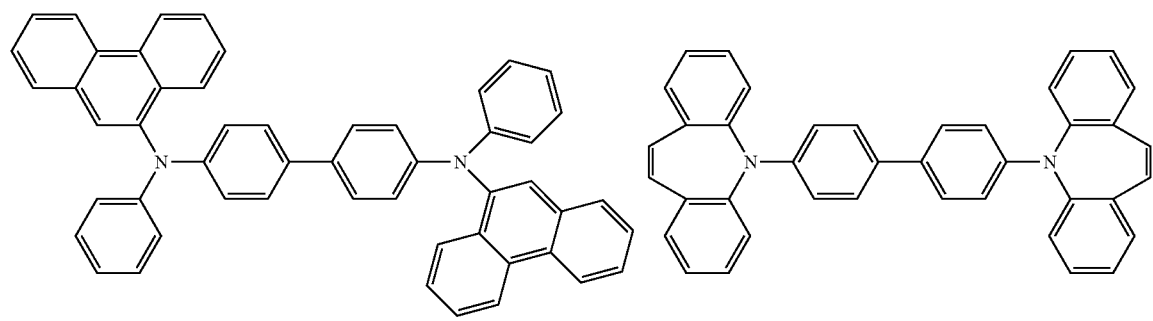

-continued
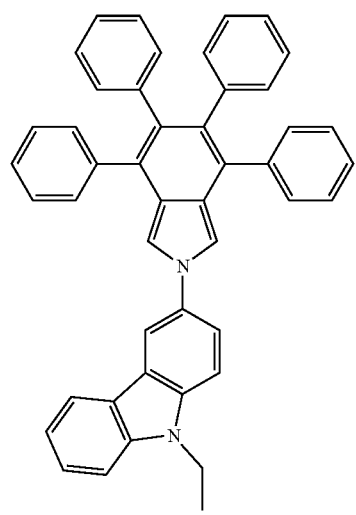
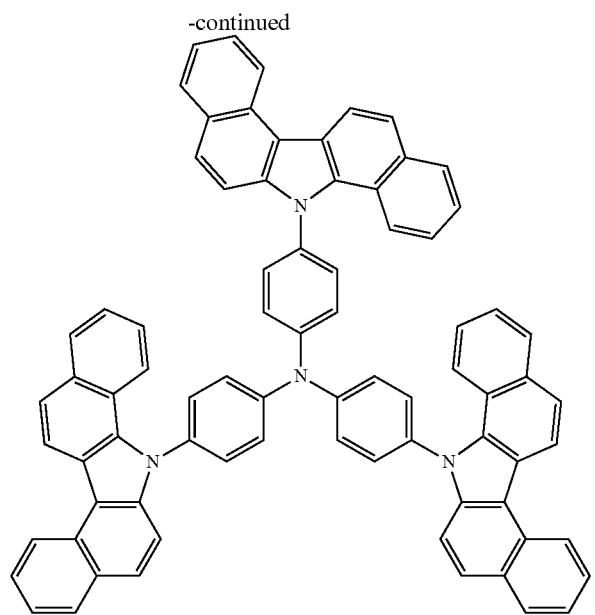
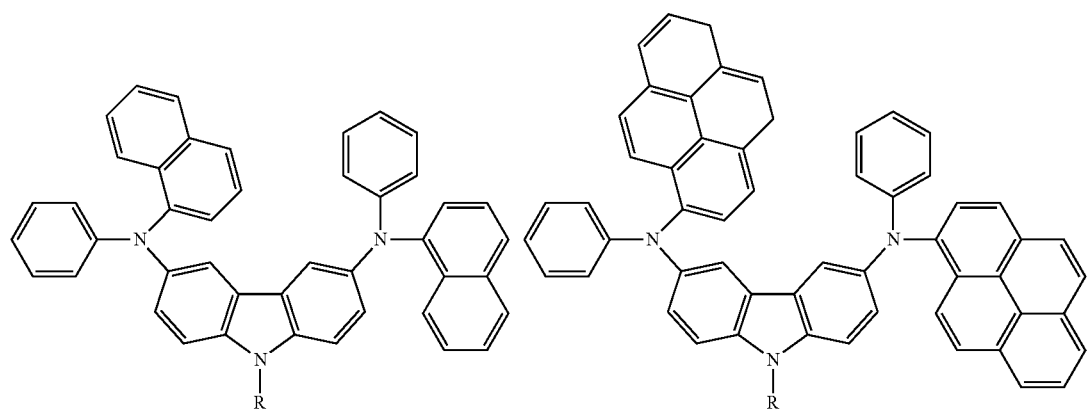
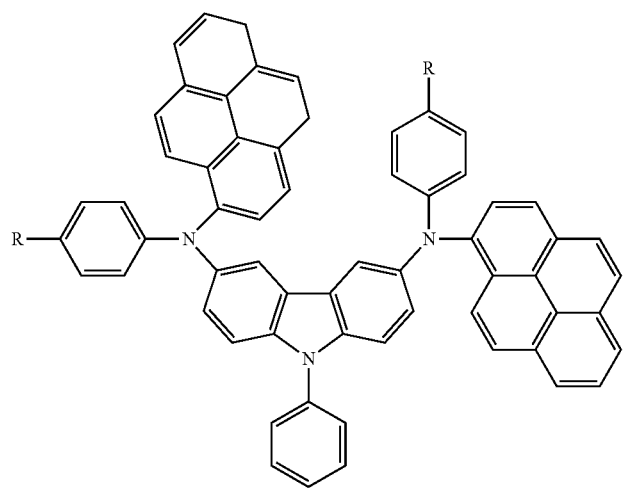

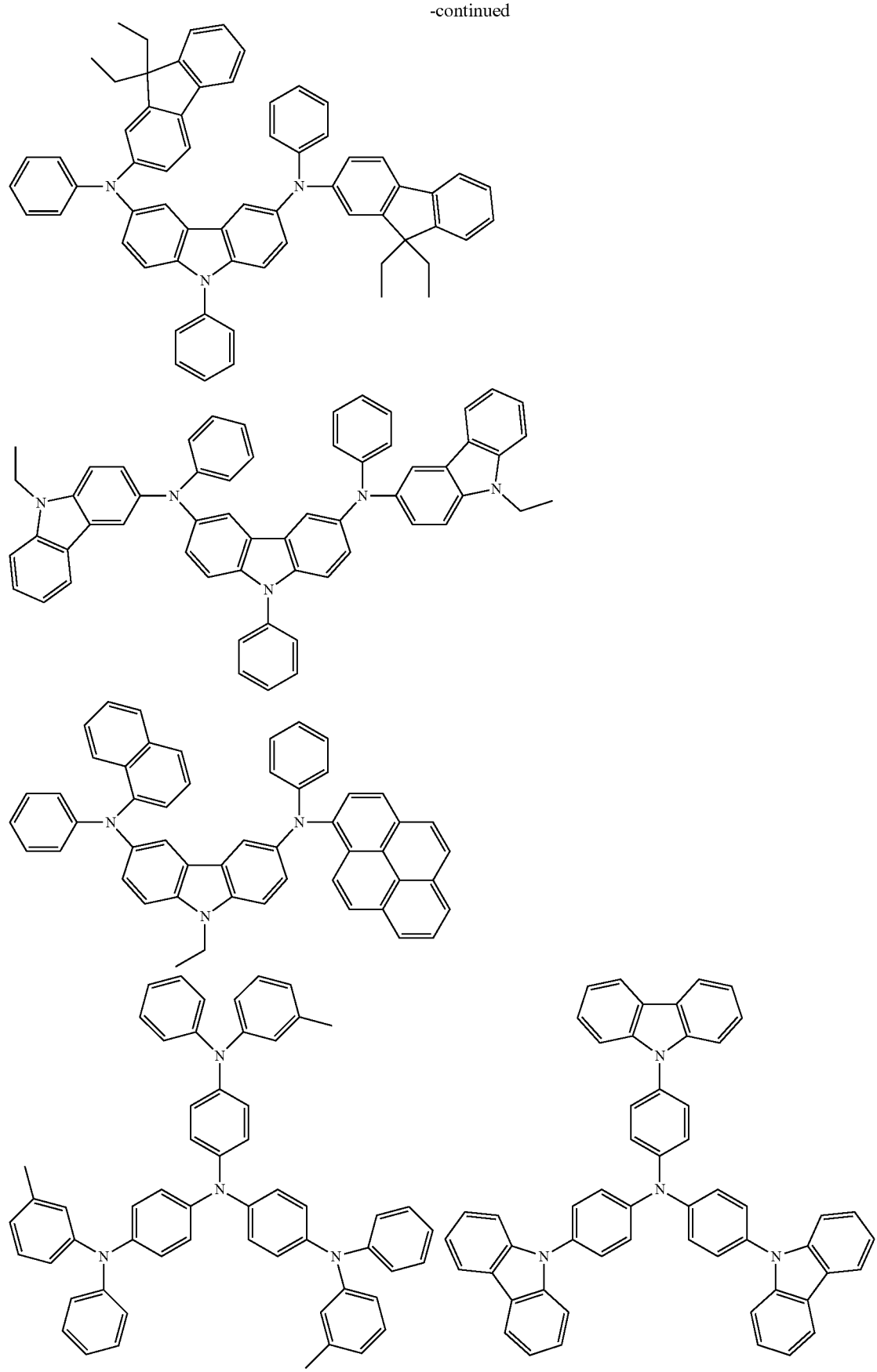

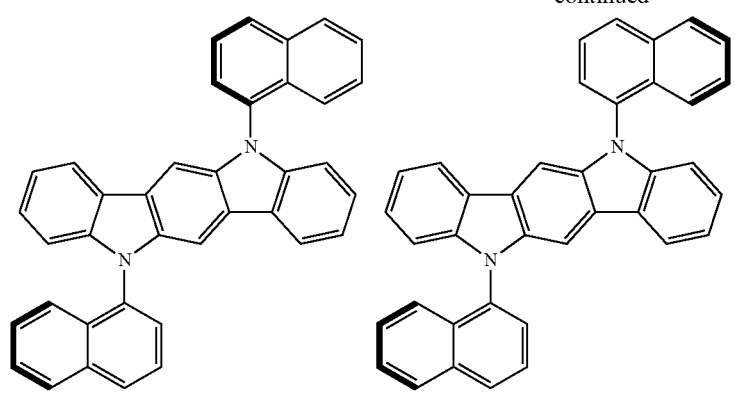
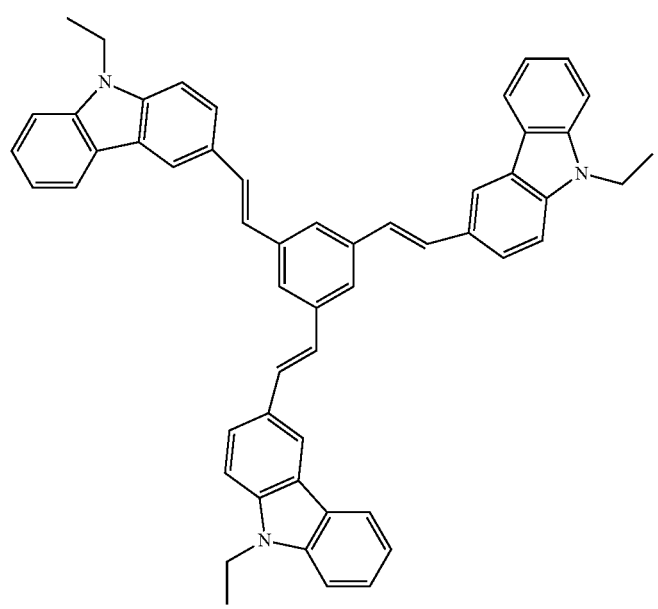
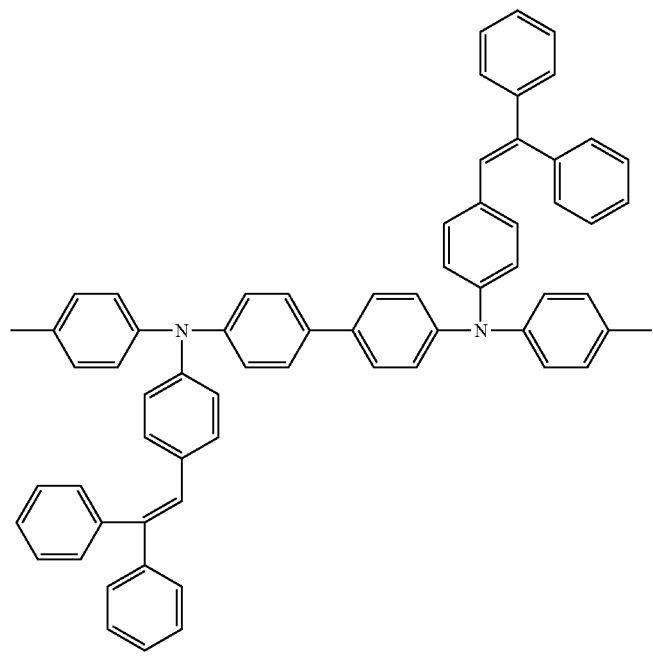

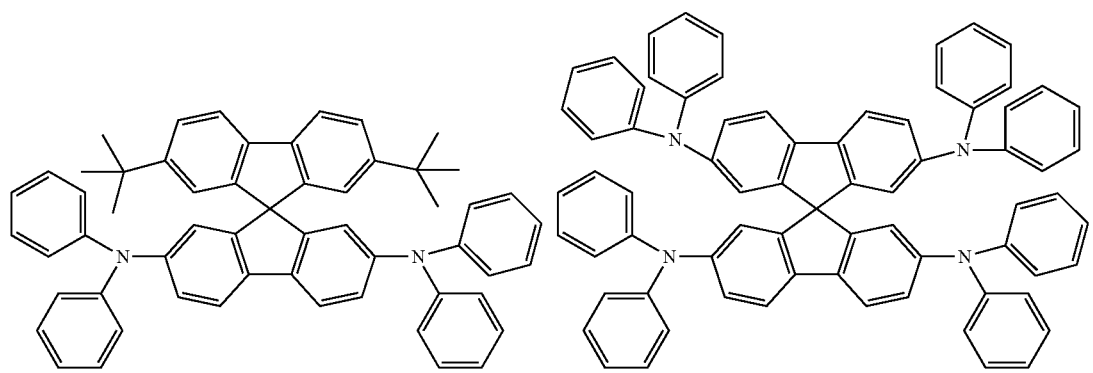
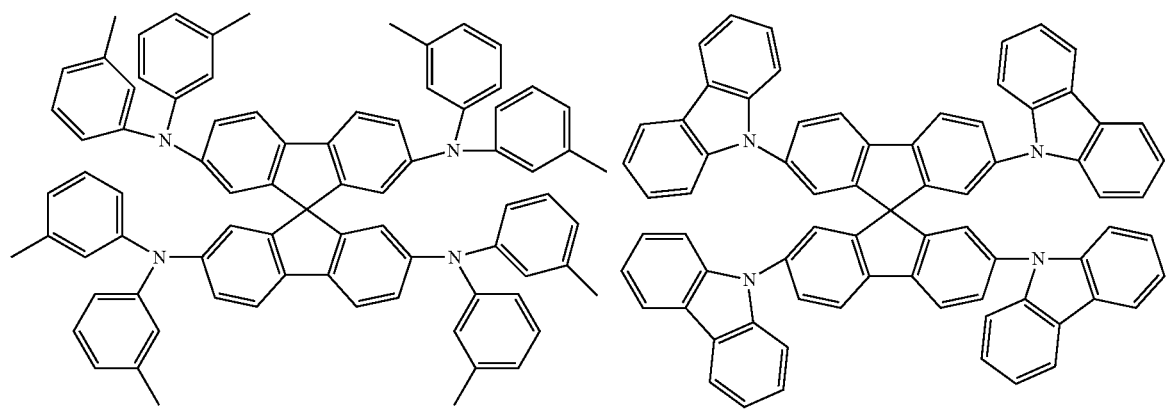
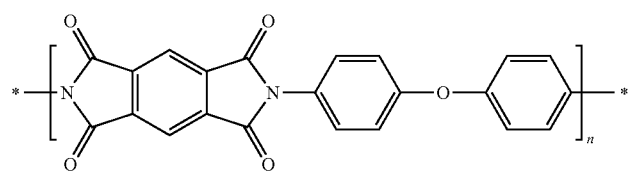

-continued
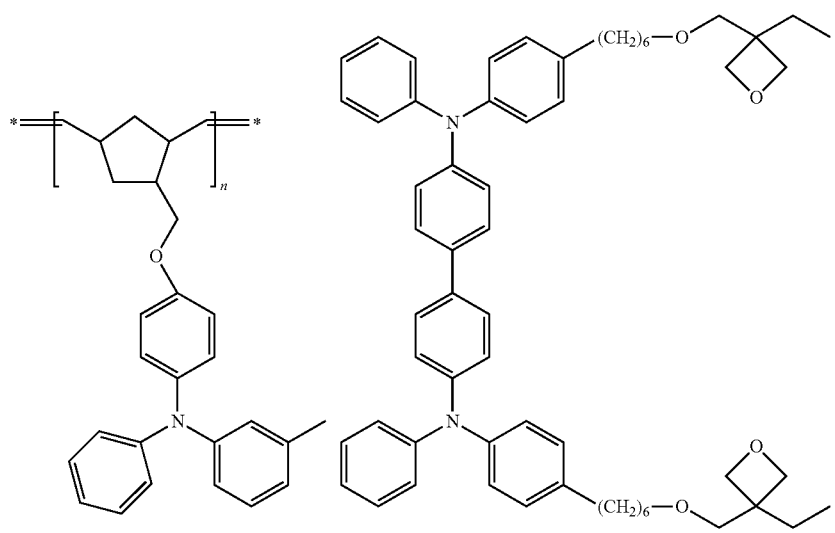
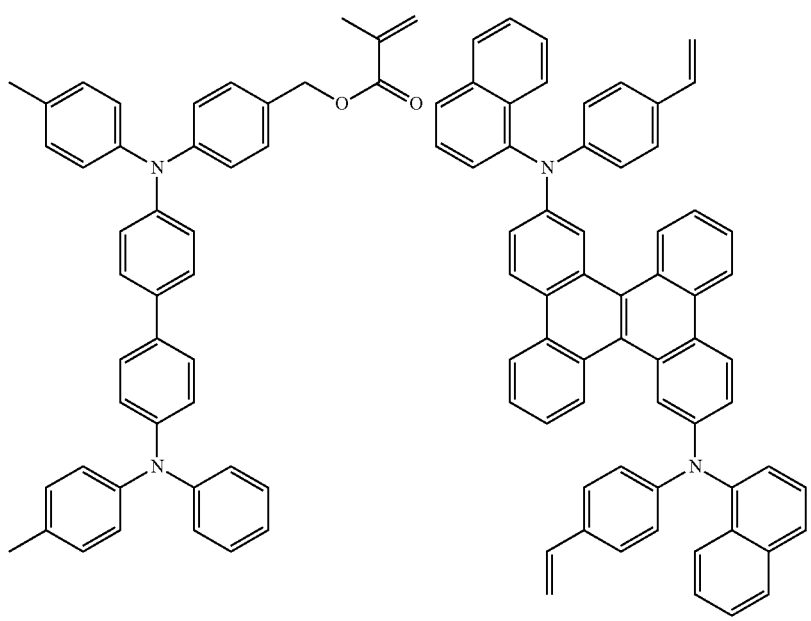
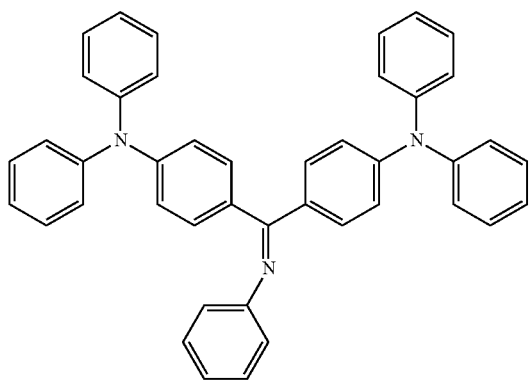

-continued
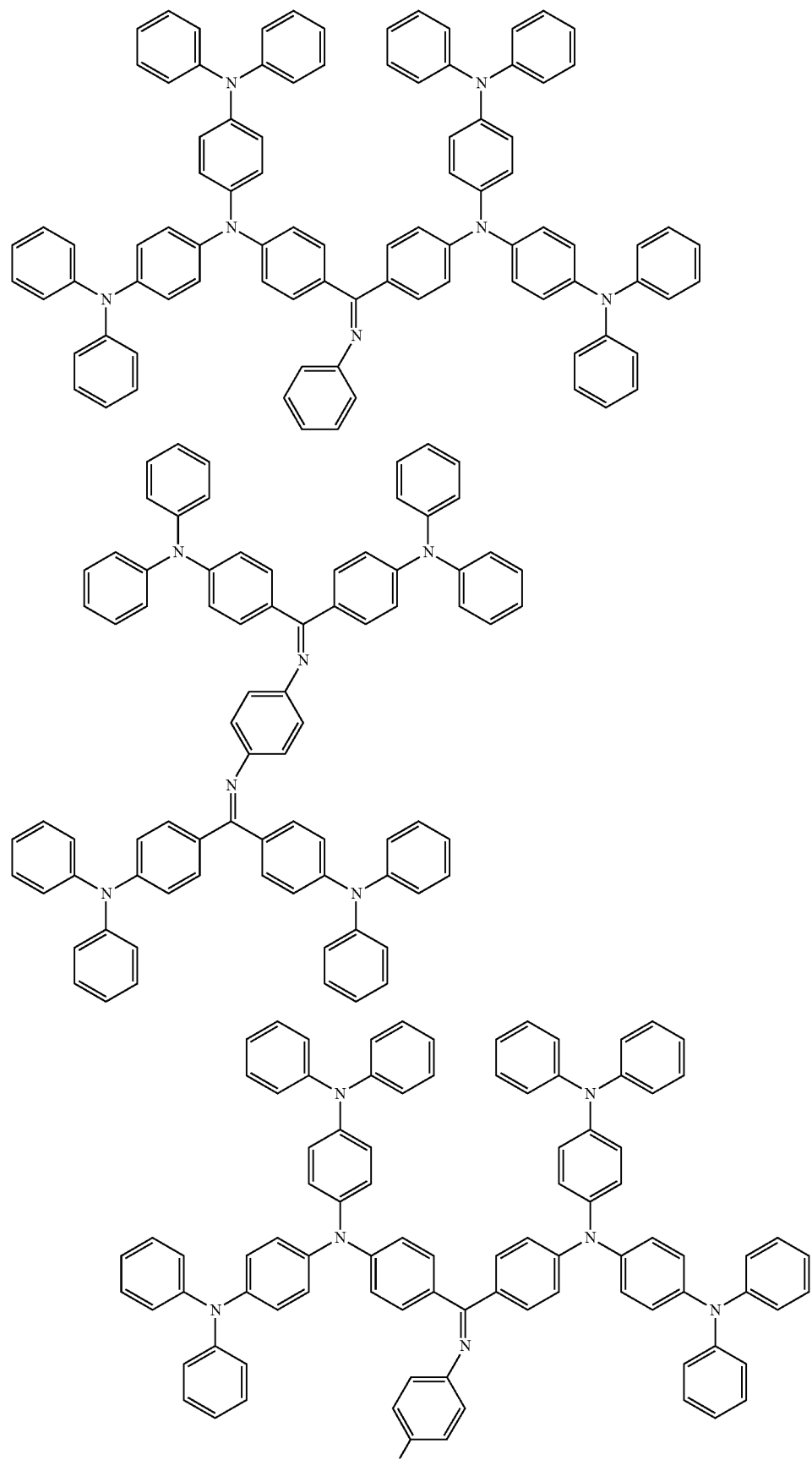

-continued
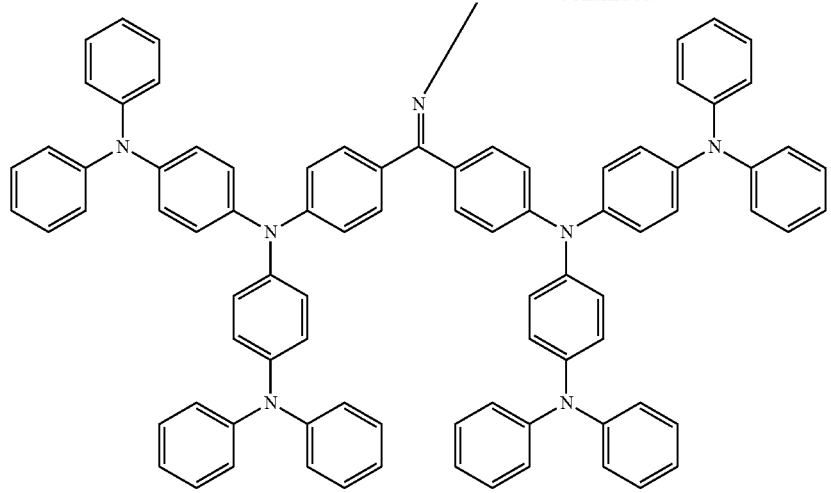
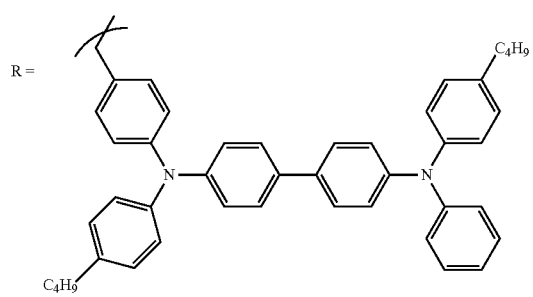
Preferred examples of a compound that may be used as the electron barrier material are shown below.
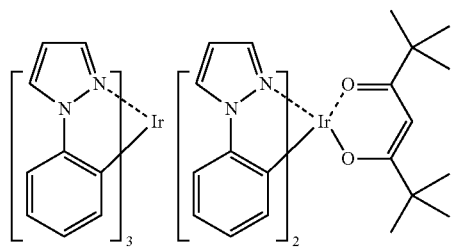
Preferred examples of a compound that may be used as the hole barrier material are shown below.
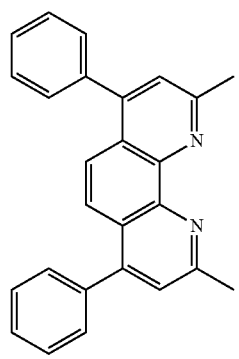

87
-continued
88
-continued
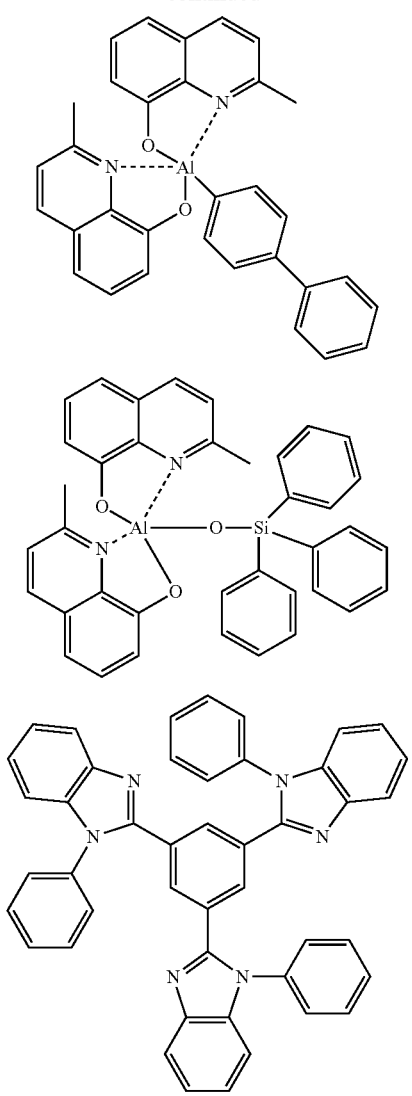
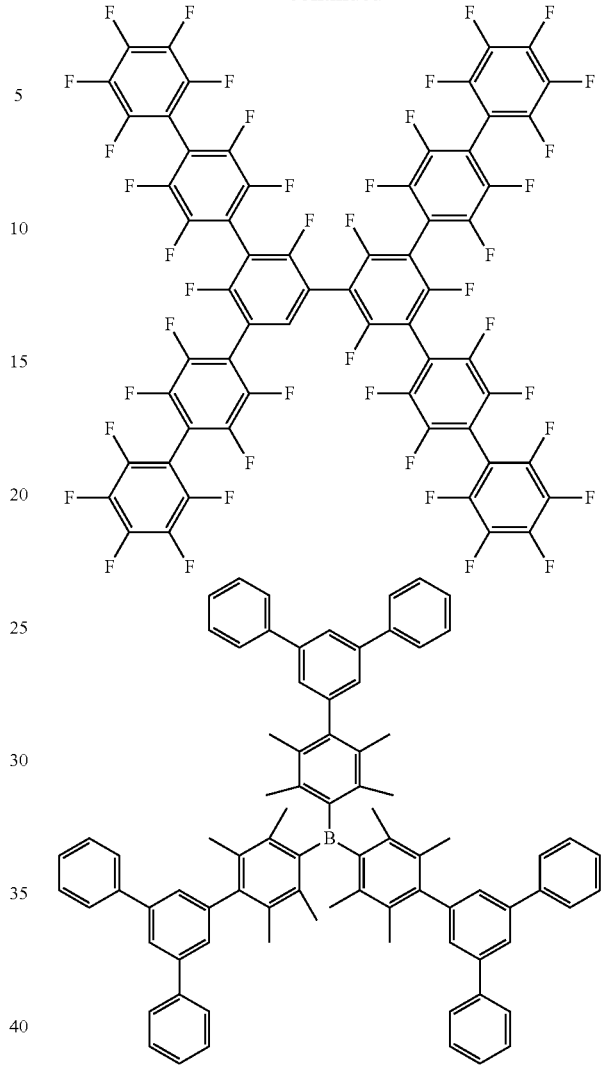
Preferred examples of a compound that may be used as the electron transporting material are shown below.
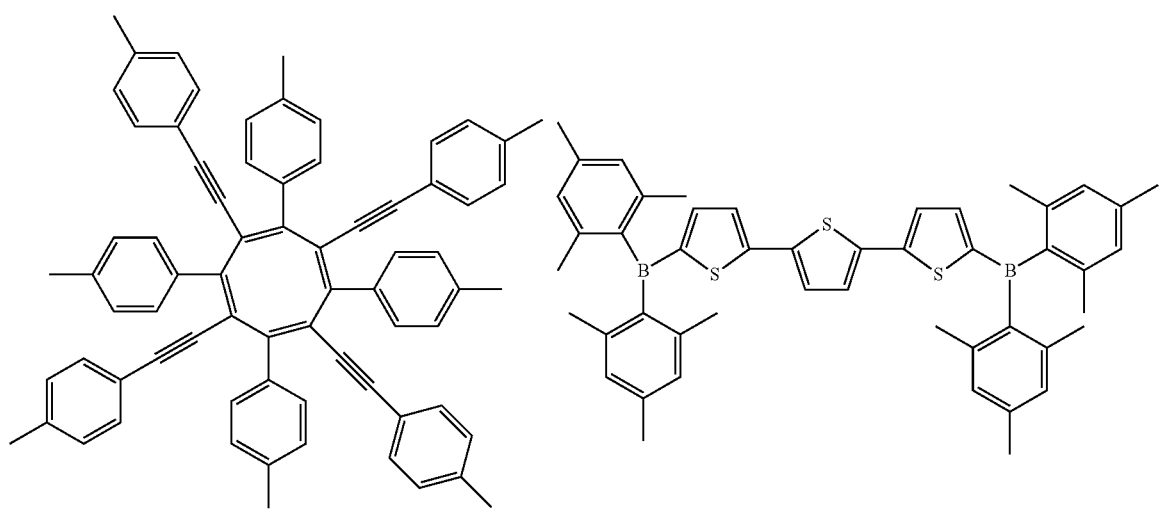

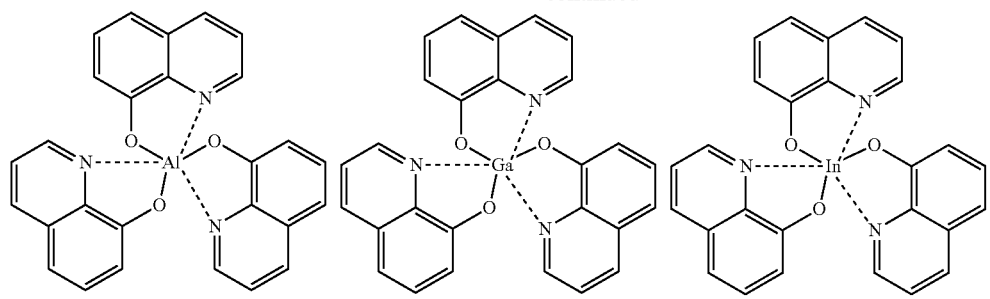
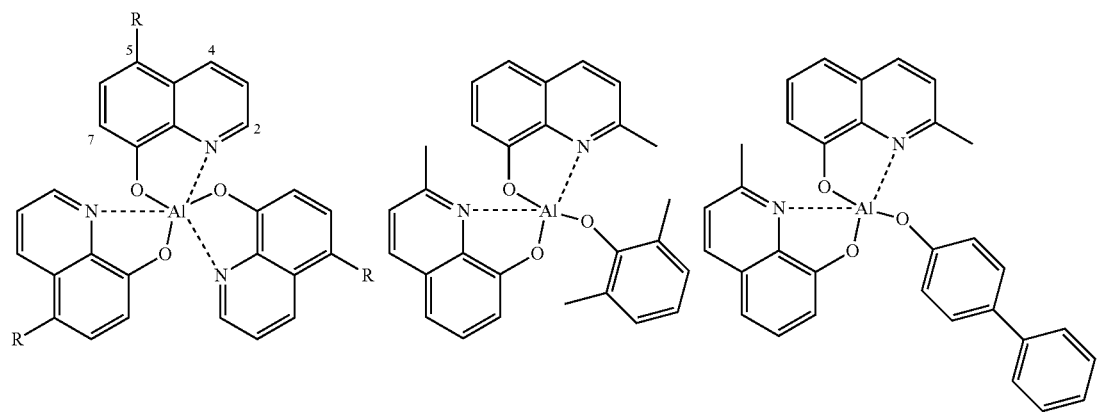
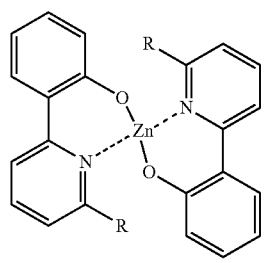
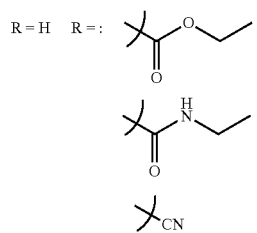
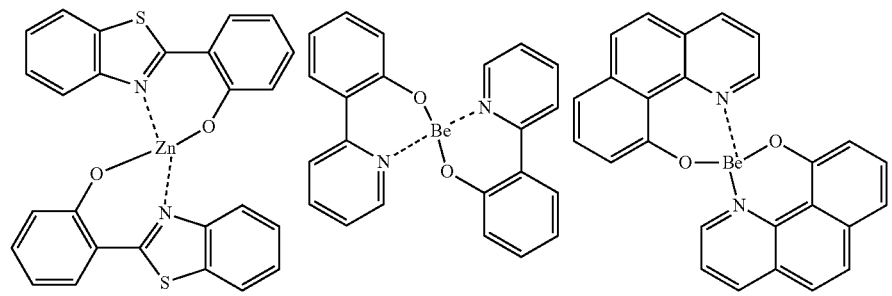

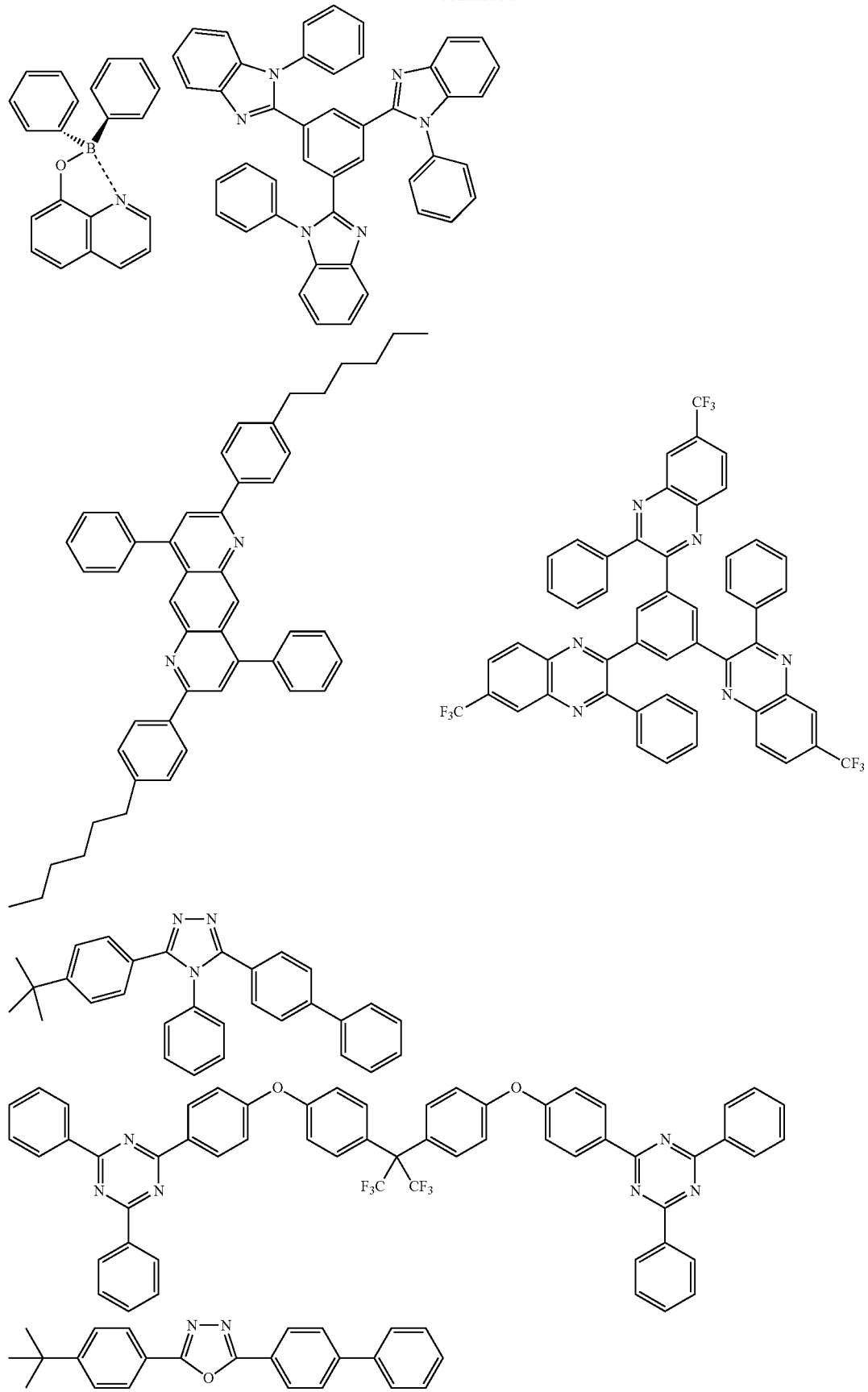

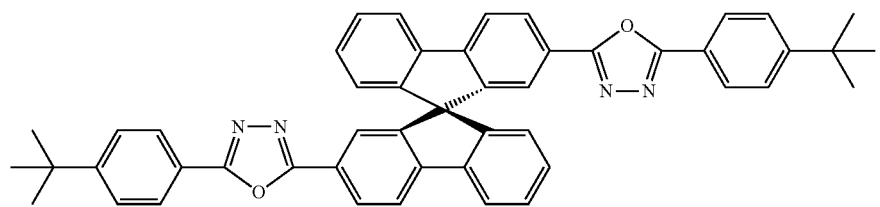
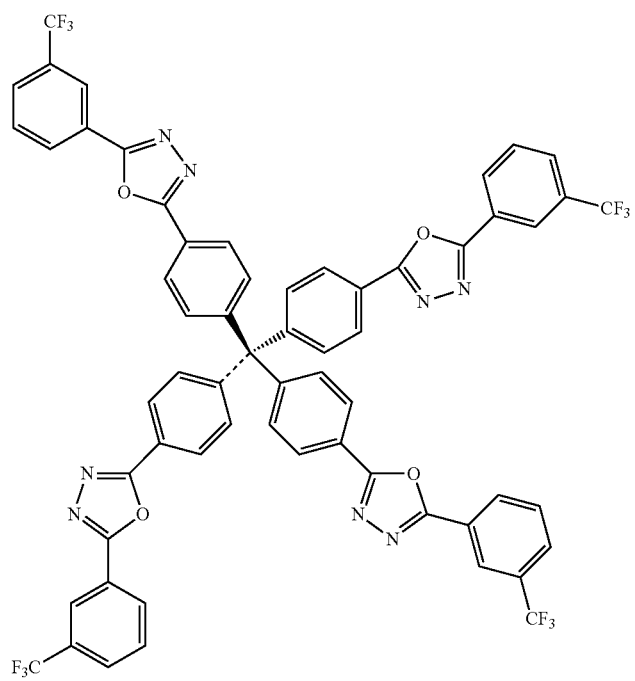
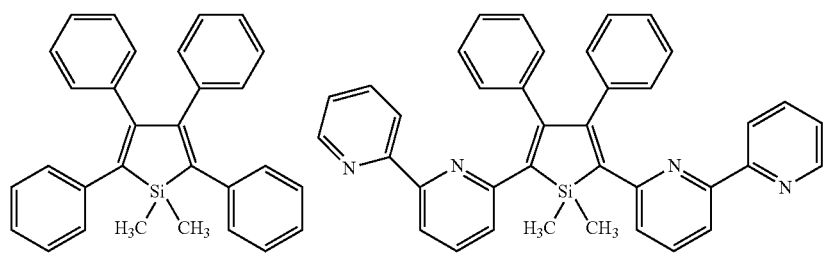
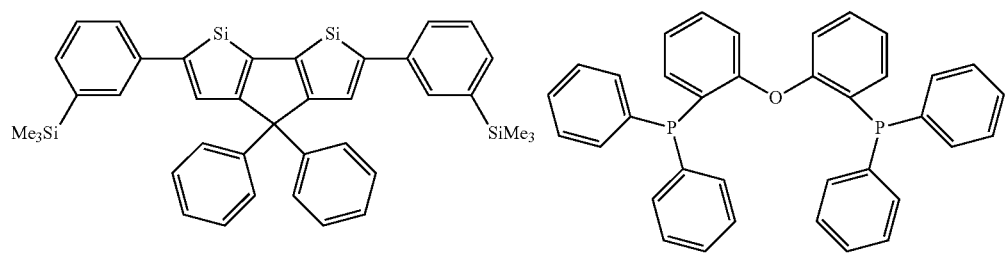
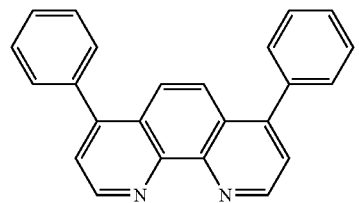

Preferred examples of a compound that may be used as the electron injection material are shown below.

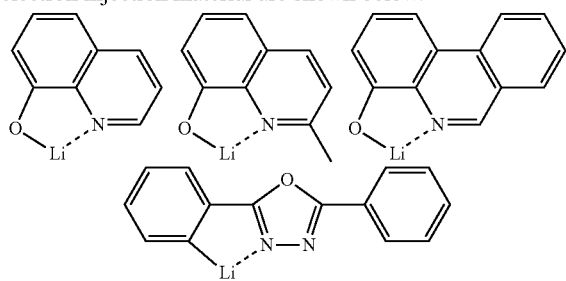

Preferred examples of a compound as a material that may be added are shown below. For example, the compound may be added as a stabilizing material.

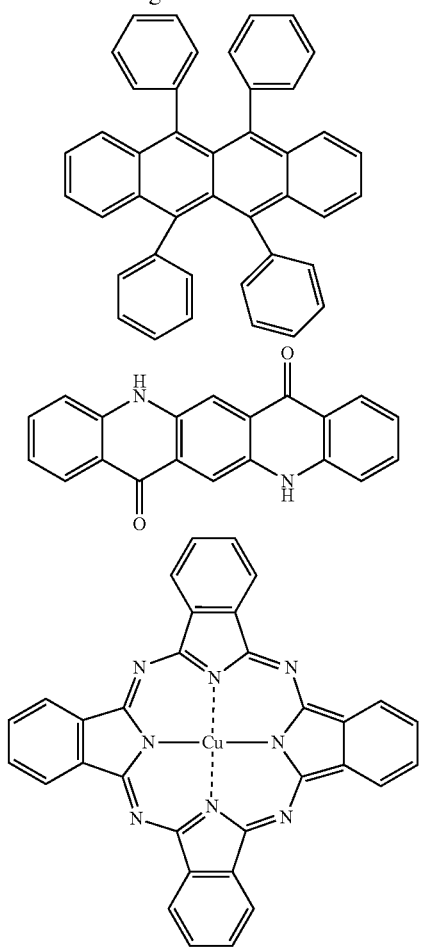

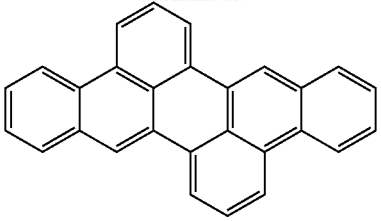

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light or delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not be observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below.

Synthesis Example 1

In this synthesis example, a compound 1 was synthesized according to the following scheme.

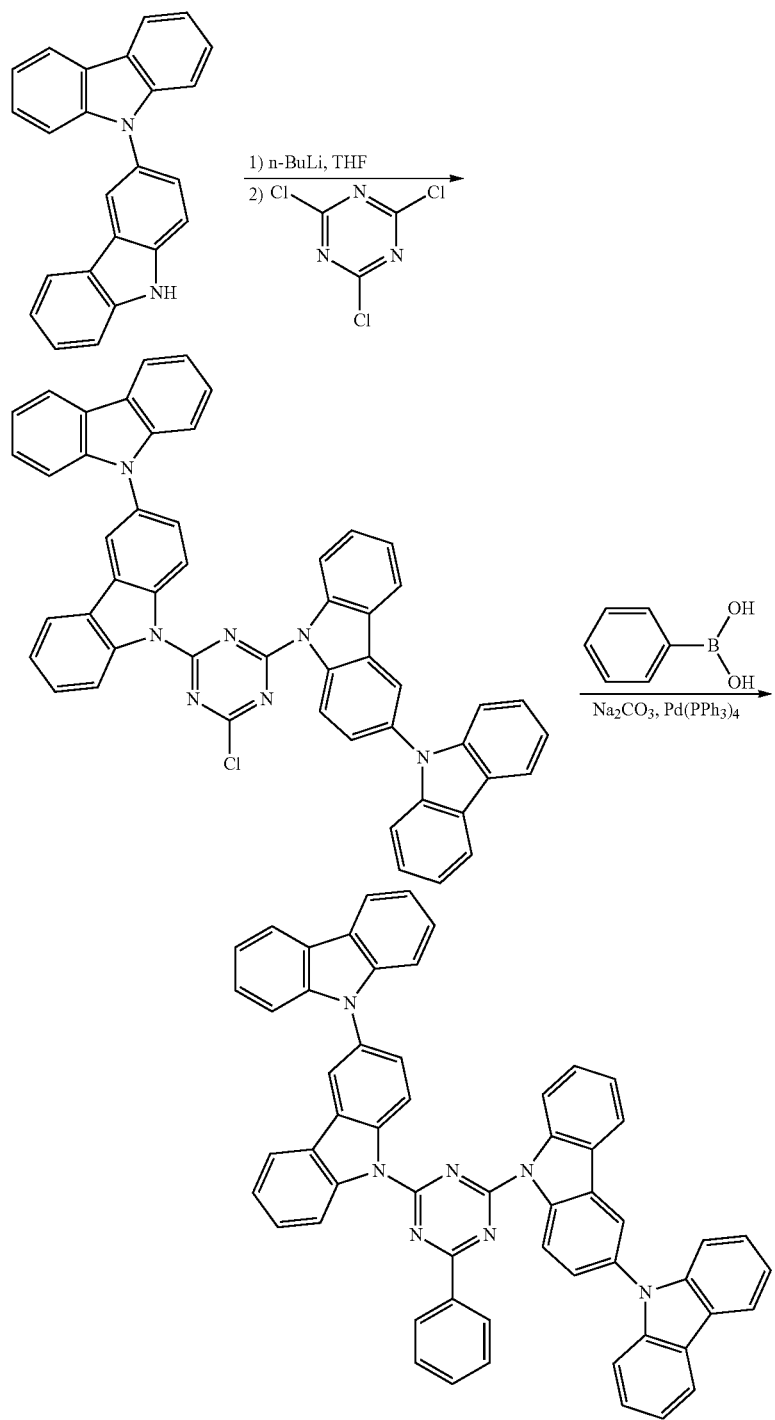

3,9'-bi-9H-carbazole (2.71 g, 8.15 mmol) was placed in a three-neck flask, the interior of the flask was substituted with nitrogen, and 50 mL of tetrahydrofuran was added thereto, followed by stirring for 10 minutes. After stirring, the solution was cooled to −78° C. and stirred for 20 minutes. After stirring, a 1.60 M hexane solution of n-butyllithium (5.00 mL, 8.00 mmol) was added thereto with a syringe, and the solution was stirred at −78° C. for 2 hours. The solution was then added to a mixture of 2,4,6-trichloro-1,3,5-triazine (0.740 g, 4.01 mmol) and 20 mL of tetrahydrofuran through a dropping funnel. The mixture was stirred at 70° C. for 8 hours, and then water was added thereto, followed by further stirring for 30 minutes. Thereafter, chloroform was added to the mixture, which was thus extracted therewith. After separating the organic layer and the aqueous layer, the organic layer was dried with sodium sulfate added thereto, and was suction-filtered to provide a filtrate. The resulting filtrate was purified by column chromatography, thereby providing 9,9'-(6- chloro-1,3,5-triazin-2,4-diyl)-bis-9H-carbazole with a yield amount of 2.67 g (yield: 85.80).

Under a nitrogen atmosphere, 9,9'-(6-chloro-1,3,5-triazin-2,4-diyl)-bis-9H-carbazole (1.50 g, 1.93 mmol) and phenylboronic acid (0.390 g, 3.20 mmol) were dissolved in 40 mL of tetrahydrofuran, and tetrakis(triphenylphosphine) palladium (0) (0.110 g, 0.0952 mmol) and a potassium carbonate aqueous solution (2.10 g, 7.00 mL) were added thereto, followed by refluxing for 48 hours. Chloroform was added to the mixture, which was thus extracted therewith. After separating the organic layer and the aqueous layer, the organic layer was dried with sodium sulfate added thereto, and was suction-filtered to provide a filtrate. The resulting filtrate was purified by column chromatography, thereby providing a compound 1 (yield amount: 1.38 g) (yield: 87.4%). The identification of the compound was performed by $^1$H-NMR and elemental analysis.

$^1$H-NMR (500 MHz, CDCl$_3$, TMS, δ): 9.32 (d, J=8.6 Hz, 2H), 9.15 (d, J=8.7 Hz, 2H), 8.82 (d, J=7.6 Hz, 2H), 8.29 (s, 2H), 8.20 (d, J=7.8 Hz, 4H), 8.10 (d, J=7.7 Hz, 2H), 7.76-7.72 (m, 5H), 7.63 (t, J=7.8 Hz, 2H), 7.51-7.43 (m, 10H), 7.33 (t, J=7.3 Hz, 4H)

Elemental analysis: calculated for C$_{57}$H$_{35}$N$_7$: C, 83.70%; H, 4.31%; N, 11.99%. found: C, 83.90%; H, 4.20%; N, 12.04%

Synthesis Example 2

In this synthesis example, a compound 4 was synthesized according to the following scheme.

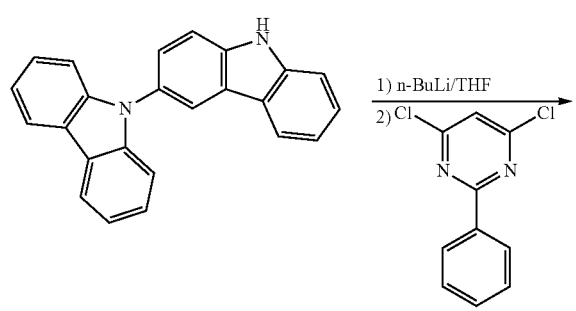

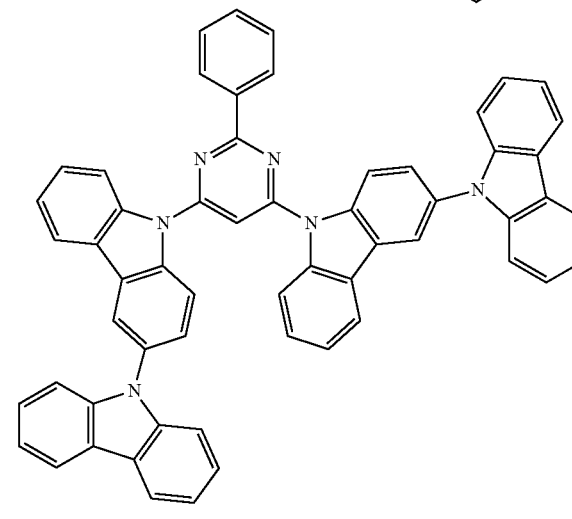

4

3.00 g of 3,9'-bi-9H-carbazole (9.03 mmol) was placed in a 300-mL three-neck flask, the interior of the flask was substituted with nitrogen, and 50 mL of tetrahydrofuran was added thereto. The solution was stirred at −78° C. for 20 minutes. 6.77 mL of a 1.60 mol/L hexane solution of n-butyllithium (10.8 mmol) was added dropwise to the solution with a syringe. The solution was stirred under a nitrogen atmosphere at −78° C. for 2 hours.

After stirring, a mixed solution of 0.924 g of 4,6-dichloro-2-phenylpyrimidine (4.11 mmol) and 20 mL of tetrahydrofuran was added to the solution, followed by stirring. The solution was slowly returned from −78° C. to room temperature, and then the solution was stirred at 80° C. for 10 hours.

After stirring, 100 mL of water was added to the solution, followed by stirring. After stirring, toluene was added to the mixture, which was thus extracted therewith. After extracting, the organic layer and the aqueous layer were separated, and the organic layer was dried with magnesium sulfate added thereto. After drying, the mixture was filtered to provide a filtrate.

The resulting filtrate was concentrated and purified by silica gel column chromatography. After purifying, the purified product was further purified by GPC to provide a solid matter. The resulting solid matter was recrystallized from a mixed solvent of chloroform and methanol, thereby providing a compound 4 in the form of white powder solid with a yield amount of 0.651 g (yield: 19.4%). The identification of the compound was performed by $^1$H-NMR, $^{13}$C-NMR and elemental analysis.

$^1$H-NMR (500 MHz, CDCl$_3$, TMS, δ): 8.78-8.76 (m, 2H), 8.54 (d, J=9.0 Hz, 2H), 8.31 (d, J=2.0 Hz, 2H), 8.26 (d, J=8.5 Hz, 2H), 8.19 (d, J=8.0 Hz, 4H), 8.13 (d, J=7.5 Hz, 2H), 7.98 (s, 1H), 7.72 (dd, J=9.0 Hz, 2.0 Hz, 2H), 7.66-7.59 (m, 5H), 7.46-7.41 (m, 10H), 7.33-7.31 (m, 4H)

$^{13}$C-NMR (125 MHz, CDCl$_3$, δ): 165.95, 160.41, 141.61, 139.43, 138.00, 136.89, 132.29, 131.91, 129.05, 128.67, 127.53, 126.69, 126.20, 126.00, 125.06, 123.31, 122.77, 120.87, 120.38, 119.89, 119.37, 114.05, 112.60, 109.74, 103.48

Elemental analysis: calculated for C$_{58}$H$_{36}$N$_6$: C, 85.27%; H, 4.44%; N, 10.29%. found: C, 84.97%; H, 4.36%; N, 10.40%

Synthesis Example 3

In this synthesis example, a compound 40 was synthesized according to the following scheme.

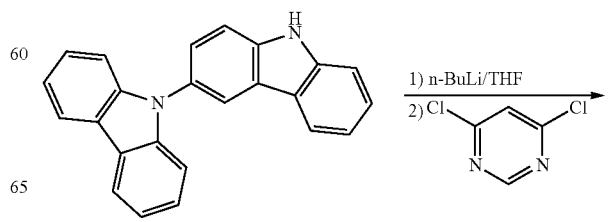

-continued

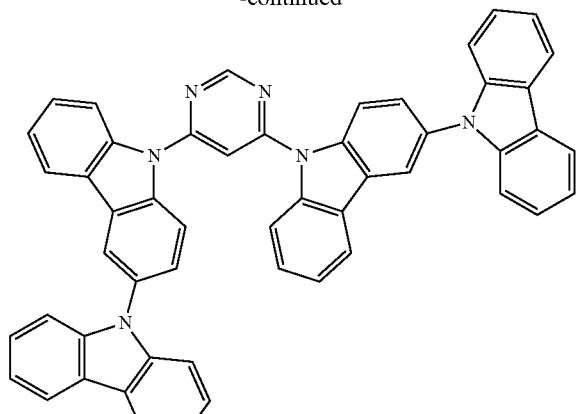

40

4.00 g of 3,9'-bi-9H-carbazole (12.0 mmol) was placed in a 300-mL three-neck flask, the interior of the flask was substituted with nitrogen, and 100 mL of tetrahydrofuran was then added thereto, followed by stirring at −78° C. for 20 minutes. 9.03 mL of a 1.60 mol/L hexane solution of n-butyllithium (14.4 mmol) was added dropwise to the solution with a syringe.

The solution was stirred under a nitrogen atmosphere at −78° C. for 2 hours. After stirring, a mixed solution of 0.813 g of 4,6-dichloropyrimidine (5.45 mmol) and 20 mL of tetrahydrofuran was added to the solution, followed by stirring. The solution was slowly returned from −78° C. to room temperature, and then the solution was stirred at 80° C. for 5 hours.

After stirring, 100 mL of water was added to the solution, followed by stirring. After stirring, toluene was added to the mixture, which was thus extracted therewith. After extracting, the organic layer and the aqueous layer were separated, and the organic layer was dried with magnesium sulfate added thereto. After drying, the mixture was filtered to provide a filtrate.

The resulting filtrate was concentrated and purified by silica gel column chromatography. After purifying, the purified product was further purified with a GPC preparative column to provide a solid matter. The resulting solid matter was added to a mixed solvent of toluene and methanol, followed by heating to 60° C. After heating, the mixture was suction-filtered to recover a solid matter, thereby providing a compound 40 in the form of white powder solid with a yield amount of 1.20 g (yield: 29.7%). The identification of the compound was performed by $^1$H-NMR, $^{13}$C-NMR and elemental analysis.

$^1$H-NMR (500 MHz, CDCl$_3$, TMS, δ): 9.45 (s, 1H), 8.50 (d, J=8.5 Hz, 2H), 8.29 (d, J=1.5 Hz, 2H), 8.21-8.18 (m, 6H), 8.13-8.11 (m, 3H), 7.70 (dd, J=8.5 Hz, 2.0 Hz, 2H), 7.59 (t, J=7.7 Hz, 2H), 7.46-7.41 (m, 10H), 7.34-7.30 (m, 4H)

$^{13}$C-NMR (125 MHz, CDCl$_3$, δ): 160.12, 159.96, 141.55, 139.24, 137.84, 132.49, 127.58, 126.79, 126.24, 126.00, 125.16, 123.31, 122.98, 120.91, 120.39, 119.91, 119.33, 114.17, 112.46, 109.70, 105.57

Elemental analysis: calculated for C$_{52}$H$_{32}$N$_6$: C, 84.30%; H, 4.35%; N, 11.34%. found: C, 84.17%; H, 4.27%; N, 11.33%

Example 1

In this example, an organic photoluminescent device having a light-emitting layer formed only of the compound 1 was produced and evaluated for the characteristics thereof while varying the temperature.

On a silicon substrate, the compound 1 was vapor-deposited from a vapor deposition source by a vacuum vapor deposition method under condition of a vacuum degree of 5.0× 10$^{-4}$ Pa, thereby forming a thin film of the compound 1 having a thickness of 100 nm at a rate of 0.3 nm/sec, which was designated as an organic photoluminescent device. The light emission spectrum from the thin film on irradiation of light at 337 nm with an N$_2$ laser was evaluated for characteristics at 300 K with Absolute Quantum Yield Measurement System, Model C9920-02, produced by Hamamatsu Photonics K.K., and thus light emission of 467 nm was confirmed with a photoluminescence efficiency of 43.1%. The time resolved spectrum on irradiation of light at 337 nm with an N$_2$ laser on the device was evaluated with Streak Camera, Model C4334, produced by Hamamatsu Photonics K.K. The component with a shorter light emission lifetime was determined as fluorescent light, and the component with a longer light emission lifetime was determined as delayed fluorescent light. As a result, the light emitted from the device contained approximately 96% of the fluorescent light component and approximately 4% of the delayed fluorescent light component.

Figure 2:
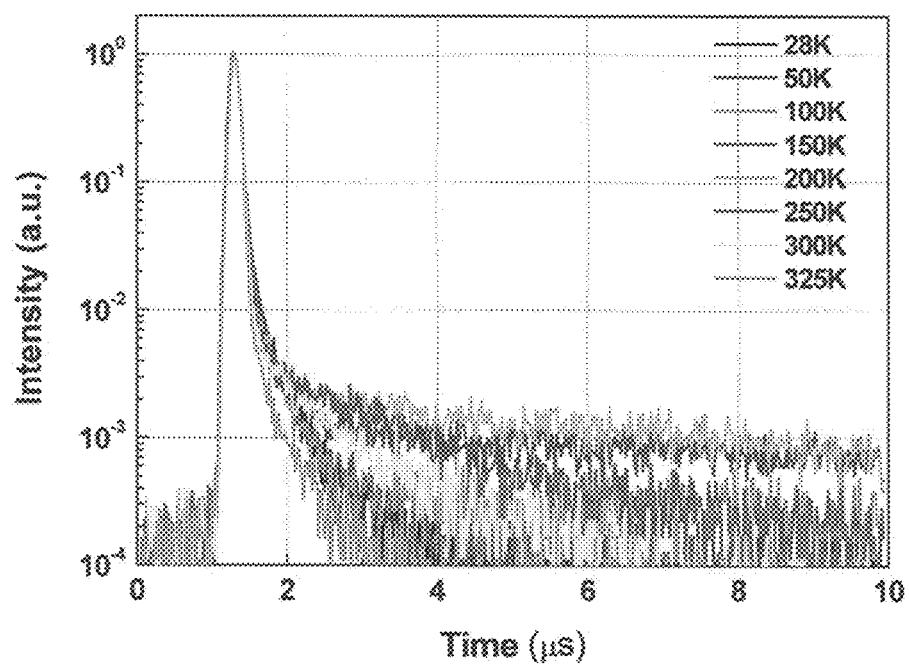
FIG. 2 is a graph showing the light emission lifetime depending on temperature of the organic photoluminescent device of Example 1.
Figure 3:
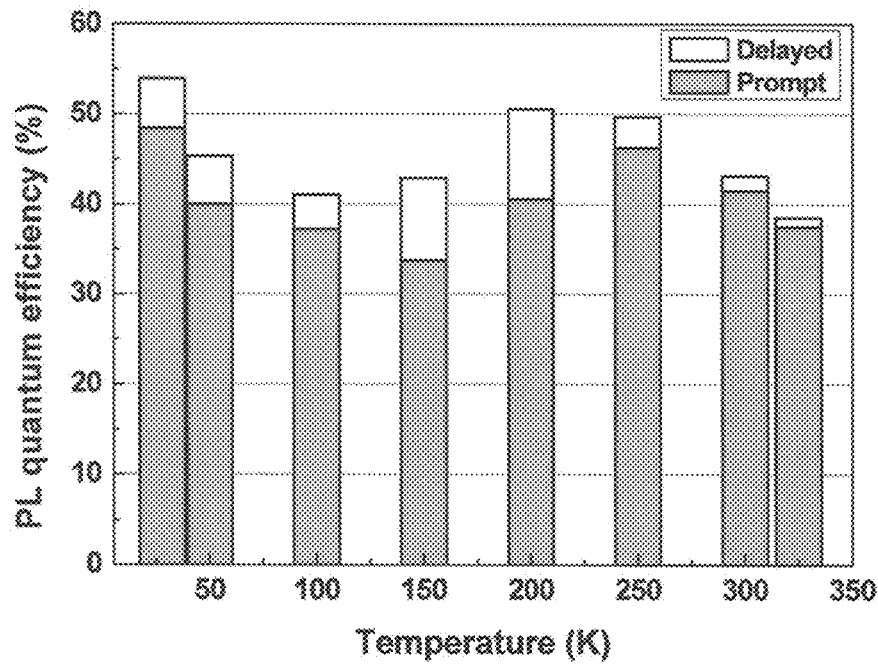
FIG. 3 is a graph showing the photoluminescence quantum efficiency-temperature characteristics of the organic photoluminescent device of Example 1.

The same measurement as above was performed at an evaluation temperature of the organic photoluminescent device that was changed to 28 K, 50 K, 150 K, 200 K, 250 K and 325 K. A graph showing the light emission lifetimes depending on the temperature is shown in FIG. 2. The photoluminescence efficiency and the ratios of the fluorescent light component and the delayed fluorescent light component at the respective temperatures are shown in FIG. 3.

Example 2

In this example, organic photoluminescent devices having a light-emitting layer formed of the compound 1 and various host materials were produced and evaluated for the characteristics thereof.

On a silicon substrate, the compound 1 and mCP were vapor-deposited from separate vapor deposition sources respectively by a vacuum vapor deposition method under condition of a vacuum degree of 5.0×10$^{-4}$ Pa, thereby forming a thin film having a concentration of the compound 1 of 6.0% by weight having a thickness of 100 nm at a rate of 0.3 nm/sec, which was designated as an organic photoluminescent device. The light emission spectrum from the thin film on irradiation of light at 337 nm with an N$_2$ laser was evaluated for characteristics at 300 K with Absolute Quantum Yield Measurement System, Model C9920-02, produced by Hamamatsu Photonics K.K., and thus light emission of 454 nm was confirmed with a photoluminescence efficiency of 38.9%. The time resolved spectrum on irradiation of light at 337 nm with an N$_2$ laser on the device was evaluated with Streak Camera, Model C4334, produced by Hamamatsu Photonics K.K., and thus a fluorescent light component and a delayed fluorescent light component were observed as similar to Example 1.

Organic photoluminescent devices were produced in the same manner as above except that BSB, PYD2, DPEPO and UGH2 were used as a host material instead of mCP, and were measured in the same manner as above. Delayed fluorescent light was observed in all the cases using the aforementioned host materials, and it was confirmed that the ratio of the delayed fluorescent light component was particularly high in the case where a host material that had T1 (minimum excitation triplet energy level) of 3.0 eV or more, more preferably 3.1 eV or more, (DPEPO and UGH2) was used.

Comparative Example 1

In this comparative example, a device having a thin film was formed in the same manner as in Example 1 except that a comparative compound having the following structure was used instead of the compound 1. The photoluminescence efficiency measured was 24.8%. The time resolved spectrum on irradiation of light at 337 nm with an $N_2$ laser on the device was evaluated with Streak Camera, Model C4334, produced by Hamamatsu Photonics K.K. Only a component with a short light emission lifetime was observed, but delayed fluorescent light was not observed.

Comparative Compound

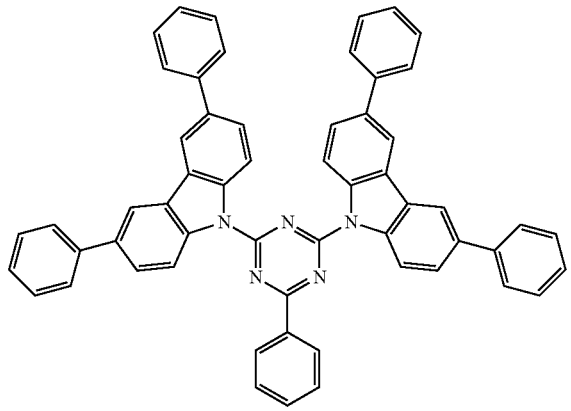 [SMILES: c1ccc(-c2ccc3c(c2)c2cc(-c4ccccc4)ccc2n3-c2nc(-c3ccccc3)nc(-n3c4ccc(-c5ccccc5)cc4c4cc(-c5ccccc5)ccc43)n2)cc1]

Example 3

In this example, a solution was prepared and measured for the characteristics thereof.

Figure 4:
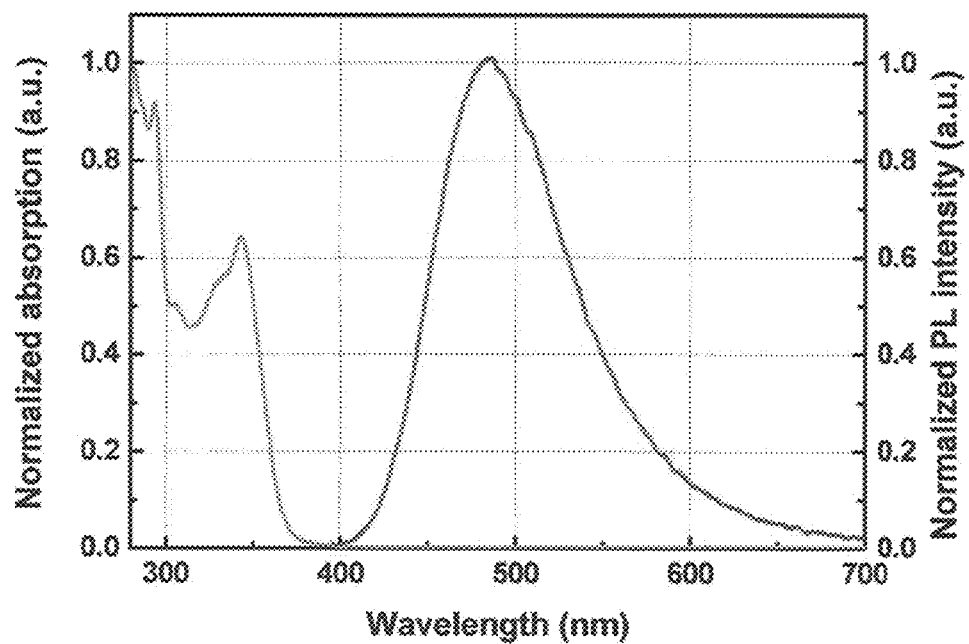
FIG. 4 is a graph showing the UV absorption and photoluminescent light emission characteristics of the solution of Example 3.

A toluene solution of the compound 4 (concentration: $10^{-5}$ mol/L) was prepared and measured for the UV absorption characteristics with UV-VIS Spectrophotometer (UV-2550, produced by Shimadzu Corporation). The photoluminescent (PL) characteristics thereof on irradiation of light at 343 nm were measured with Spectrofluorometer (FP6500-A-ST, produced by Jasco Corporation). The results are shown in FIG. 4.

Example 4

In this example, a solution was prepared and measured for the characteristics thereof.

Figure 5:
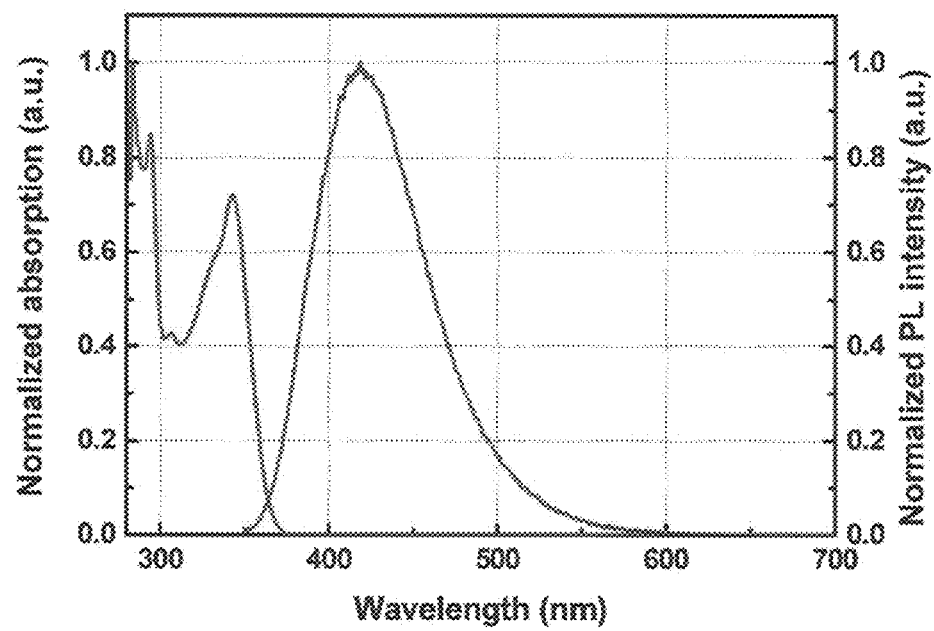
FIG. 5 is a graph showing the UV absorption and photoluminescent light emission characteristics of the solution of Example 4.

A toluene solution of the compound 40 (concentration: $10^{-5}$ mol/L) was prepared and measured for the UV absorption characteristics with UV-VIS Spectrophotometer (UV-2550, produced by Shimadzu Corporation). The photoluminescent (PL) characteristics thereof on irradiation of light at 342 nm were measured with Spectrofluorometer (FP6500-A-ST, produced by Jasco Corporation). The results are shown in FIG. 5.

Example 5

In this example, an organic electroluminescent device having a light-emitting layer formed of the compound 1 and DPEPO was produced and evaluated for the characteristics thereof.

Thin films each were formed by a vacuum vapor deposition method at a vacuum degree of $5.0 \times 10^{-4}$ Pa on a glass substrate having formed thereon an anode formed of indium tin oxide (ITO) having a thickness of 100 nm. First, α-NPD was formed to a thickness of 40 nm on ITO. The compound 1 and mCP were then co-vapor-deposited from separate vapor deposition sources respectively to form a layer having a thickness of 10 nm. The concentration of the compound 1 herein was 6.0% by weight. The compound 1 and DPEPO were then co-vapor-deposited from separate vapor deposition sources respectively to form a layer having a thickness of 20 nm, which was designated as a light-emitting layer. The concentration of the compound 1 herein was 6.0% by weight. DPEPO was then formed to a thickness of 10 nm, and TPBi was further formed to a thickness of 30 nm. Lithium fluoride (LiF) was then vacuum vapor-deposited to a thickness of 0.8 nm, and then aluminum (Al) was vapor-deposited to a thickness of 80 nm, which was designated as a cathode, thereby completing an organic electroluminescent device.

Figure 6:
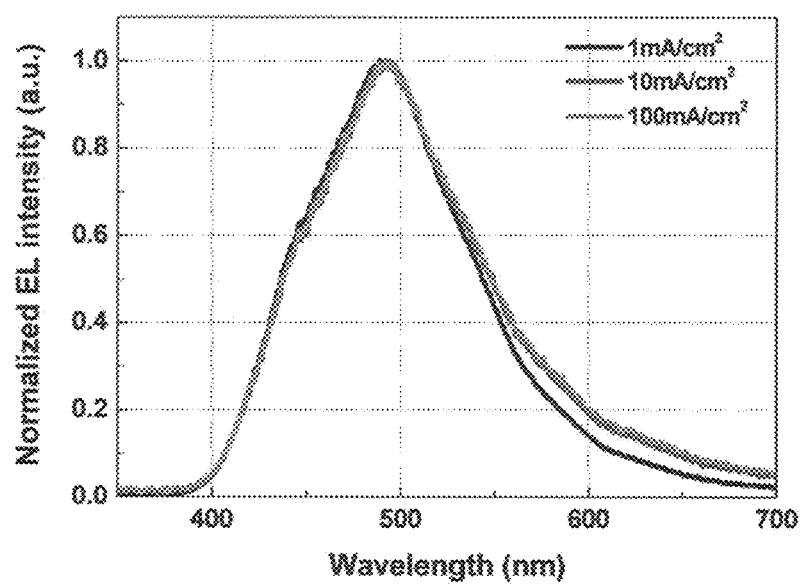
FIG. 6 is electroluminescent (EL) spectra of the organic electroluminescent device of Example 5.
Figure 7:
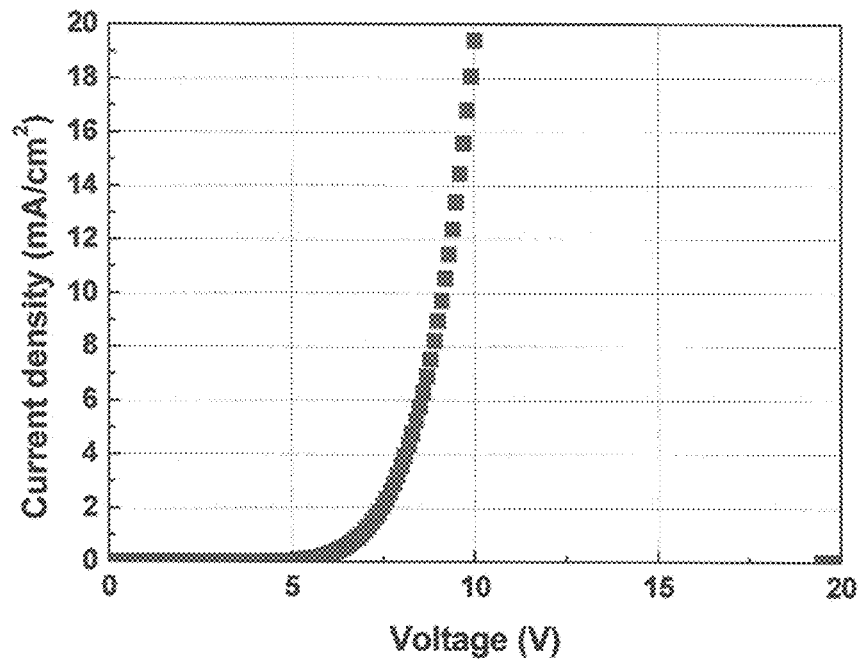
FIG. 7 is a graph showing the electric current density-voltage characteristics of the organic electroluminescent device of Example 5.
Figure 8:
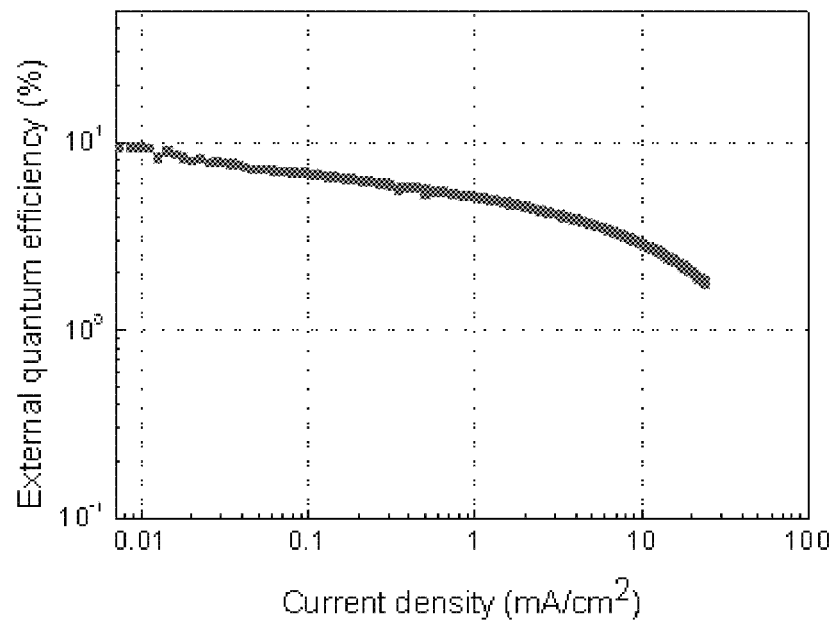
FIG. 8 is a graph showing the external quantum efficiency-electric current density characteristics of the organic electroluminescent device of Example 5.

The organic electroluminescent device thus produced was measured with Semiconductor Parameter Analyzer (E5273A, produced by Agilent Technologies, Inc.), Optical Power Meter (1930C, produced by Newport Corporation) and Fiber Optic Spectrometer (USB2000, produced by Ocean Optics, Inc.). The electroluminescent (EL) spectra are shown in FIG. 6, the electric current density-voltage (J-V) characteristics are shown in FIG. 7, and the external quantum efficiency-electric current density characteristics are shown in FIG. 8. The organic electroluminescent device of Example 5 achieved a high external quantum efficiency of 9.56%.

Example 6

In this example, an organic electroluminescent device having a light-emitting layer formed only of the compound 1 was produced and evaluated for the characteristics thereof.

Thin films each were formed by a vacuum vapor deposition method at a vacuum degree of $5.0 \times 10^{-4}$ Pa on a glass substrate having formed thereon an anode formed of indium tin oxide (ITO) having a thickness of 100 nm. First, α-NPD was formed to a thickness of 40 nm on ITO. mCP was then formed to a thickness of 10 nm. The compound 1 was then vapor-deposited from a vapor deposition source to form a layer having a thickness of 30 nm, which was designated as a light-emitting layer. Bphen was then formed to a thickness of 20 nm. Lithium fluoride (LiF) was then vacuum vapor-deposited to a thickness of 0.8 nm, and then aluminum (Al) was vapor-deposited to a thickness of 80 nm, which was designated as a cathode, thereby completing an organic electroluminescent device. Light emission at 496 nm was observed, and the external quantum efficiency was 2.3%.

Example 7

In this example, another organic electroluminescent device having a light-emitting layer formed only of the compound 1 was produced and evaluated for the characteristics thereof.

Thin films each were formed by a vacuum vapor deposition method at a vacuum degree of $5.0 \times 10^{-4}$ Pa on a glass substrate having formed thereon an anode formed of indium tin oxide (ITO) having a thickness of 100 nm. First, α-NPD was formed to a thickness of 30 nm on ITO. mCP was then formed to a thickness of 10 nm. The compound 1 was then vapor-deposited from a vapor deposition source to form a layer having a thickness of 30 nm, which was designated as a light-emitting layer. TPBi was then formed to a thickness of 20 nm. Lithium fluoride (LiF) was then vacuum vapor-deposited to a thickness of 0.8 nm, and then aluminum (Al) was vapor-deposited to a thickness of 80 nm, which was designated as a cathode, thereby completing an organic electroluminescent device. Light emission at 491 nm was observed.
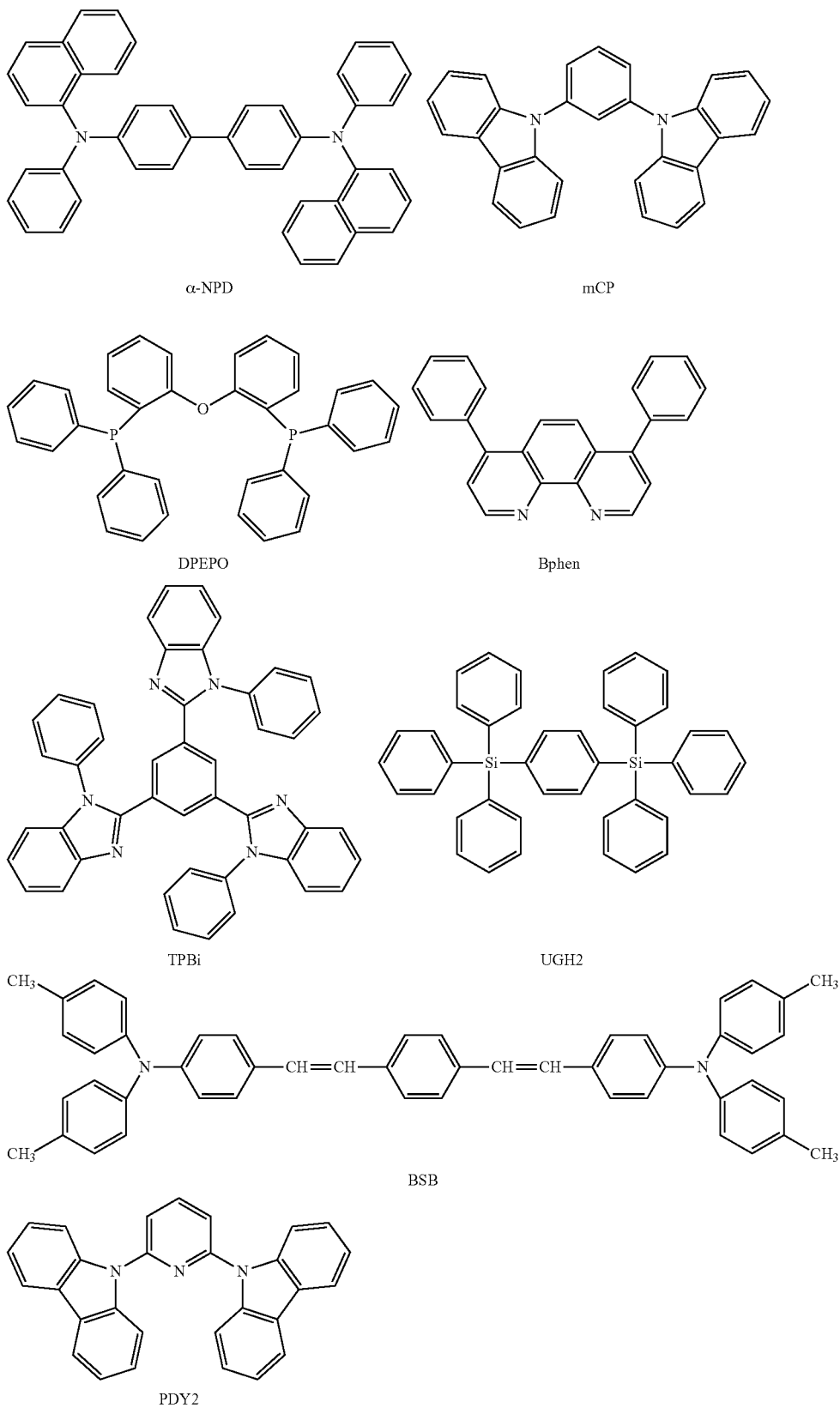

INDUSTRIAL APPLICABILITY

The organic light-emitting device of the invention is capable of achieving a high light emission efficiency. The compound of the invention is useful as a light-emitting material of such an organic light-emitting device. Accordingly, the invention has high industrial applicability.

REFERENCE SIGNS LIST 1 substrate
2 anode
3 hole injection layer
4 hole transporting layer
5 light-emitting layer
6 electron transporting layer
7 cathode

The invention claimed is:

1. An organic light-emitting device containing a substrate having thereon a light-emitting layer containing a compound represented by the following formula (3) as a light-emitting material emitting light from the organic light-emitting device:

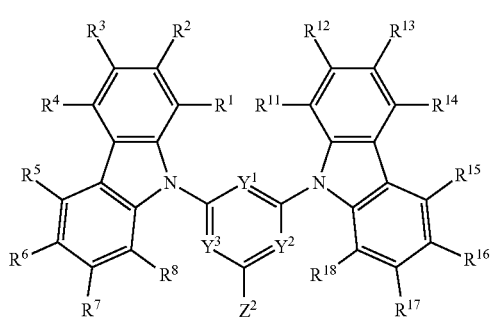

Formula (3)

wherein in the formula (3), $Y^1$, $Y^2$ and $Y^3$ all represent nitrogen atoms;
represents a hydrogen atom or a substituent selected from the group consisting of
(1) an alkyl group having from 1 to 20 carbon atoms,
(2) an aryl group having from 6 to 30 carbon atoms,
(3) a heteroaryl group having from 3 to 30 carbon atoms,
(4) a diarylamino group having from 12 to 30 carbon atoms,
(5) a carbazolyl group having from 12 to 30 carbon atoms,
(6) an alkyl group having from 1 to 20 carbon atoms, which is substituted by (2), (3), (4) and/or (5),
(7) an aryl group having from 6 to 30 carbon atoms, which is substituted by (1), (3), (4) and/or (5),
(8) a heteroaryl group having from 3 to 30 carbon atoms, which is substituted by (1), (2), (4) and/or (5),
(9) a diarylamino group having from 12 to 30 carbon atoms, which is substituted by (1), (2), (3) and/or (5), and
(10) a carbazolyl group having from 12 to 30 carbon atoms, which is substituted by (1), (2), (3) and/or (4); and
$R^1$ to $R^8$ and $R^{11}$ to $R^{18}$ each independently represent a hydrogen atom or a substituent selected independently from the group consisting of
(1) an alkyl group having from 1 to 20 carbon atoms,
(2) an aryl group having from 6 to 30 carbon atoms,
(3) a heteroaryl group having from 3 to 30 carbon atoms,
(4) a diarylamino group having from 12 to 30 carbon atoms,
(5) a carbazolyl group having from 12 to 30 carbon atoms,
(6) an alkyl group having from 1 to 20 carbon atoms, which is substituted by (2), (3), (4) and/or (5),
(7) an aryl group having from 6 to 30 carbon atoms, which is substituted by (1), (3), (4) and/or (5),
(8) a heteroaryl group having from 3 to 30 carbon atoms, which is substituted by (1), (2), (4) and/or (5),
(9) a diarylamino group having from 12 to 30 carbon atoms, which is substituted by (1), (2), (3) and/or (5), and
(10) a carbazolyl group having from 12 to 30 carbon atoms, which is substituted by (1), (2), (3) and/or (4),
provided that at least one of $R^1$ to $R^8$ and at least one of $R^{11}$ to $R^{18}$ each independently represent (4), (5), (9) or (10).

2. The organic light-emitting device according to claim 1, which emits delayed fluorescent light.

3. The organic light-emitting device according to claim 1, which is an organic electroluminescent device.

4. A delayed fluorescent emitter consisting of a compound represented by the following formula (3):

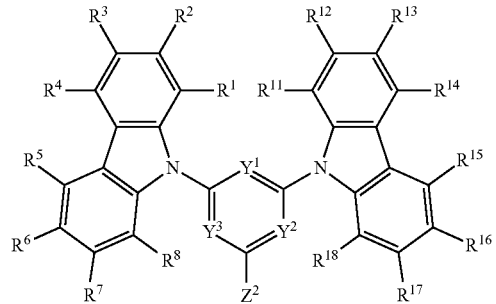

Formula (3)

wherein in the formula (3), $Y^1$, $Y^2$ and $Y^3$ all represent nitrogen atoms;
$Z^2$ represents a hydrogen atom or a substituent selected from the group consisting of:
(1) an alkyl group having from 1 to 20 carbon atoms,
(2) an aryl group having from 6 to 30 carbon atoms,
(3) a heteroaryl group having from 3 to 30 carbon atoms,
(4) a diarylamino group having from 12 to 30 carbon atoms,
(5) a carbazolyl group having from 12 to 30 carbon atoms,
(6) an alkyl group having from 1 to 20 carbon atoms, which is substituted by (2), (3), (4) and/or (5),
(7) an aryl group having from 6 to 30 carbon atoms, which is substituted by (1), (3), (4) and/or (5),
(8) a heteroaryl group having from 3 to 30 carbon atoms, which is substituted by (1), (2), (4) and/or (5),
(9) a diarylamino group having from 12 to 30 carbon atoms, which is substituted by (1), (2), (3) and/or (5), and
(10) a carbazolyl group having from 12 to 30 carbon atoms, which is substituted by (1), (2), (3) and/or (4); and
$R^1$ to $R^8$ and $R^{11}$ to $R^{18}$ each independently represent a hydrogen atom or a substituent selected independently from the group consisting of:
(1) an alkyl group having from 1 to 20 carbon atoms,
(2) an aryl group having from 6 to 30 carbon atoms,
(3) a heteroaryl group having from 3 to 30 carbon atoms,
(4) a diarylamino group having from 12 to 30 carbon atoms,
(5) a carbazolyl group having from 12 to 30 carbon atoms,
(6) an alkyl group having from 1 to 20 carbon atoms, which is substituted by (2), (3), (4) and/or (5), (7) an aryl group having from 6 to 30 carbon atoms, which is substituted by (1), (3), (4) and/or (5),
(8) a heteroaryl group having from 3 to 30 carbon atoms, which is substituted by (1), (2), (4) and/or (5),
(9) a diarylamino group having from 12 to 30 carbon atoms, which is substituted by (1), (2), (3) and/or (5), and
(10) a carbazolyl group having from 12 to 30 carbon atoms, which is substituted by (1), (2), (3) and/or (4),
provided that at least one of $R^1$ to $R^8$ and at least one of $R^{11}$ to $R^{18}$ each independently represent (4), (5), (9) or (10).

5. A compound represented by the following formula (11):

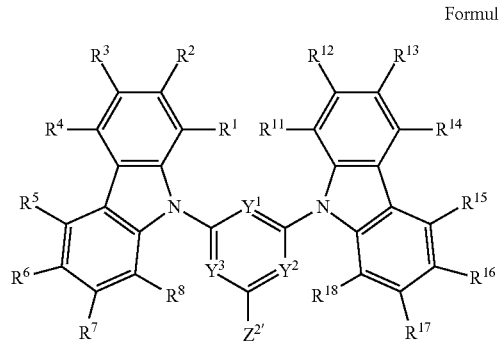

Formula (11)

wherein in the formula (11), $Y^1$, $Y^2$ and $Y^3$ all represent nitrogen atoms;
$Z^{2'}$ represents a hydrogen atom or a substituent that is bonded via a carbon atom (provided that the substituent does not contain a boron atom), said substituent being selected from the group consisting of
(1) an alkyl group having from 1 to 20 carbon atoms,
(2) an aryl group having from 6 to 40 carbon atoms,
(3) a cyano substituted aryl group having from 6 to 40 carbon atoms,
(4) a monocyclic heteroaryl group having from 3 to 5 carbon atoms,
(5) a diarylamino group having from 12 to 40 carbon atoms,
(6) an alkyl group having from 1 to 20 carbon atoms, which is substituted by (2), (3), (4) and/or (5),
(7) an aryl group having from 6 to 40 carbon atoms, which is substituted by (1), (3), (4) and/or (5),
(8) a cyano substituted aryl group having from 6 to 40 carbon atoms, which is substituted by (1), (2), (4) and/or (5),
(9) a monocyclic heteroaryl group having from 3 to 5 carbon atoms, which is substituted by (1), (2), (3) and/or (5), and
(10) a diarylamino group having from 12 to 40 carbon atoms, which is substituted by (1), (2), (3) and/or (4); and
$R^1$ to $R^8$ and $R^{11}$ to $R^{18}$ each independently represent a hydrogen atom or a substituent selected independently from the group consisting of
(1) an alkyl group having from 1 to 20 carbon atoms,
(2) an aryl group having from 6 to 40 carbon atoms,
(3) a cyano substituted aryl group having from 6 to 40 carbon atoms,
(4) a monocyclic heteroaryl group having from 3 to 5 carbon atoms,
(5) a diarylamino group having from 12 to 40 carbon atoms,
(6) an alkyl group having from 1 to 20 carbon atoms, which is substituted by (2), (3), (4) and/or (5),
(7) an aryl group having from 6 to 40 carbon atoms, which is substituted by (1), (3), (4) and/or (5),
(8) a cyano substituted aryl group having from 6 to 40 carbon atoms, which is substituted by (1), (2), (4) and/or (5),
(9) a monocyclic heteroaryl group having from 3 to 5 carbon atoms, which is substituted by (1), (2), (3) and/or (5), and
(10) a diarylamino group having from 12 to 40 carbon atoms, which is substituted by (1), (2), (3) and/or (4),
provided that at least one of $R^1$ to $R^8$ and at least one of $R^{11}$ to $R^{18}$ each independently represent (4), (5), (9) or (10).

6. The compound according to claim 5, which is represented by the following formula (12):

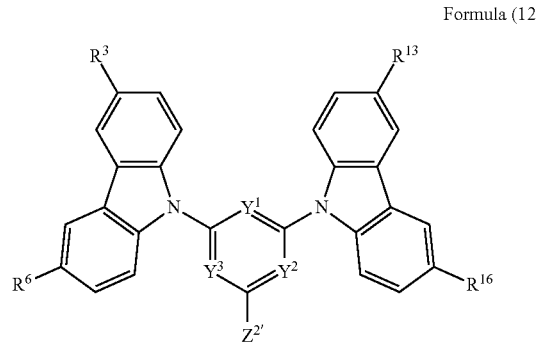

Formula (12)

wherein in the formula (12), $Y^1$, $Y^2$ and $Y^3$ all represent nitrogen atoms;
$Z^{2'}$ represents a hydrogen atom, or a substituent selected from the group consisting of:
(1) an alkyl group having from 1 to 20 carbon atoms,
(2) an aryl group having from 6 to 40 carbon atoms,
(3) a cyano substituted aryl group having from 6 to 40 carbon atoms,
(4) a monocyclic heteroaryl group having from 3 to 5 carbon atoms,
(5) a diarylamino group having from 12 to 40 carbon atoms,
(6) an alkyl group having from 1 to 20 carbon atoms, which is substituted by (2), (3), (4) and/or (5),
(7) an aryl group having from 6 to 40 carbon atoms, which is substituted by (1), (3), (4) and/or (5),
(8) a cyano substituted aryl group having from 6 to 40 carbon atoms, which is substituted by (1), (2), (4) and/or (5),
(9) a monocyclic heteroaryl group having from 3 to 5 carbon atoms, which is substituted by (1), (2), (3) and/or (5), and
(10) a diarylamino group having from 12 to 40 carbon atoms, which is substituted by (1), (2), (3) and/or (4);
and $R^3$, $R^6$, $R^{13}$ and $R^{16}$ each independently represent a hydrogen atom or a substituent independently selected from the group consisting of
(1) an alkyl group having from 1 to 20 carbon atoms,
(2) an aryl group having from 6 to 40 carbon atoms,
(3) a cyano substituted aryl group having from 6 to 40 carbon atoms,
(4) a monocyclic heteroaryl group having from 3 to 5 carbon atoms, (5) a diarylamino group having from 12 to 40 carbon atoms,
(6) an alkyl group having from 1 to 20 carbon atoms, which is substituted by (2), (3), (4) and/or (5),
(7) an aryl group having from 6 to 40 carbon atoms, which is substituted by (1), (3), (4) and/or (5),
(8) a cyano substituted aryl group having from 6 to 40 carbon atoms, which is substituted by (1), (2), (4) and/or (5),
(9) a monocyclic heteroaryl group having from 3 to 5 carbon atoms, which is substituted by (1), (2), (3) and/or (5), and
(10) a diarylamino group having from 12 to 40 carbon atoms, which is substituted by (1), (2), (3) and/or (4),
provided that at least one of $R^3$ and $R^6$ and at least one of $R^{13}$ and $R^{16}$ each independently represent (4), (5), (9) or (10).

\* \* \* \* \*